(12) United States Patent
Mehrkhodavandi et al.

(10) Patent No.: US 9,777,023 B2
(45) Date of Patent: Oct. 3, 2017

(54) DINUCLEAR INDIUM CATALYSTS AND THEIR USE FOR (CO)POLYMERIZATION OF CYCLIC ESTERS

(75) Inventors: Parisa Mehrkhodavandi, Vancouver (CA); Insun Yu, Vancouver (CA); J. Alberto Acosta-Ramirez, Whites Lake (CA)

(73) Assignee: University of British Columbia, Vancouver, British Columbia (CA)

(*) Notice: Subject to any disclaimer, the term of this patent is extended or adjusted under 35 U.S.C. 154(b) by 42 days.

(21) Appl. No.: 14/118,433

(22) PCT Filed: May 18, 2012

(86) PCT No.: PCT/CA2012/050331
§ 371 (c)(1),
(2), (4) Date: Jul. 21, 2014

(87) PCT Pub. No.: WO2012/155275
PCT Pub. Date: Nov. 22, 2012

(65) Prior Publication Data
US 2015/0038651 A1    Feb. 5, 2015

Related U.S. Application Data

(60) Provisional application No. 61/487,626, filed on May 18, 2011.

(30) Foreign Application Priority Data

May 18, 2011    (CA) .................................... 2740821

(51) Int. Cl.
| C08G 63/84 | (2006.01) |
| C07F 5/00 | (2006.01) |
| C08G 63/82 | (2006.01) |
| B01J 31/22 | (2006.01) |

(52) U.S. Cl.
CPC ............ *C07F 5/006* (2013.01); *C08G 63/823* (2013.01); *C08G 63/84* (2013.01); *B01J 31/2243* (2013.01); *B01J 2531/0216* (2013.01); *B01J 2531/0238* (2013.01); *B01J 2531/33* (2013.01)

(58) Field of Classification Search
CPC ................................ C07F 5/006; C08G 63/84
See application file for complete search history.

(56) References Cited

FOREIGN PATENT DOCUMENTS

WO    WO 2012/155275 A1    11/2012

OTHER PUBLICATIONS

Hsieh et al., "Indium complexes incorporating bidentate substituted pyrrole ligand: Synthesis, characterization, and ring-opening polymerization of ε-caprolactone", Inorg. Chim,Acta, vol. 359, Issue 2, pp. 497-504, Jan. 2006.*
USPTO structure search, Jan. 2016.*
Douglas et al (A Highly Active Chiral Indium Catalyst for Living Lactide Polymerization, Angew. Chem. Int. Ed. 2008, 47, 2290-2293).*
International Search Report, International Application No. PCT/CA2012/050331, entitled "Catalysts and Methods for Cyclic Ester (Co)Polymerization, and Polymer and Copolymer Products", International filing date: May 18, 2012, Date of Communication: Aug. 20, 2012.
Written Opinion of the International Searching Authority, International Application No. PCT/CA2012/050331, entitled "Catalysts and Methods for Cyclic Ester (Co)Polymerization, and Polymer and Copolymer Products", International filing date: May 18, 2012, Date of Communication: Aug. 20, 2012.
International Preliminary Report on Patentability, International Application No. PCT/CA2012/050331, entitled "Catalysts and Methods for Cyclic Ester (Co)Polymerization, and Polymer and Copolymer Products", International filing date: May 18, 2012, Date of Communication: Oct. 2, 2013.
Acosta-Ramirez, A., et al., "Synthesis and structural studies of chiral indium (III) complexes supported by tridentate diaminophenol ligands", Inorg. Chem., vol. 49 (12), pp. 5444-5452, 2010.
Douglas, A. F., et al., "A highly active chiral indium catalyst for living lactide polymerization", Angew. Chem. Int. Ed., vol. 47 (12), pp. 2290-2293, 2008.
Osten, K. M., et al., "Effects of ligand tuning on dinuclear indium catalysts for lactide polymerization", Dalton Trans., vol. 41 (26), pp. 8123-8134, Mar. 8, 2012.
Othman, N., et al., "Thermoheological and mechanical behavior of polylactide and its enantiometric diblock copolymers and blends", Polymer, vol. 53 (12), pp. 2443-2452, Apr. 18, 2012.
Xu, C., et al., "Highly Controlled immortal polymerization of β-butyrolactone by a dinuclear indium catalyst", Chem. Commun., vol. 48 (54), pp. 6806-6808, May 16, 2012.
Campbell, E.J. and Nguyen, S.T., "Unsymmetrical Salen-Type Ligands: High Yeild Synthesis of Salen-Type Schiff Bases Containing Two Different Benzaldehyde Moieties", Tetrahedron Letters, 42:1221-1225 (2001).
Hiki, S., et al., "Synthesis and Characterization of Hydroxy-Terminated [RS]-poly(3-hydroxybutyrate) and its Utilization to Block Coplolymerization With L-Lactide to Obtain a Biodegradable Thermoplastic Elastomer", Polymer, 41:7369-7379 (2000).

(Continued)

*Primary Examiner* — Gregory Listvoyb
(74) *Attorney, Agent, or Firm* — Hamilton, Brook, Smith & Reynolds, P.C.

(57) ABSTRACT

Provided are novel dinuclear indium catalysts of formula (A) that are capable of living and immortal ring opening polymerization and copolymerization of cyclic ester monomers for the preparation of biodegradable polymers and copolymers, in particular polyesters. Also disclosed are polymerization methods and polymer products. These dinuclear indium catalysts allow less costly, highly reactive living polymerization of cyclic ester monomers with possible high turn over rates and/or substantial stereo-chemical and microstructure control.

(A)

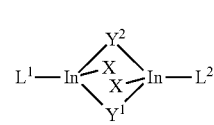

12 Claims, 15 Drawing Sheets

(56) References Cited

OTHER PUBLICATIONS

Holbach, M., et al., "A Practical One-Pot Synthesis of Enantiopure Unsymmetrical Salen Ligands", *J. Org. Chem. Note*, 71:2903-2906 (2006).
Ovitt, T.M. and Coates, G.W., "Steroselective Ring-Opening Polymerization of *rac*-Lactide with a Single-Site, Racemic Aluminum Alkoxide Catalyst: Synthesis of Teroblock Poly(lactic acid)", *J. Polym Scie A: Poly Chem*, 38:4686-4692 (2000).
Mehrkhodavandi, P., et al., "Highly Active Catalysts for Ring Opening Polymerization of Lactide." Paper presented at the CSC National Conference, Hamilton, Ontario, (May 30-Jun. 3, 2009).
Mehrkhodavandi, P., et al., "Dinuclear Indium Catalysts for Enatioselective Polymerization of Lactide." Presented at the Inorganic Gordon Research Conference, University of British Columbia, (Jun. 20-26, 2010).
Woo, E.M. and Chang, L., "Crystallization and Morphology of Sterocomplexes in Nonequimolar Mixtures of poly(L-lactic acid) with excess poly(D-lactic acid)", Polymer, 52:6080-6089 (2011).
Dauth, A. and Love, J.A., "Synthesis and Reactivity of 2-Azametallacyclobutanes", *Dalton Trans.*, 41:7782-7791 (2012).
Extended European Search Report for EP12785681.3, "Dinuclear Indium Catalysts and Their Use for (Co)Polymerization of Cyclic Esters", dated Jul. 15, 2015.
Mehrkhodavandi, P., et al., "Chiral Indium Catalysts for Controlled Polymerization of Lactide", presented at the Canadian Society for Chemistry (CSC) National Conference, University of British Columbia, Toronto, Canada,(May 30-Jun. 2, 2010), 22 pages.

\* cited by examiner

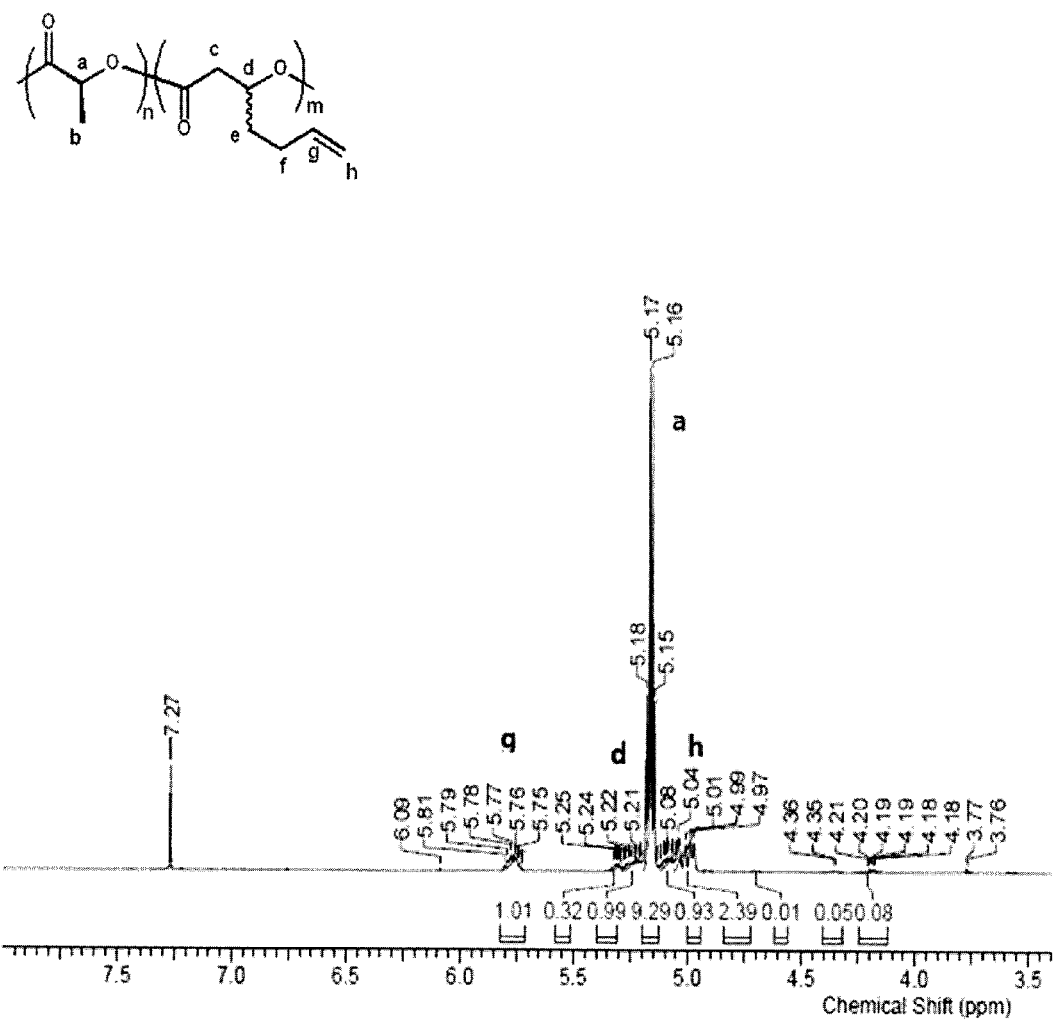
FIGURE 2 ctd.

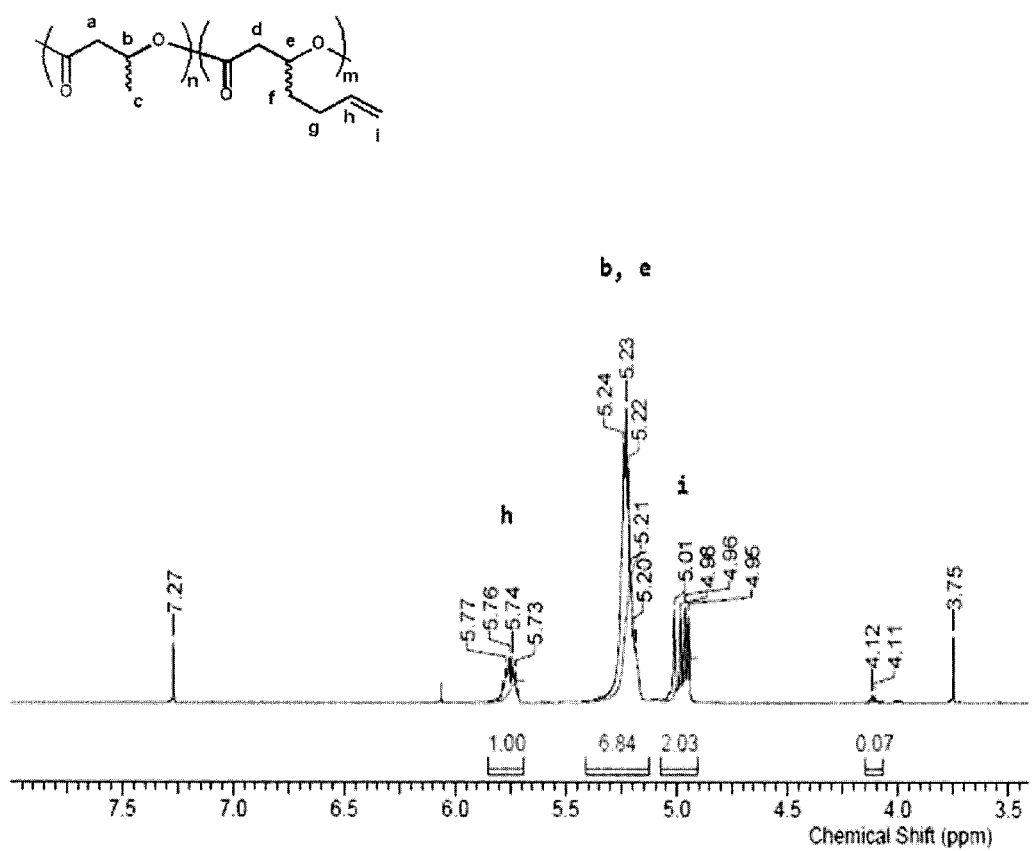
FIGURE 3 ctd.

DINUCLEAR INDIUM CATALYSTS AND THEIR USE FOR (CO)POLYMERIZATION OF CYCLIC ESTERS

CROSS-REFERENCE

This application is the U.S. National Stage of International Application No. PCT/CA2012/050331, filed May 18, 2012, which designates the U.S., published in English, and claims the benefit of U.S. Provisional Application No. 61/487,626, filed May 18, 2011 and claims priority under 35 U.S.C. §§119 or 365(c) to Canadian Application No. 2,740,821, filed May 18, 2011, the entireties of which are incorporated herein.

BACKGROUND OF THE INVENTION

Polymers prepared by cyclic ester polymerization and copolymerization such as poly(lactone)s and poly(lactide)s are interesting polymer systems in that they typically are biodegradable and bioassimilable. In addition, a number of monomers used to produce these polymers can be produced from biomass using enzyme technology or living organisms such as yeast.

Poly(lactic acid) (PLA), produced by ring-opening polymerization (ROP) of lactide (LA), is a leading biodegradable and biocompatible polyester with wide-ranging applications. Several well-defined Lewis acid catalysts have been developed for this reaction; prominent among them are metal alkoxides based on aluminum, zinc, and rare-earth metals, as well as organocatalysts. These known systems have successfully addressed one or more important factors in the ROP of LA, such as activity and catalyst toxicity. Enantioselectivity, in particular, has garnered much attention, and catalysts with exquisite control over PLA tacticity have been reported. Nevertheless, in most cases examples of highly selective catalysts that exhibit site control remain confined to aluminum salen complexes, which have low reactivity and functional-group tolerance.

There is a need for improved catalysts for the living polymerization and copolymerization of cyclic ester monomers. Improved catalysts can be, for example, less costly or highly reactive providing high turnover rates, enhanced stereochemical control or enhanced microstructure control, for example, by way of block copolymer self assembly and precise control over block ratio. Other desirable characteristics of improved catalysts include reduced toxicity, increased functional-group tolerance, increased stability or the ability to produce high molecular weight polymers and copolymers, particularly, with narrow molecular weight distribution. There is further a need for polymers and copolymers produced with such improved catalysts, specifically; there is a need for biodegradable polymers and copolymers with controlled microstructure.

This background information is provided for the purpose of making known information believed by the applicant to be of possible relevance to the present invention. No admission is necessarily intended, nor should be construed, that any of the preceding information constitutes prior art against the present invention.

SUMMARY OF THE INVENTION

The invention relates to indium catalysts, a process for polymerization of cyclic ester monomers using the indium catalysts and the polymers and copolymers prepared by the process.

A first embodiment of the present invention is a catalyst represented by structural formula (A):

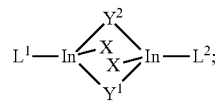

(A)

wherein $L^1$ and $L^2$ are each independently a tridentate ligand represented by structural formula (B):

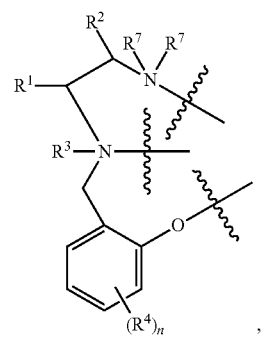

(B)

or a stereoisomer thereof;

each $R^7$ independently is —$(C_1-C_4)$alkyl;

$Y^1$ is O—$R^6$ or OH;

$Y^2$ is O—$R^6$, OH, Cl, Br, or I;

each $R^6$ independently is —$(C_1-C_6)$alkyl;

n is 0 to 4;

each $R^1$ and $R^2$ is independently a —H or —$(C_1-C_4)$alkyl; or $R^1$ and $R^2$ together with the carbon atoms to which they are bonded form a $(C_5-C_7)$cycloalkyl ring, optionally substituted with up to two groups selected independently from —$(C_1-C_4)$alkyl, —$(C_1-C_4)$alkoxy, phenyl, —$CF_3$, —F, —Cl, —Br, and —I;

$R^3$ is —H or —$(C_1-C_3)$alkyl;

each X is independently an anionic ligand; and each $R^4$ independently is —$(C_1-C_5)$alkyl;

or a stereoisomer of the catalyst represented by structural formula (A);

provided that when $L^1$ and $L^2$ are both represented by structural formula:

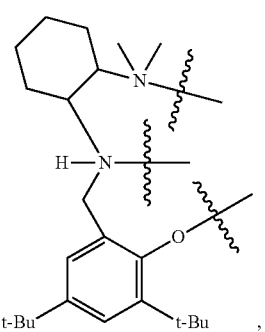

then the catalyst is not represented by structural formula:

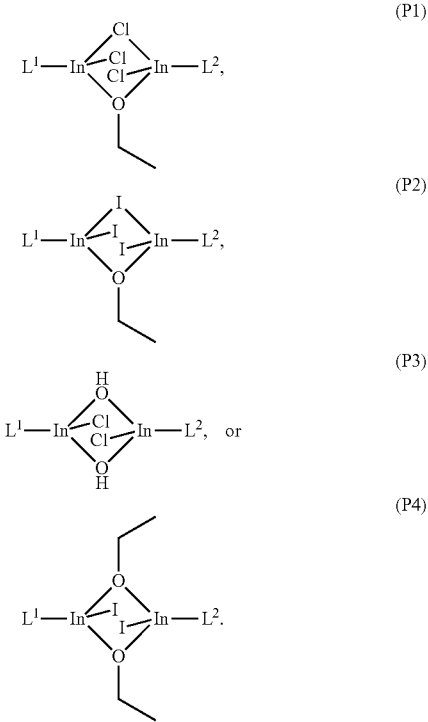

A second embodiment of the present invention is a method comprising polymerizing a cyclic ester monomer with a catalyst represented by structural formula (A) or a stereoisomer thereof under conditions suitable for ring-opening polymerization of the cyclic ester monomer.

The catalyst is represented by structural formula A, $L^1$ and $L^2$ are each independently a tridentate ligand represented by structural formula (B), provided that when the tridentate ligands $L^1$ and $L^2$ are represented by the following structural formula:

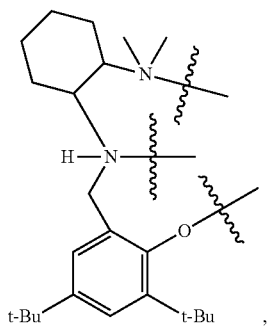

and the catalyst is represented by structural formula (P1), (P2), (P3) or (P4), then the cyclic ester monomer is not L-lactide, D-lactide, meso-lactide or rac-lactide.

A third embodiment of the present invention is copolymerization method for preparing a block copolymer. The method comprises (a) polymerizing a first cyclic ester monomer with a catalyst represented by structural formula (A) or a stereoisomer thereof under conditions suitable for ring-opening polymerization of the first cyclic ester monomer to foam a first polymer block of the block copolymer; and (b) polymerizing a second cyclic ester monomer, different from the first cyclic ester monomer, with a catalyst represented by structural formula (A) or a stereoisomer thereof under conditions suitable for ring-opening polymerization of the second cyclic ester monomer to form a second polymer block of the block copolymer. In a particular embodiment, the first cyclic ester monomer and the second cyclic ester monomer are independently represented by structural formula (I).

A fourth embodiment of the present invention is a polymer prepared by a process comprising polymerizing a cyclic ester monomer such as the cyclic ester monomer represented by structural formula (I) with a catalyst represented by structural formula (A) or a stereoisomer thereof under conditions suitable for ring-opening polymerization of the cyclic ester monomer, provided that when the tridentate ligands $L^1$ and $L^2$ are represented by the following structural formula:

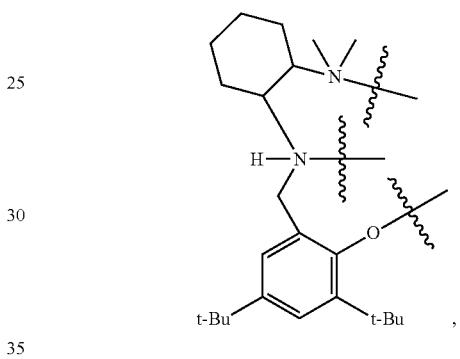

and the catalyst is represented by structural formula (P1), (P2), (P3) or (P4), then the cyclic ester monomer is not L-lactide, D-lactide, meso-lactide or rac-lactide.

A fifth embodiment of the present invention is a block copolymer. The block copolymer is prepared by a process comprising: (a) polymerizing a first cyclic ester monomer such as the cyclic ester monomer represented by structural formula (I) with a catalyst represented by structural formula (A) or a stereoisomer thereof under conditions suitable for ring-opening polymerization of the first cyclic ester monomer to form a first polymer block of the block copolymer; and (b) polymerizing a second cyclic ester monomer such as the cyclic ester monomer represented by structural formula (I), different from the first cyclic ester monomer, with a catalyst represented by structural formula (A) or a stereoisomer thereof under conditions suitable for ring-opening polymerization of the second cyclic ester monomer to form a second polymer block of the block copolymer.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

DETAILED DESCRIPTION OF THE INVENTION

Dinuclear Indium Catalysts

Figure 1:
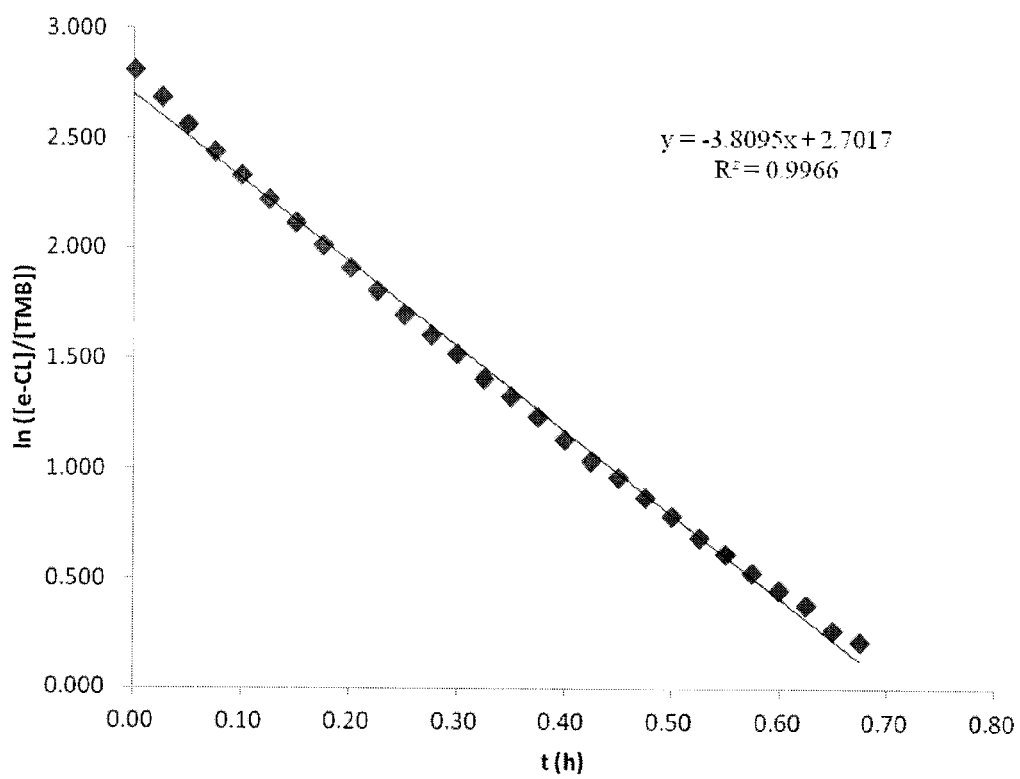
FIG. 1 shows the relative concentration of c-caprolactone against time in the polymerization of ϵ-caprolactone with [(NNO)InCl]$_2$(μ-OEt)(μ-Cl).

The catalysts of the present invention can be described by structural formula (A). They are initiator and catalyst complexes for the ring-opening polymerization of cyclic esters as described herein. Each tridentate ligand bonds with one indium metal ion via one covalent bond between O and In and two co-ordinate (dative covalent) bonds between N and In; these three bonds are indicated by the "—" between L$^1$ and In, and between L$^2$ and the other In, for example, in structural formula (A). These same bonds are also indicated as three "—" extending from N, N, and O, respectively, in the structural formulas for the tridentate ligands, for example, structural formula (B). Additionally, each Y$^1$ is bridged between the two In by bonds indicated by "—". Further, each ligand X is bonded with one In. With regard to the bridging ligands Y$^1$ and Y$^2$, when the group is a O—R$^6$ or OH, it is to be understood that the oxygen atom participates in the bonding.

The invention also includes various isomers and mixtures of catalysts. Certain of the catalysts of the present invention may exist in various stereoisomeric forms. Stereoisomers are compounds which differ only in their spatial arrangement. Enantiomers are pairs of stereoisomers whose mirror images are not superimposable, most commonly because they contain an asymmetrically substituted carbon atom that acts as a chiral center. "Enantiomer" means one of a pair of molecules that are mirror images of each other and are not superimposable. Diastereomers are stereoisomers that are not related as mirror images, most commonly because they contain two or more asymmetrically substituted carbon atoms. "R" and "S" represent the configuration of substituents around one or more chiral carbon atoms. When a chiral center is not defined as R or S, either a pure enantiomer or a mixture of both configurations is present.

More specifically, "stereoisomers" of the catalysts as referred to herein, include the below "cis" and "trans" stereoisomers, as well as enantiomers and diastereomers thereof, (note that for simplicity only the co-ordinate bonding N, N and O atoms of the tridentate ligands are shown):

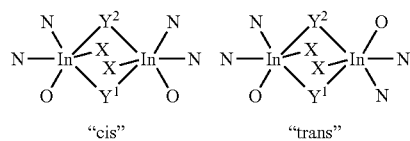

"cis"  "trans"

"Racemate" or "racemic mixture" means a compound of equimolar quantities of two enantiomers, wherein such mixtures exhibit no optical activity; i.e., they do not rotate the plane of polarized light.

The compounds of the invention may be prepared as individual isomers by either isomer specific synthesis or resolved from an isomeric mixture.

When the stereochemistry of a disclosed compound is named or depicted by structure, the named or depicted stereoisomer is at least 60%, 70%, 80%, 90%, 99% or 99.9% pure relative to the other stereoisomers, for example, by weight or as determined by spectroscopic analysis. When a single enantiomer is named or depicted by structure, the depicted or named enantiomer is at least 60%, 70%, 80%, 90%, 99% or 99.9% by weight optically pure. Percent optical purity by weight is the ratio of the weight of the enantiomer that is present divided by the combined weight of the enantiomer that is present and the weight of its optical isomer.

The tridentate ligands L$^1$ and L$^2$ can be different chemical groups, different stereoisomers, different enantiomers, or the same enantiomers. Typically, when L$^1$ and L$^2$ are the same chemical group, they are also the same enantiomer. For example, for a ligand with two asymmetric centers, the catalyst typically is of (RR,RR) and/or (SS,SS) form.

A sixth embodiment of the present invention is a catalyst represented by structural formula (A), or a stereoisomer thereof:

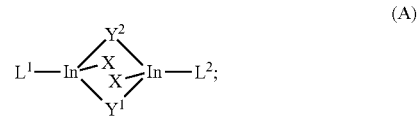

(A)

wherein L$^1$ and L$^2$ are each independently a tridentate ligand represented by structural formula (B):

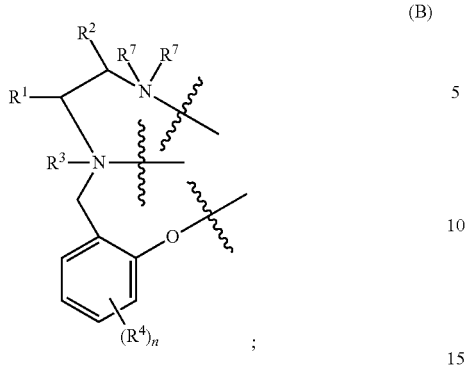

(B)

Values and alternative values for the variables in structural formula (A) and (B) are provided in the following paragraphs. It is understood that the invention encompasses all combinations of the substituent variables defined herein.

Each $R^7$ is independently —$(C_1$-$C_4)$alkyl. Alternatively, both $R^7$ are the same —$(C_1$-$C_4)$alkyl. In yet another alternative, both $R^7$ are methyl, ethyl or propyl. In yet another alternative, both $R^7$ propyl.

$Y^1$ is O—$R^6$ or OH. Alternatively, $Y^1$ is $OCH_2CH_3$ or OH. In yet another alternative, $Y^1$ is $OCH_2CH_3$.

$Y^2$ is O—$R^6$, OH, Cl, Br, or I. Alternatively, $Y^2$ is $OCH_2CH_3$, OH, Cl, Br, or I.

Each $R^6$ independently is —$(C_1$-$C_6)$alkyl. Alternatively, both $R^6$ independently are —$(C_1$-$C_6)$alkyl. In yet another alternative, both $R^6$ are $OCH_2CH_3$. n is 0 to 4. Alternatively, n is 0 to 2. In yet another alternative, n is 2.

Each $R^1$ and $R^2$ is independently a —H or —$(C_1$-$C_4)$alkyl; or $R^1$ and $R^2$ together with the carbon atoms to which they are bonded form a $(C_5$-$C_7)$cycloalkyl ring, optionally substituted with up to two groups selected independently from —$(C_1$-$C_4)$alkyl, —$(C_1$-$C_4)$alkoxy, phenyl, —$CF_3$, —F, —Cl, —Br, and —I. Alternatively, $R^1$ and $R^2$ are —H; or $R^1$ and $R^2$ together with the carbon atoms to which they are bonded form a cyclohexyl ring, optionally substituted with up to two groups selected independently from —$(C_1$-$C_4)$alkyl, —$(C_1$-$C_4)$alkoxy, —$CF_3$, —F, —Cl, —Br, or —I. In yet another alternative, $R^1$ and $R^2$ are —H; or $R^1$ and $R^2$ together with the carbon atoms to which they are bonded form a cyclohexyl ring.

$R^3$ is —H or —$(C_1$-$C_3)$alkyl. Alternatively, $R^3$ is —H or methyl. Each X is independently an anionic ligand. Alternatively, each X is independently $(C_1$-$C_4)$alkoxy, $BF_4$, $PF_6$, acetate, acetylacetonate, trifluoroacetate, F, Cl, or I. In yet another alternative, each X is independently Cl, Br or I. In yet another alternative, both X are Cl, Br or I.

Each $R^4$ independently is —$(C_1$-$C_5)$alkyl. Alternatively, each $R^4$ is independently methyl, ethyl, n-propyl, isopropyl, n-butyl, isobutyl, sec-butyl, or tert-butyl. In yet another alternative, each $R^4$ is independently methyl or tert-butyl (i.e., t-butyl or tBu). In yet another alternative, n is 2, and one $R^4$ is in para position to the phenol hydroxyl and is methyl or tert-butyl and one $R^4$ is ortho position to the phenol hydroxyl and is tert-butyl.

In a 1$^{st}$ specific embodiment, the catalyst of the present invention is represented by structural formula (A), or a stereoisomer thereof, and $L^1$ and $L^2$ are each independently a tridentate ligand represented by structural formula (C1), (C2), (D1), (D2), (D3), (E1) or (E2), or a stereoisomer thereof:

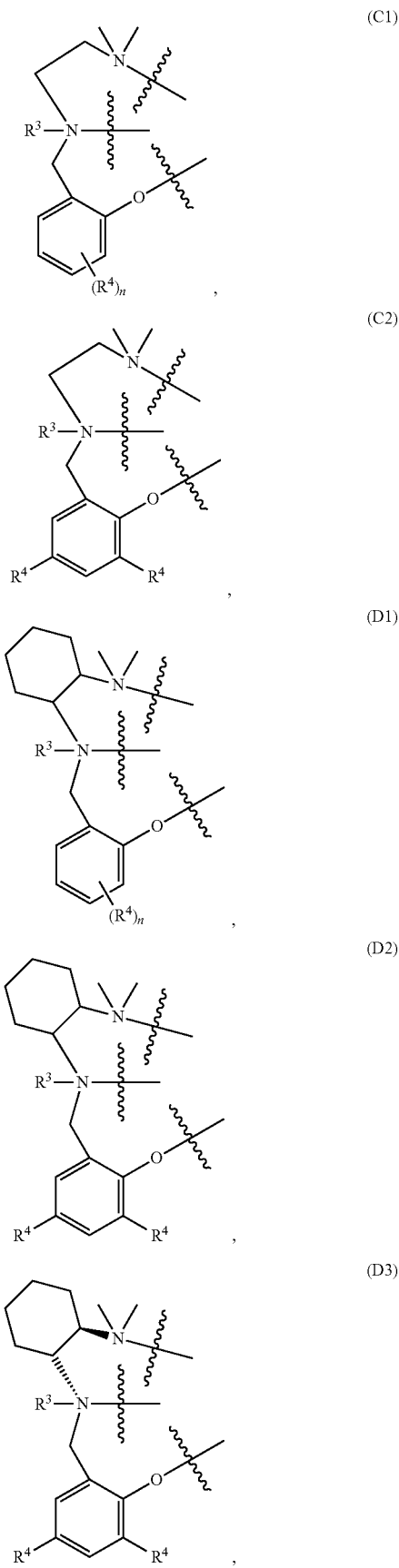

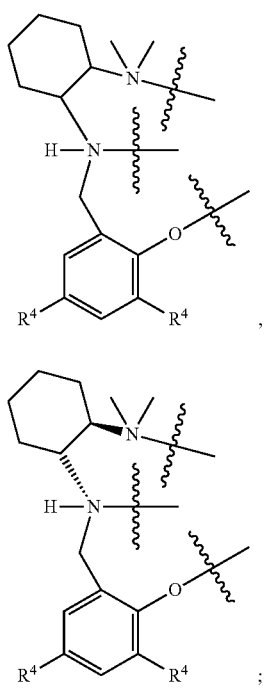
(E1)
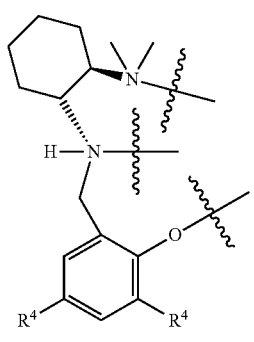
(E2)
and values and alternative values for the remainder of the variables are as described for the sixth embodiment.
In a 2$^{nd}$ specific embodiment, the catalyst of the present invention is represented by structural formula (E3a), (E4a), (E5a), (C3), (C3t), (D4), (D5) or (D6):
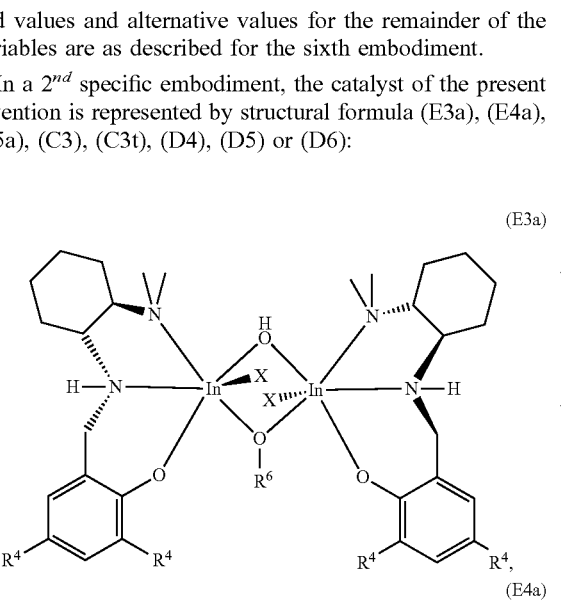
(E3a)
(E4a)
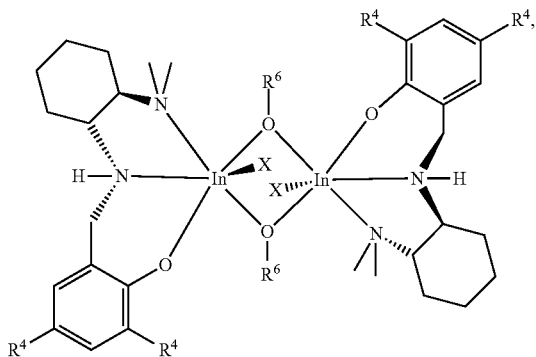
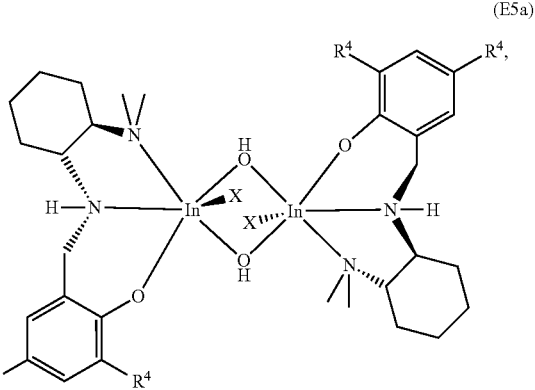
(E5a)
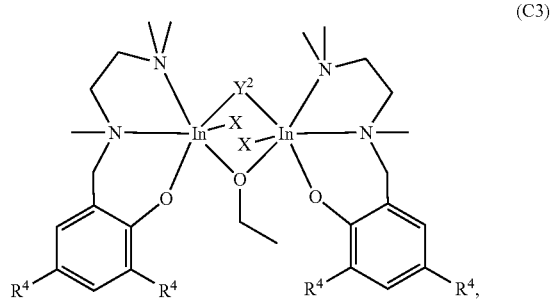
(C3)
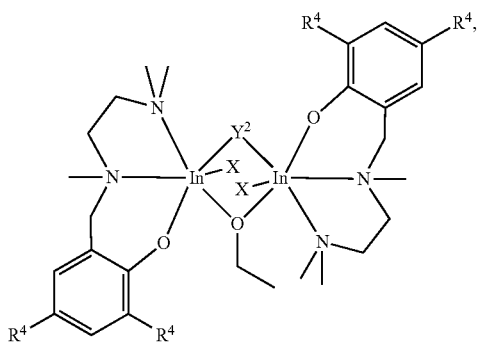
(C3t)
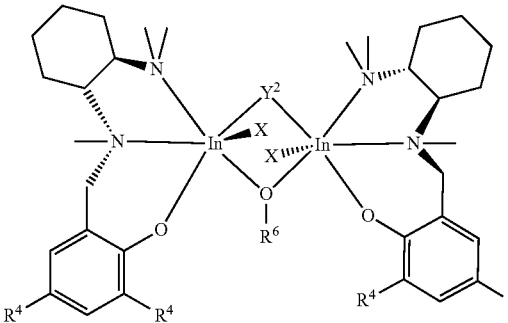
(D4)

(D5)

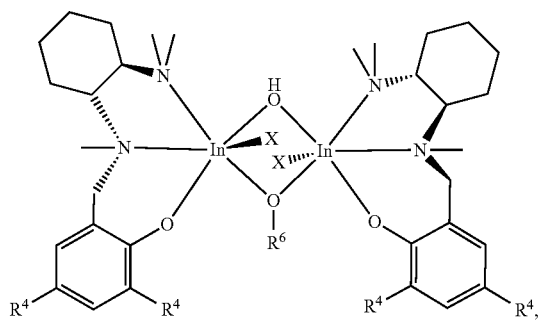

(D6)

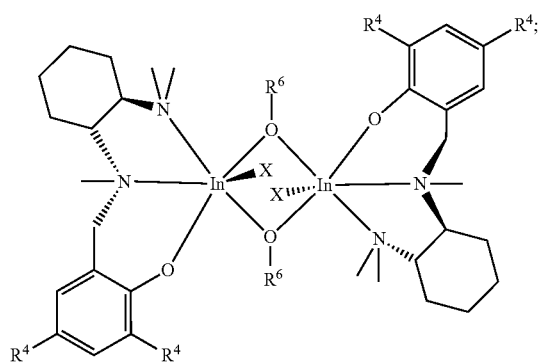

wherein $Y^2$ is $OCH_2CH_3$, OH, Cl, Br or I, and values and alternative values for the remainder of the variables are as described for the sixth embodiment.

In a $3^{rd}$ specific embodiment, the catalyst of the present invention is represented by structural formula (E3a), (E4a), (D5) or (D6):

(E3a)

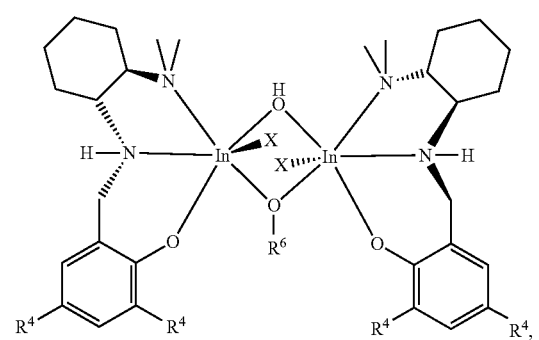

(E4a)

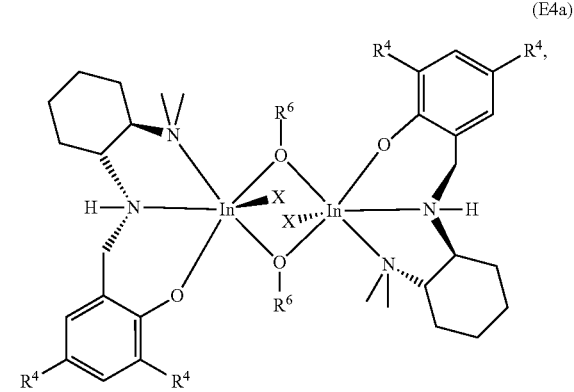

(D5)

(D6)

and values and alternative values for the remainder of the variables are as described for the sixth embodiment.

In a $4^{th}$ specific embodiment, the catalyst of the present invention is represented by structural formula (A), or a stereoisomer thereof, and $L^1$ and $L^2$ are each independently a tridentate ligand represented by structural formula (C1), (D1), or (E1), or a stereoisomer thereof:

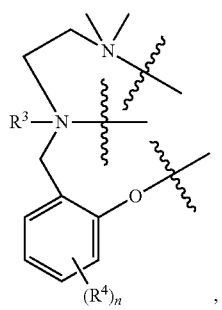
(C1)

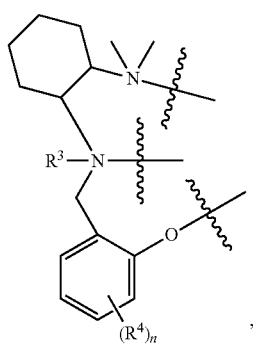
(D1)

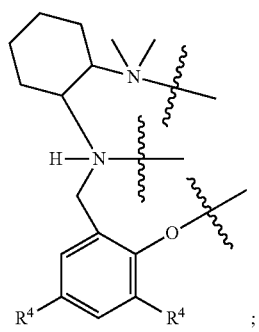
(E1)

and values and alternative values for the remainder of the variables are as described in the sixth embodiment.

In a 5th specific embodiment, the catalyst of the present invention is represented by structural formula (A), or a stereoisomer thereof, and $L^1$ and $L^2$ are each independently a tridentate ligand represented by structural formula (C2) or (D2), or a stereoisomer thereof:

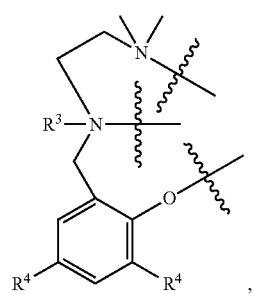
(C2)

(D2)

and values and alternative values for the remainder of the variables are as described in the sixth embodiment.

In a 6th specific embodiment, the catalyst of the present invention is represented by structural formula (A), or a stereoisomer thereof, and $L^1$ and $L^2$ are each independently a tridentate ligand represented by structural formula (D3) or (E2), or a stereoisomer thereof:

(D3)

(E2)

and values and alternative values for the remainder of the variables are as described in the sixth embodiment.

In a seventh embodiment, the catalyst is represented by structural formula (P1)

$$L^1-In\overset{\overset{Cl}{\diagdown}}{\underset{\underset{O}{\diagup}}{\overset{Cl}{\diagup}}}\overset{Cl}{\underset{}{}}In-L^2,$$

(P2) 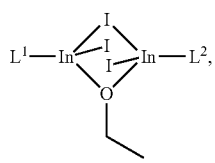
(P3) 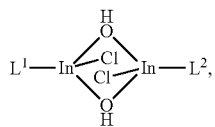
(P4) 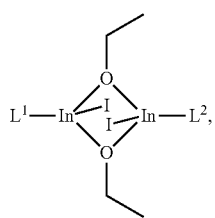
(P5) 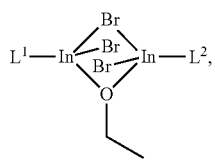
(P6) 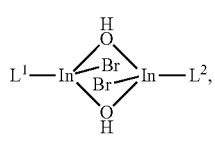
(P7) 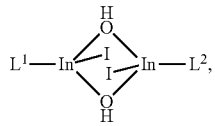
(P8) 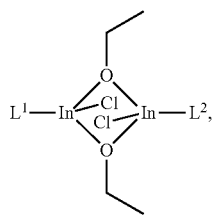
(P9) 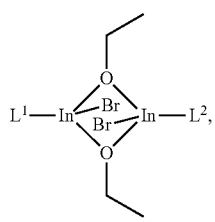
(P10) 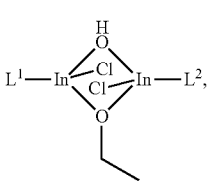
(P11) 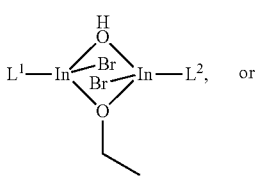
or
(P12) 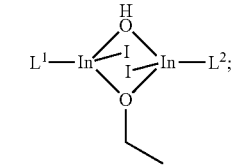
or a stereoisomer thereof;
wherein $L^1$ and $L^2$ are each independently a tridentate ligand represented by structural formula (C1), (D1), or (E1), or a stereoisomer thereof.
(C1) 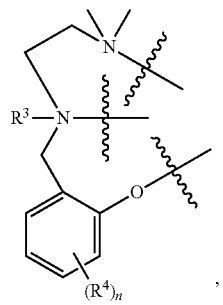
(D1) 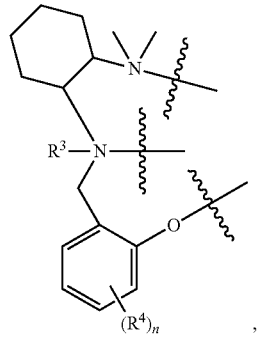
(E1) 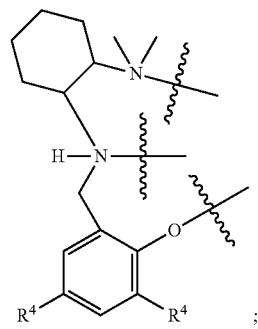
and values and alternative values for the remainder of the variables are as described in the sixth embodiment.

In a 7th specific embodiment, the catalyst of the present invention is the one of the seventh embodiment, wherein it is further provided that $L^1$ and $L^2$ are not both represented by structural formula:
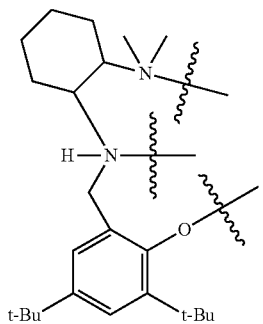
In an eight embodiment, the catalyst is represented by structural formula (C4), (C4t), (C5), (C5t), (E6), (E7) or (E8):
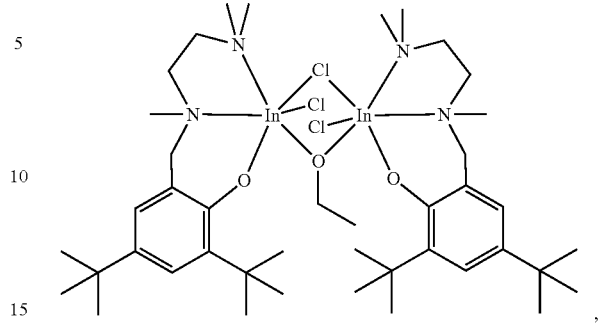
(C4)
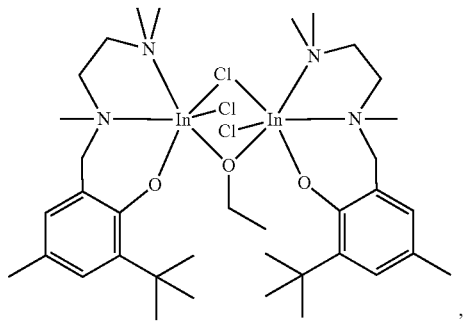
(C4t)
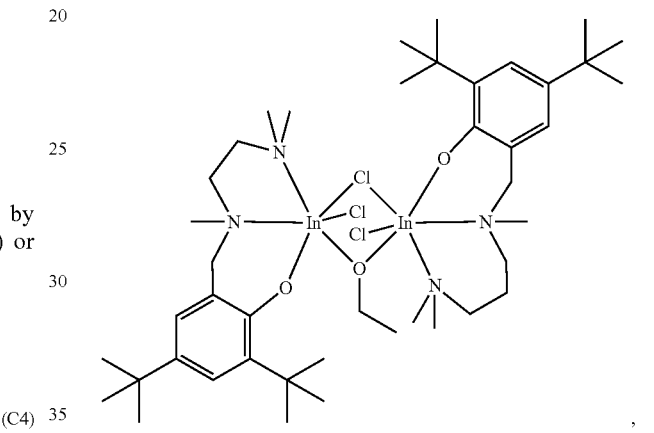
(C5)
(C5t)
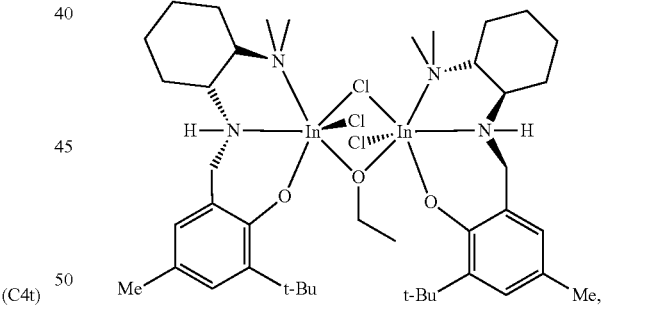
(E6)
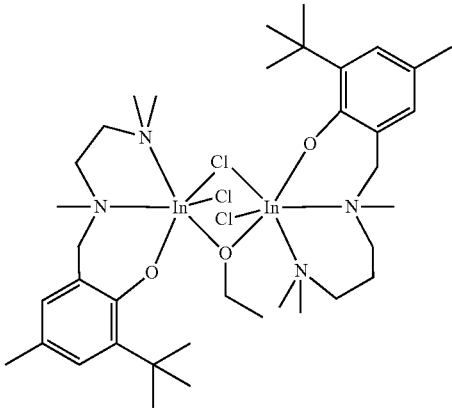
(E7)

-continued (E8)

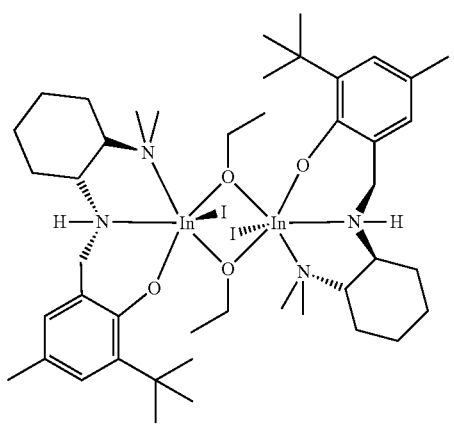

In a ninth embodiment, the catalyst of the present invention is the one of the sixth embodiment, the $1^{st}$ specific embodiment, the $2^{nd}$ specific embodiment, the $3^{rd}$ specific embodiment, the $4^{th}$ specific embodiment, the $5^{th}$ specific embodiment, or the $6^{th}$ specific embodiment, wherein it is further provided that when $L^1$ and $L^2$ are both represented by structural formula:

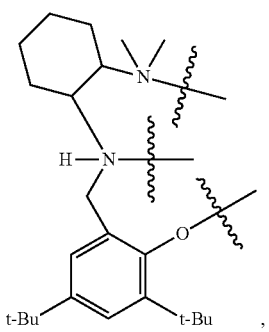

then the catalyst is not represented by structural formula:

(P1)

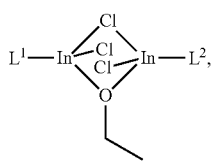

(P2)

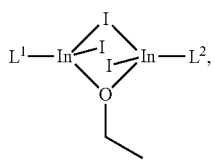

(P3)

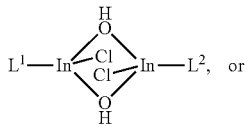

-continued (P4)

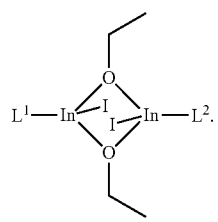

In a tenth embodiment, the catalyst of the present invention is the one of the sixth embodiment, the $1^{st}$ specific embodiment, the $2^{nd}$ specific embodiment, the $3^{rd}$ specific embodiment, the $4^{t}$ specific embodiment, the $5^{th}$ specific embodiment, or the $6^{th}$ specific embodiment, wherein it is further provided that when $L^1$ and $L^2$ are both represented by structural formula:

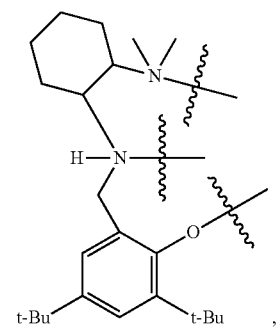

then the catalyst is not represented by structural formula:

(P1)

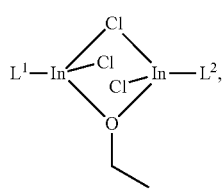

(P2)

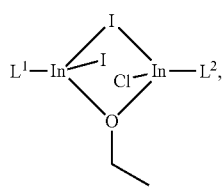

(P3)

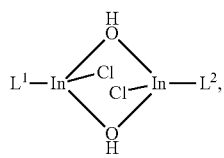

-continued (P4) 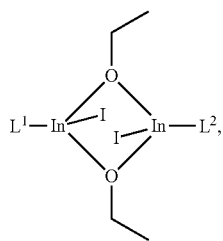

(P5) 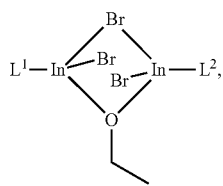

(P6) 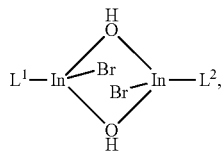

(P7) 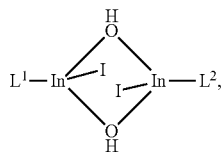

(P8) 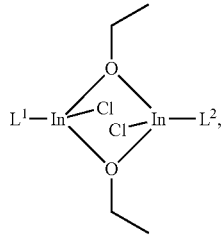

(P9) 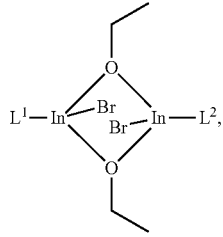

(P10) 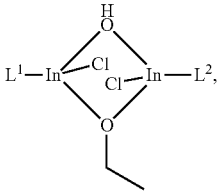

-continued (P11) 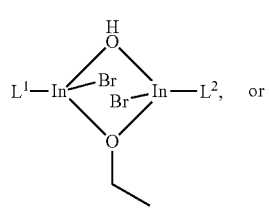, or (P12) 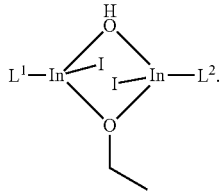.

A 7$^{th}$ specific embodiment is a catalyst composition comprising a catalyst represented by structural formula (F):

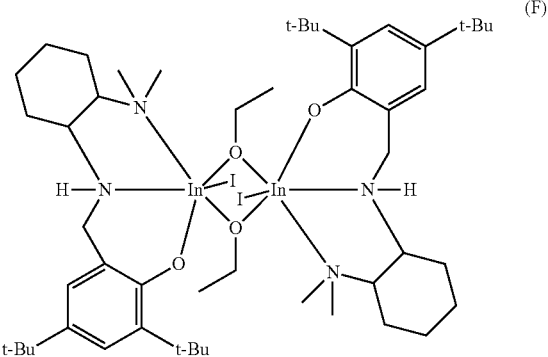

(F)

in at least 80% purity. More typically, the composition comprises the catalyst represented by structural formula (F) in at least 90% purity. Even more typically, the composition comprises the catalyst represented by structural formula (F) in at least 95% purity.

An 8$^{th}$ specific embodiment is a catalyst composition comprising a catalyst represented by structural formula (F1):

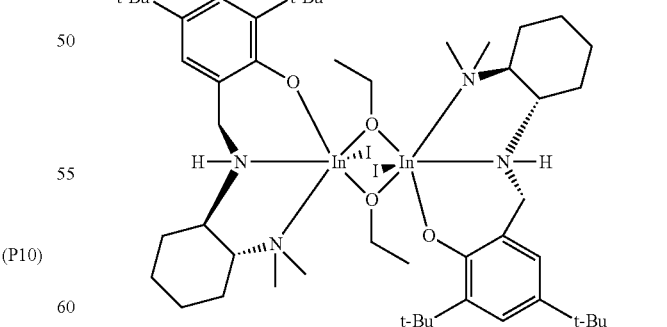

(F1)

in at least 80% purity. More typically, the composition comprises the catalyst represented by structural formula (F1) in at least 90% purity. Even more typically, the composition comprises the catalyst represented by structural formula (F1) in at least 95% purity.

A 9th specific embodiment is a catalyst composition comprising a catalyst represented by structural formula (F2):

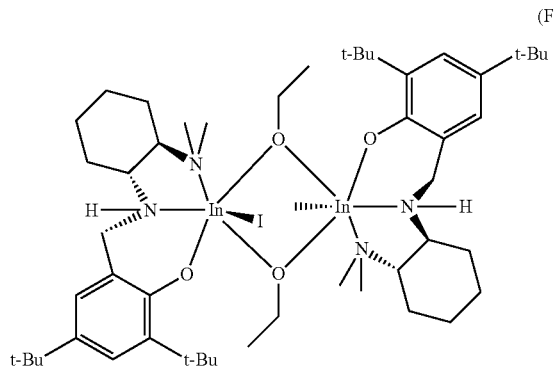

in at least 80% purity. More typically, the composition comprises the catalyst represented by structural formula (F2) at least 90% purity. Even more typically, the composition comprises the catalyst represented by structural formula (F2) in at least 95% purity.

"Purity" as referred to herein with regard to catalyst compositions, refers to purity as determined by 1H NMR spectroscopy in solution.

Polymerization and Copolymerization Methods

The dinuclear indium complexes as described in the previous section are initiators and catalysts of the ring opening polymerization of cyclic ester monomers. It has been found that these complexes can facilitate living ring opening polymerization. Accordingly, the below described polymerization methods can be living ring opening polymerization including copolymerization methods.

Suitable cyclic ester monomers include, but are not limited to cyclic ester monomers represented by the following structural formula (I):

wherein
m is 1 to 4;
Q is —CH$_2$—, —C(HR''')—, or —C(R'''R''')—;
each Z is independently —CH$_2$—, —O—, —C(=O)—, —C(HR''')—, or —C(R'''R''')—; and each R''' is i) —(C$_1$-C$_5$)alkyl optionally substituted with hydroxyl, —(C$_1$-C$_3$)alkoxy or —O—(C$_1$-C$_3$)alkenyl, ii) —(C$_1$-C$_5$)alkenyl, or iii) (C$_1$-C$_5$) X''' wherein X'''=F, Cl, Br, or I;
or a stereoisomer thereof.

Alternatively, suitable cyclic ester monomers include, but are not limited to cyclic ester monomers represented by the following structural formula (I):

wherein
m is 1 to 4;
Q is —CH$_2$—, —C(HR''')—, or —C(R'''R''')—;
each Z is independently —CH$_2$—, —O—, —C(=O)—, —C(HR''')—, or —C(R'''R''')—; and
each R''' is i) —(C$_1$-C$_5$)alkyl optionally substituted with hydroxyl, —(C$_1$-C$_3$)alkoxy or —O—(C$_1$-C$_3$)alkenyl, or ii) —(C$_1$-C$_5$)alkenyl;
or a stereoisomer thereof.

The ring-opening polymerization of a cyclic ester monomer to form a polymer or polymer block of a copolymer is performed under suitable conditions, that is any condition under which the cyclic ester monomer is polymerized by the catalyst to form a polymer or polymer block of a copolymer. More particularly, suitable conditions can include polymerizing in a suitable solvent system, that is a single solvent or a solvent mixture. Suitable solvent systems allow the catalyst and the cyclic ester monomer to be in solution in at least part of the solvent system, and include but are not limited to toluene, THF, CH$_2$Cl$_2$, acetonitrile, chlorobenzene, ether, chloroform. The ring-opening polymerization can also be performed without solvent, for example, as neat polymerization in liquid or molten monomer. Additionally, suitable conditions include suitable temperatures. Typically, the temperature should at least be high enough for the solvent system to be a liquid. More typically, the temperature is between 0° C. and 110° C., even more typically, between 20° C. and 100° C. Even further, suitable conditions include suitable catalyst concentration, typically, from 0.1-5 mM.

A plurality of different cyclic ester monomers can be polymerized at the same time, or during different times of the entire polymerization process. With regard to the below embodiments directed to polymerization and copolymerization methods, steps (a), (b), and optionally (c) can occur at the same time, overlap in time, or can be separate in time.

Further, with regard to the copolymerization methods described in below embodiments, the first cyclic ester monomers can be polymerized in a solvent or solvent system and the second cyclic ester monomer is added to the solvent or solvent system (either directly or in a second miscible second solvent). If the second cyclic ester monomer is added before the first cyclic ester monomer is substantially polymerized but after the first cyclic ester monomer has been polymerized to form a first polymer block, typically, both cyclic ester monomers will be polymerized at the same time resulting in a copolymer block (which can be random copolymer block), that is, the resulting copolymer includes at least the first polymer block covalently bonded to the copolymer block.

The ring-opening polymerization methods of the present invention can be living polymerization methods, that is, polymerizing steps can be living polymerizing steps in the methods disclosed herein.

Typically, in living polymerization, cyclic ester monomer is polymerized at very low polymer chain termination rates (i.e., the ability of the growing polymer chains to terminate is substantially removed). The result can be that the polymer chains grow at a more constant rate (compared to traditional chain polymerization) and the polymer chain lengths remain very similar (i.e., they have a very low polydispersity index).

The ring-opening polymerization methods of the present invention can further be immortal ring opening polymerization methods, that is, polymerizing steps can be immortal polymerizing steps in the methods disclosed herein.

Typically, in immortal ring opening polymerization (iROP) of a cylic ester monomer, external nucleophiles act as both initiators and chain transfer agents in conjunction with a catalyst. The result can be that catalytic productivity is enhanced and metal contamination of polymers significantly reduced in comparison to classic living systems, while the polymer chain end is functionalized with the chosen chain transfer agent.

A description of further polymerization and copolymerization embodiments follows below.

Polymerization Methods

An 11$^{th}$ embodiment of the present invention is a method comprising polymerizing a cyclic ester monomer with a catalyst under conditions suitable for ring-opening polymerization of the cyclic ester monomer, wherein the catalyst is as described in any one of the embodiments 6 to 10, or as in any one of the specific embodiments 1 to 9, provided that when the tridentate ligands L$^1$ and L$^2$ are represented by structural formula:

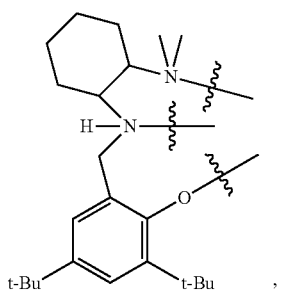

and the catalyst is represented by structural formula:

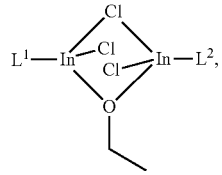
(P1)

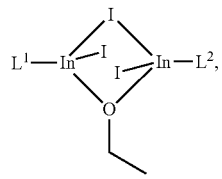
(P2)

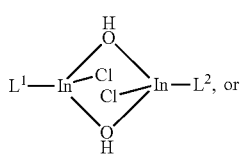
(P3)

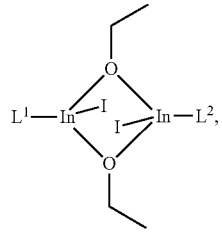
(P4)

then the cyclic ester monomer is not L-lactide, D-lactide, meso-lactide or rac-lactide.

A 12$^{th}$ embodiment of the present invention is a method comprising polymerizing a cyclic ester monomer with a catalyst under conditions suitable for ring-opening polymerization of the cyclic ester monomer, wherein the catalyst is as described in any one of the embodiments 6 to 10, or as in any one of the specific embodiments 1 to 9, provided that when the tridentate ligands L$^1$ and L$^2$ are represented by structural formula:

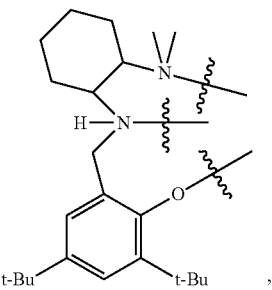

and the catalyst is represented by structural formula:

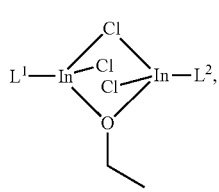
(P1)

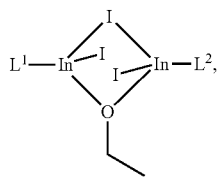
(P2)

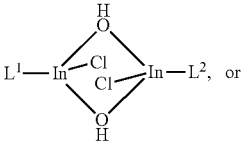
(P3)

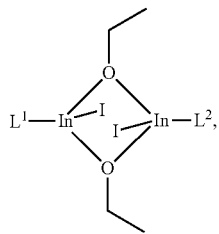
(P4)

then the cyclic ester monomer is not L-lactide, D-lactide, meso-lactide or rac-lactide.

The cyclic ester monomer is represented by the following structural formula (I):

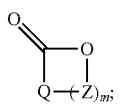
(I)

wherein m is 1 to 4;

Q is —CH$_2$—, —C(HR$^m$)—, or —C(R$^m$R$^m$)—;

each Z is independently —CH$_2$—, —O—, —C(=O)—, —C(HR$^m$)—, or —C(R$^m$R$^m$)—; and each R$^m$ is i) —(C$_1$-C$_5$)alkyl optionally substituted with hydroxyl, —(C$_1$-C$_3$)alkoxy or —O—(C$_1$-C$_3$)alkenyl, ii) —(C$_1$-C$_5$)alkenyl, or iii) (C$_1$-C$_5$) X$^{III}$ wherein X$^m$=F, Cl, Br, or I;

or a stereoisomer thereof;

provided that (i) no more than one Z is —O—, (ii) no more than one Z is —C(=O)—, (iii) at least one carbon ring atom is between any two oxygen ring atoms, (iv) at least one carbon ring atom is between any two —C(=O)— groups, and (v) at least one of any three consecutive ring members is —CH$_2$—, —C(HR$^m$)—, or —C(R$^m$R$^m$)—.

In a more particular embodiment, the cyclic ester monomer is represented by the following structural formula (I):

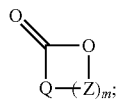
(I)

wherein m is 1 to 4;

Q is —CH$_2$—, —C(HR$^m$)—, or —C(R$^m$R$^m$)—;

each Z is independently —CH$_2$—, —O—, —C(=O)—, —C(HR$^m$)—, or —C(R$^m$R$^m$)—; and each R$^m$ is i) —(C$_1$-C$_5$)alkyl optionally substituted with hydroxyl, —(C$_1$-C$_3$)alkoxy or —O—(C$_1$-C$_3$)alkenyl, or ii) —(C$_1$-C$_5$)alkenyl. A 13$^{th}$ embodiment of the present invention is a method comprising polymerizing a cyclic ester monomer with a catalyst under conditions suitable for ring-opening polymerization of the cyclic ester monomer, wherein the catalyst is as described in any one of the embodiments 6 to 10, or as in any one of the specific embodiments 1 to 9, provided that when the tridentate ligands L$^1$ and L$^2$ are represented by structural formula:

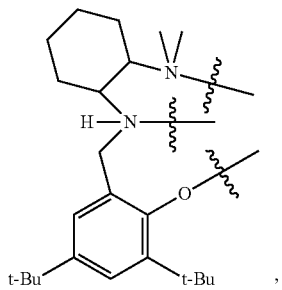

and the catalyst is represented by structural formula:

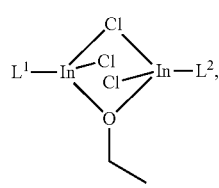
(P1)

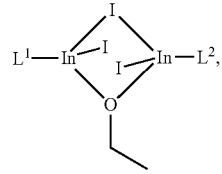
(P2)

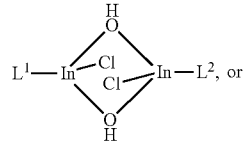
(P3)

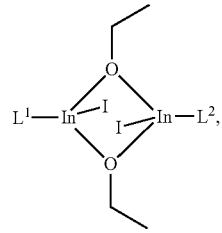
(P4)

then the cyclic ester monomer is not L-lactide, D-lactide, meso-lactide or ac-lactide.

The cyclic ester monomer is a di-lactone represented by structural formula (II) or a lactone represented by structural formula (III):

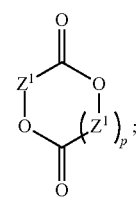
(II)

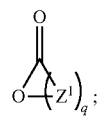
(III)

wherein p is 1 or 2;

q is 2 to 5;

each Z$^1$ is independently —CH$_2$—, —C(HR$^m$)—, or —C(R$^m$R$^m$)—; and each R$^m$ is i) —(C$_1$-C$_5$)alkyl optionally substituted with hydroxyl, —(C$_1$-C$_3$)alkoxy or —O—(C$_1$-C$_3$)alkenyl, ii) —(C$_1$-C$_5$)alkenyl, or iii) (C$_1$-C$_5$) X$^m$ wherein X$^m$=F, Cl, Br, or I;

or a stereoisomer thereof.

In a more particular embodiment, the cyclic ester monomer is represented by the following structural formula (I):

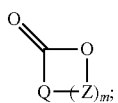
(I)

wherein m is 1 to 4;

Q is —CH$_2$—, —C(HR$'''$)—, or —C(R$'''$R$'''$)—;

each Z is independently —CH$_2$—, —O—, —C(=O)—, —C(HR$'''$)—, or —C(R$'''$R$'''$)—; and each R$'''$ is i) —(C$_1$-C$_5$)alkyl optionally substituted with hydroxyl, —(C$_1$-C$_3$)alkoxy or —O—(C$_1$-C$_3$)alkenyl, or ii) —(C$_1$-C$_5$)alkenyl.

A 14$^{th}$ embodiment of the present invention is a method comprising polymerizing a cyclic ester monomer with a catalyst under conditions suitable for ring-opening polymerization of the cyclic ester monomer, wherein the catalyst is as described in any one of the embodiments 6 to 10, or as in any one of the specific embodiments 1 to 9, provided that when the tridentate ligands L$^1$ and L$^2$ are represented by structural formula:

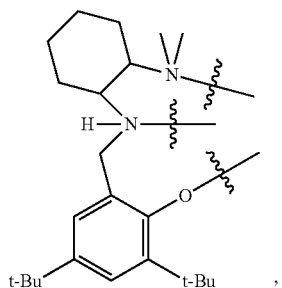

and the catalyst is represented by structural formula:

(P1)

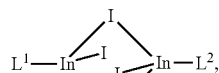
(P2)

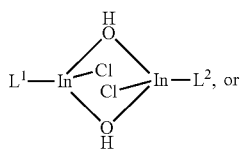
(P3)

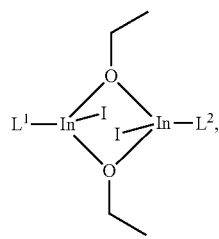
(P4)

then the cyclic ester monomer is not L-lactide, D-lactide, meso-lactide or rac-lactide.

The cyclic ester monomer is represented by structural formula:

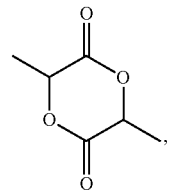
(IV)

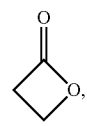
(V)

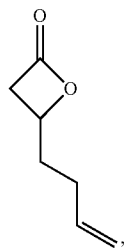
(VI)

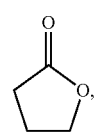
(VII)

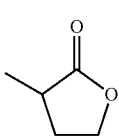
(VIII)

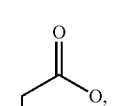
(IX)

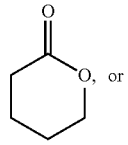
(X)

or a stereoisomer thereof.

An 15$^{th}$ embodiment of the present invention is a method comprising polymerizing a cyclic ester monomer with a catalyst under conditions suitable for ring-opening polymerization of the cyclic ester monomer, wherein the catalyst is as described in any one of the embodiments 6 to 10, or as in any one of the specific embodiments 1 to 9, provided that when the tridentate ligands L$^1$ and L$^2$ are represented by structural formula:

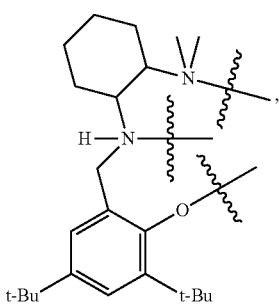

and the catalyst is represented by structural formula:

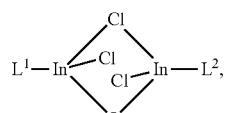
(P1)

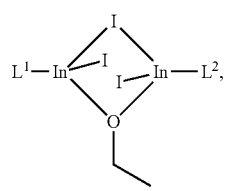
(P2)

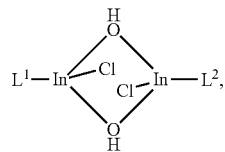
(P3)

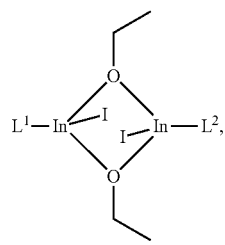
(P4)

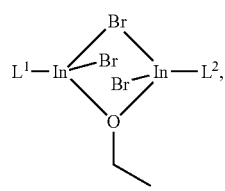
(P5)

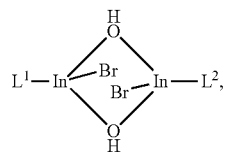
(P6)

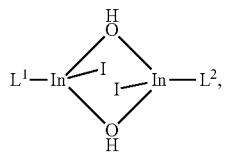
(P7)

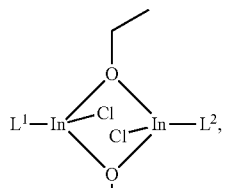
(P8)

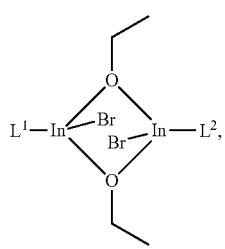
(P9)

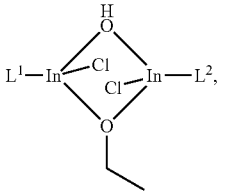
(P10)

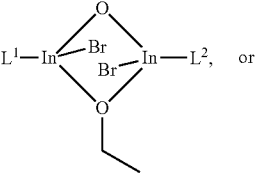
(P11) or

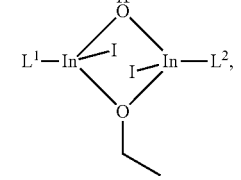
(P12)

then the cyclic ester monomer is not L-lactide, D-lactide, meso-lactide or rac-lactide.

A 16$^{th}$ embodiment of the present invention is a method comprising polymerizing a cyclic ester monomer with a catalyst under conditions suitable for ring-opening polymerization of the cyclic ester monomer, wherein the catalyst is as described in any one of the embodiments 6 to 10, or as in any one of the specific embodiments 1 to 9, provided that when the tridentate ligands L$^1$ and L$^2$ are represented by structural formula:

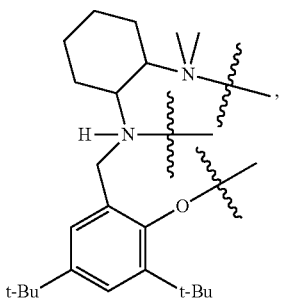

and the catalyst is represented by structural formula:

(P1)
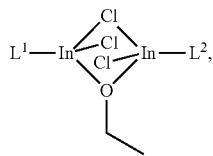

(P2)
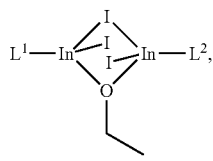

(P3)
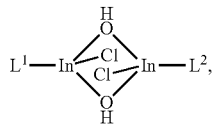

(P4)
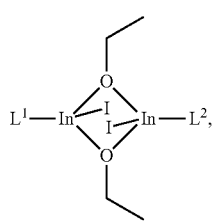

(P5)
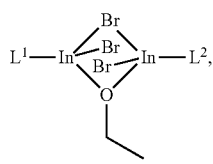

(P6)
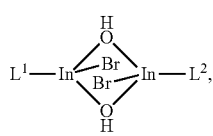

(P7)
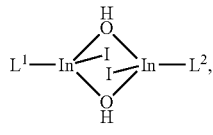

-continued (P8)
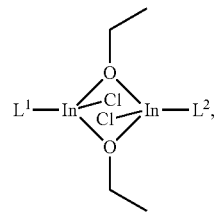

(P9)
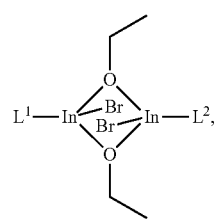

(P10)
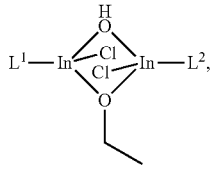

(P11)
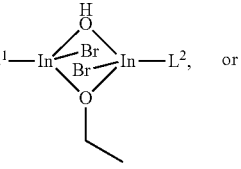    or (P12)
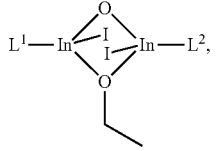

then the cyclic ester monomer is not L-lactide, D-lactide, meso-lactide or rac-lactide.

The cyclic ester monomer is represented by the following structural formula (I):

(I)

wherein
m is 1 to 4;
Q is —$CH_2$—, —$C(HR^m)$—, or —$C(R^m R^m)$—;
each Z is independently —$CH_2$—, —O—, —C(=O)—, —$C(HR^m)$—, or —$C(R^m R^m)$—; and
each $R^m$ is i) —$(C_1$-$C_5)$alkyl optionally substituted with hydroxyl, —$(C_1$-$C_3)$alkoxy or —O—$(C_1$-$C_3)$alkenyl, ii) —$(C_1$-$C_5)$alkenyl, or iii) $(C_1$-$C_5)$ $X^m$ wherein $X^m$=F, Cl, Br, or I;
or a stereoisomer thereof;
provided that (i) no more than one Z is —O—, (ii) no more than one Z is —C(=O)—, (iii) at least one carbon ring atom is between any two oxygen ring atoms, (iv) at least one carbon ring atom is between any two —C(=O)— groups, and (v) at least one of any three consecutive ring members is —CH$_2$—, —C(HR$'''$)—, or —C(R$'''$R$'''$)—.

In a more particular embodiment, the cyclic ester monomer is represented by the following structural formula (I):

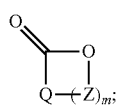
(I)

wherein m is 1 to 4;

Q is —CH$_2$—, —C(HR$'''$)—, or —C(R$'''$R$'''$)—;

each Z is independently —CH$_2$—, —O—, —C(=O)—, —C(HR$'''$)—, or —C(R$'''$R$'''$)—; and each R$'''$ is i) —(C$_1$-C$_5$)alkyl optionally substituted with hydroxyl, —(C$_1$-C$_3$)alkoxy or —O—(C$_1$-C$_3$)alkenyl, or ii) —(C$_1$-C$_5$)alkenyl.

A 17$^{th}$ embodiment of the present invention is a method comprising polymerizing a cyclic ester monomer with a catalyst under conditions suitable for ring-opening polymerization of the cyclic ester monomer, wherein the catalyst is as described in any one of the embodiments 6 to 10, or as in any one of the specific embodiments 1 to 9, provided that when the tridentate ligands L$^1$ and L$^2$ are represented by structural formula:

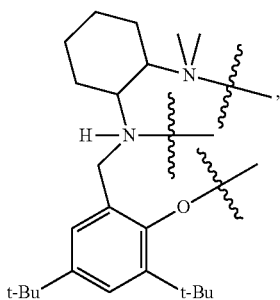

and the catalyst is represented by structural formula:

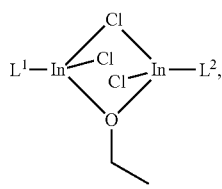
(P1)

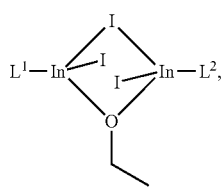
(P2)

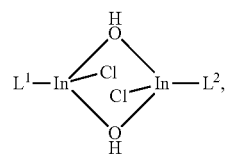
(P3)

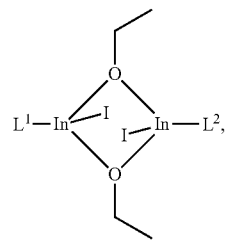
(P4)

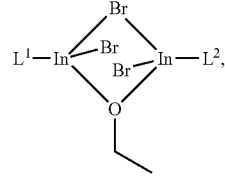
(P5)

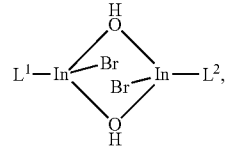
(P6)

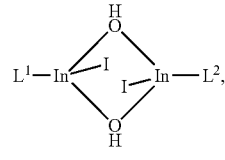
(P7)

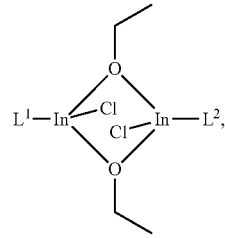
(P8)

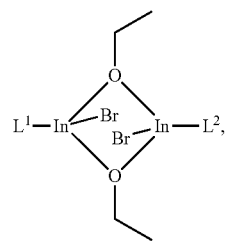
(P9)

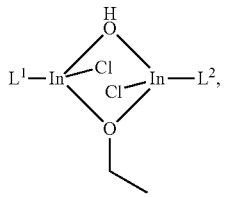
(P10)

-continued

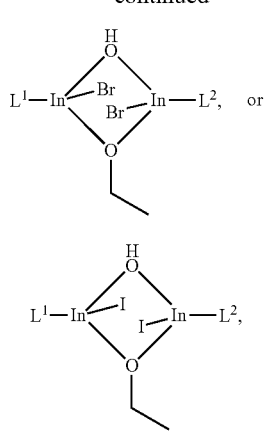

(P11)

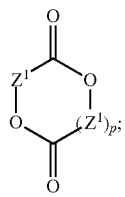

(P12)

then the cyclic ester monomer is not L-lactide, D-lactide, meso-lactide or rac-lactide.

The cyclic ester monomer is a di-lactone represented by structural formula (II) or a lactone represented by structural formula (III):

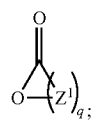

(II)

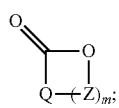

(III)

wherein
p is 1 or 2;
q is 2 to 5;
each $Z^1$ is independently —$CH_2$—, —$C(HR^m)$—, or —$C(R^m R^m)$—; and
each $R^m$ is i) —$(C_1-C_5)$alkyl optionally substituted with hydroxyl, —$(C_1-C_3)$alkoxy or —O—$(C_1-C_3)$alkenyl, ii) —$(C_1-C_5)$alkenyl, or iii) $(C_1-C_5)X^m$ wherein $X^m$=F, Cl, Br, or I;
or a stereoisomer thereof.

In a more particular embodiment, the cyclic ester monomer is represented by the following structural formula (I):

$$Q\!\!-\!\!(Z)_m$$  (I)

wherein
m is 1 to 4;
Q is —$CH_2$—, —$C(HR^m)$—, or —$C(R^m R^m)$—;
each Z is independently —$CH_2$—, —O—, —$C(=O)$—, —$C(HR^m)$—, or —$C(R^m R^m)$—; and each $R^m$ is i) —$(C_1-C_5)$alkyl optionally substituted with hydroxyl, —$(C_1-C_3)$alkoxy or —O—$(C_1-C_3)$alkenyl, or ii) —$(C_1-C_5)$alkenyl.

An 18$^{th}$ embodiment of the present invention is a method comprising polymerizing a cyclic ester monomer with a catalyst under conditions suitable for ring-opening polymerization of the cyclic ester monomer, wherein the catalyst is as described in any one of the embodiments 6 to 10, or as in any one of the specific embodiments 1 to 9, provided that when the tridentate ligands $L^1$ and $L^2$ are represented by structural formula:

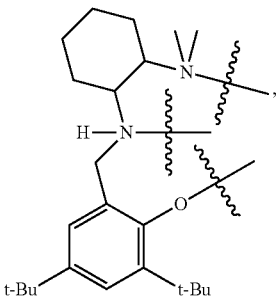

and the catalyst is represented by structural formula:

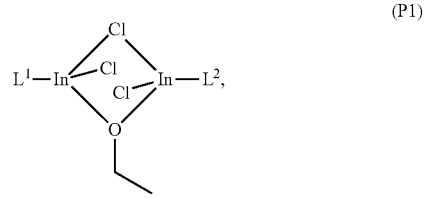

(P1)

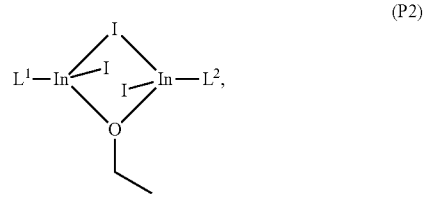

(P2)

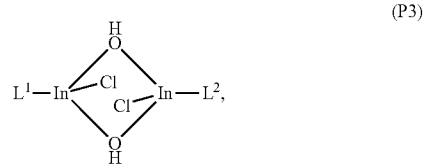

(P3)

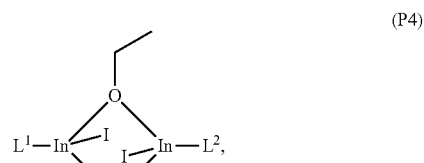

(P4)

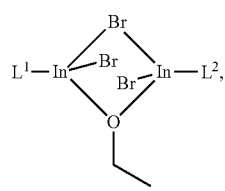 (P5)
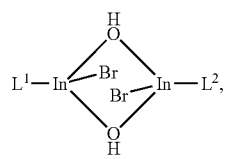 (P6)
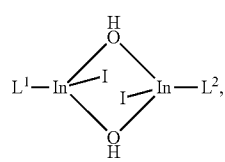 (P7)
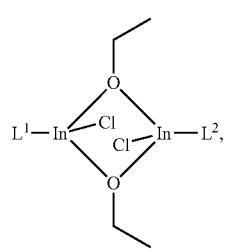 (P8)
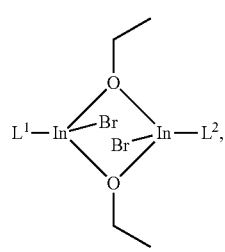 (P9)
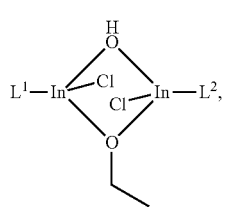 (P10)
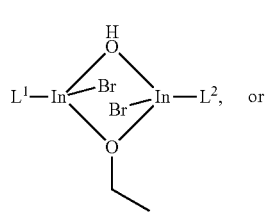 (P11) or
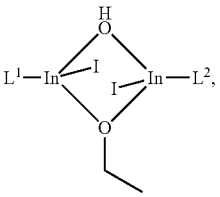 (P12)
then the cyclic ester monomer is not L-lactide, D-lactide, meso-lactide or rac-lactide.
The cyclic ester monomer is represented by structural formula:
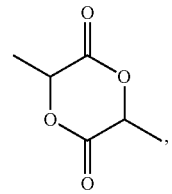 (IV)
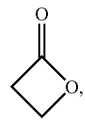 (V)
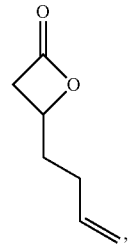 (VI)
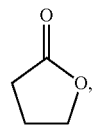 (VII)
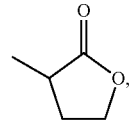 (VIII)
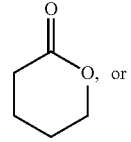 (IX)
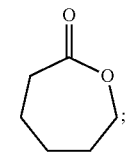 (X)
or a stereoisomer thereof.

Copolymerization Methods

A 19th embodiment of the present invention is a copolymerization method for preparing a block copolymer, comprising:
(a) polymerizing a first cyclic ester monomer with a catalyst under conditions suitable for ring-opening polymerization of the first cyclic ester monomer to form a first polymer block of the block copolymer; and
(b) polymerizing a second cyclic ester monomer, different from the first cyclic ester monomer, with a catalyst under conditions suitable for ring-opening polymerization of the second cyclic ester monomer to form a second polymer block of the block copolymer.

The catalyst for step (a) and (b) is independently as described in any one of the embodiments 6 to 10, or as in any one of the specific embodiments 1 to 9, and the first cyclic ester monomer and the second cyclic ester monomer are independently represented by structural formula (I):

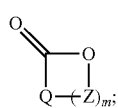
(I)

wherein
m is 1 to 4;
Q is —CH$_2$—, —C(HR$^m$)—, or —C(R$^m$R$^m$)—;
each Z is independently —CH$_2$—, —O—, —C(=O)—, —C(HR$^m$)—, or —C(R$^m$R$^m$)—; and
each R$^m$ is i) —(C$_1$-C$_5$)alkyl optionally substituted with hydroxyl, —(C$_1$-C$_3$)alkoxy or —O—(C$_1$-C$_3$)alkenyl, ii) —(C$_1$-C$_5$)alkenyl, or iii) (C$_1$-C$_5$)X$^m$ wherein X$^m$=F, Cl, Br, or I;
or a stereoisomer thereof;
provided that (i) no more than one Z is —O—, (ii) no more than one Z is —C(=O)—, (iii) at least one carbon ring atom is between any two oxygen ring atoms, (iv) at least one carbon ring atom is between any two —C(=O)— groups, and (v) at least one of any three consecutive ring members is —CH$_2$—, —C(HR$^m$)—, or —C(R$^m$R$^m$)—.

In a more particular embodiment, the cyclic ester monomer is represented by the following structural formula (I):

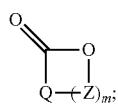
(I)

wherein
m is 1 to 4;
Q is —CH$_2$—, —C(HR$^m$)—, or —C(R$^m$R$^m$)—;
each Z is independently —CH$_2$—, —O—, —C(=O)—, —C(HR$^m$)—, or —C(R$^m$R$^m$)—; and
each R$^m$ is i) —(C$_1$-C$_5$)alkyl optionally substituted with hydroxyl, —(C$_1$-C$_3$)alkoxy or —O—(C$_1$-C$_3$)alkenyl, or ii) —(C$_1$-C$_5$)alkenyl.

A 20th embodiment of the present invention is a copolymerization method for preparing a block copolymer, comprising:
(a) polymerizing a first cyclic ester monomer with a catalyst under conditions suitable for ring-opening polymerization of the first cyclic ester monomer to form a first polymer block of the block copolymer; and
(b) polymerizing a second cyclic ester monomer, different from the first cyclic ester monomer, with a catalyst under conditions suitable for ring-opening polymerization of the second cyclic ester monomer to form a second polymer block of the block copolymer.

The catalyst for step (a) and (b) is independently as described in any one of the embodiments 6 to 10, or as in any one of the specific embodiments 1 to 9, and the first cyclic ester monomer and the second cyclic ester monomer are independently a di-lactone represented by structural formula (II) or a lactone represented by structural formula (III):

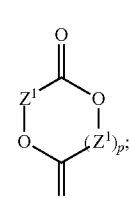
(II)

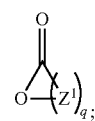
(III)

wherein
p is 1 or 2;
q is 2 to 5;
each Z$^1$ is independently —CH$_2$—, —C(HR$^m$)—, or —C(R$^m$R$^m$)—; and
each R$^m$ is i) —(C$_1$-C$_5$)alkyl optionally substituted with hydroxyl, —(C$_1$-C$_3$)alkoxy or —O—(C$_1$-C$_3$)alkenyl, ii) —(C$_1$-C$_5$)alkenyl, or iii) (C$_1$-C$_5$)X$^m$ wherein X$^m$=F, Cl, Br, or I;
or a stereoisomer thereof.

In a more particular embodiment, the cyclic ester monomer is represented by the following structural formula (I):

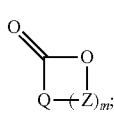
(I)

wherein
m is 1 to 4;
Q is —CH$_2$—, —C(HR$^m$)—, or —C(R$^m$R$^m$)—;
each Z is independently —CH$_2$—, —O—, —C(=O)—, —C(HR$^m$)—, or —C(R$^m$R$^m$)—; and
each R$^m$ is i) —(C$_1$-C$_5$)alkyl optionally substituted with hydroxyl, —(C$_1$-C$_3$)alkoxy or —O—(C$_1$-C$_3$)alkenyl, or ii) —(C$_1$-C$_5$)alkenyl.

A 21st embodiment of the present invention is a copolymerization method for preparing a block copolymer, comprising:
(a) polymerizing a first cyclic ester monomer with a catalyst under conditions suitable for ring-opening polymerization of the first cyclic ester monomer to form a first polymer block of the block copolymer; and
(b) polymerizing a second cyclic ester monomer, different from the first cyclic ester monomer, with a catalyst under conditions suitable for ring-opening polymerization of the second cyclic ester monomer to form a second polymer block of the block copolymer.

The catalyst for step (a) and (b) is independently as described in any one of the embodiments 6 to 10, or as in any one of the specific embodiments 1 to 9, and the first cyclic ester monomer and the second cyclic ester monomer are independently represented by structural formula:

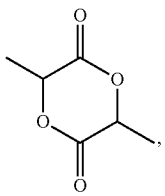
(IV)

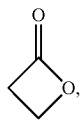
(V)

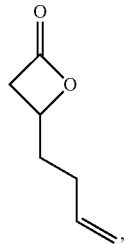
(VI)

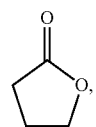
(VII)

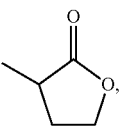
(VIII)

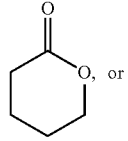
(IX)

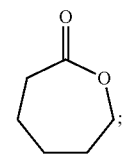
(X)

or a stereoisomer thereof.

A 22$^{nd}$ embodiment of the present invention is a copolymerization method for preparing a block copolymer, comprising:
(a) polymerizing a first cyclic ester monomer with a catalyst under conditions suitable for ring-opening polymerization of the first cyclic ester monomer to form a first polymer block of the block copolymer; and
(b) polymerizing a second cyclic ester monomer, different from the first cyclic ester monomer, with a catalyst under conditions suitable for ring-opening polymerization of the second cyclic ester monomer to form a second polymer block of the block copolymer.

The catalyst for step (a) and (b) is independently as described in any one of the embodiments 6 to 10, or as in any one of the specific embodiments 1 to 9, and the first cyclic ester monomer is lactide, D-lactide, L-lactide, meso-lactide, rac-lactide, β-butyrolactone, or 4-(but-3-en-1-yl)oxetan-2-one; and the second cyclic ester monomer is lactide, D-lactide, L-lactide, meso-lactide, rac-lactide, β-butyrolactone, or 4-(but-3-en-1-yl)oxetan-2-one.

A 23$^{rd}$ embodiment of the present invention is a copolymerization method as described in the 19$^{th}$ embodiment, further including
(c) polymerizing a third cyclic ester monomer, different from the first and second cyclic ester monomer, with a catalyst under conditions suitable for ring-opening polymerization of the third cyclic ester monomer to form a third polymer block of the block copolymer; and wherein the catalyst for step (c) is independently as described in any one of the embodiments 6 to 10, or as in any one of the specific embodiments 1 to 6.

A 24$^{th}$ embodiment of the present invention is a copolymerization method as described in the 20$^{th}$ embodiment, further including
(c) polymerizing a third cyclic ester monomer, different from the first and second cyclic ester monomer, with a catalyst under conditions suitable for ring-opening polymerization of the third cyclic ester monomer to form a third polymer block of the block copolymer; and wherein the catalyst for step (c) is independently as described in any one of the embodiments 6 to 10, or as in any one of the specific embodiments 1 to 6.

A 25$^{th}$ embodiment of the present invention is a copolymerization method as described in the 21$^{st}$ embodiment, further including
(c) polymerizing a third cyclic ester monomer, different from the first and second cyclic ester monomer, with a catalyst under conditions suitable for ring-opening polymerization of the third cyclic ester monomer to form a third polymer block of the block copolymer; and wherein the catalyst for step (c) is independently as described in any one of the embodiments 6 to 10, or as in any one of the specific embodiments 1 to 6.

A 26$^{th}$ embodiment of the present invention is a copolymerization method as described in the 23$^{rd}$ embodiment, further including
(c) polymerizing a third cyclic ester monomer, different from the first and second cyclic ester monomer, with a catalyst under conditions suitable for ring-opening polymerization of the third cyclic ester monomer to form a third polymer block of the block copolymer; and wherein the catalyst for step (c) is independently as described in any one of the embodiments 6 to 10, or as in any one of the specific embodiments 1 to 6.

A further embodiment of the present invention is a polymerization method of anyone of the preceding embodiments, wherein a high ratio of chain transfer agent to dinuclear Indium catalyst is provided. Typically the chain transfer agent is an alcohol, polyester or polyether. Suitable alcohols are RnOH, where Rn is any alkyl chain, including straight and branched alkyl chains. In one example, the alcohol is ethanol. In alternative examples, the alcohol is $HO(CH_2)_nOH$, $[HO(CH_2)_n]_3(CH)$ and $[HO(CH_2)_n]_4(C)$ as well as other star shaped multiols. Polyesters can also be used, such as, for example, (OH-terminated PLA) or $HO(CH_2O)_nOH$. A specific, non-limiting example of a suitable polyether is mPEG. A "high ratio" as referred to herein, typically, refers to a ratio that supports immortal polymerization. Typically, suitable ratios of chain transfer agent to dinuclear Indium catalyst are between about 1 and 1000, between about 1 and 500, between about 1 and 100, between about 1 and 50; between about 1 and 20; between about 1 and 10; or between about 1 and 4.

Polymers and Copolymers

Using the processes of the present invention as described in the previous section, polymers including copolymers, and particularly, block copolymers, can be prepared from cyclic ester monomers as described herein.

In the embodiments described herein, a polymer can be a homopolymer or a copolymer. Typically, the copolymers are block copolymers. More typically, the copolymers are di-block or tri-block copolymers.

In particular embodiments the polymer, and more particularly, block copolymer is a thermoplastic and biodegradable polymer.

A "homopolymer" as referred to herein, is a polymer that is prepared by the ring-opening polymerization of a single type of cyclic ester monomer, for example, D-lactide.

A "copolymer" as referred to herein, is a polymer that is prepared by the ring-opening polymerization of at least two different cyclic ester monomers. "Different" in this context requires that the cyclic ester monomers differ at least stereochemically, for example, one cyclic ester monomer can be L-lactide and the other D-lactide. For example, the ROP of lactide, or more particularly, a racemic mixture of L-lactide and R-lactide prepares a copolymer.

The catalysts as described herein can exhibit isoselectivity in the ROP of cyclic ester monomers leading to "iso-enriched" polymers or iso-enriched polymer blocks in a block copolymer.

An "iso-enriched" polymer as referred to herein, is a polymer, in which the polymer molecules exhibit on average more meso tetrads than racemo tetrads.

A measure to characterize the extent of iso-enrichment is $P_m$, that is, the conditional probability that a monomer insertion gives rise to the formation of a meso (Mmm) tetrad. Values for $P_m$ provided in the Examples described herein were experimentally obtained from NMR measurements using the ratios of peaks in the spectrum of the homonuclear decoupled proton NMR spectroscopy which shows peaks corresponding to different tetrads. In accordance with accepted literature data (JACS, 2002, 124, 1316) the ratio of the peaks indicated the Pm or probability of meso linkages in the polymers.

An "isotactic" polymer as referred to herein, is characterized by a $P_m$ value of about 1, that is, an isotactic polymer substantially only contains polymer molecules in which all structural units have the same orientation, for example, isotactic PLA:

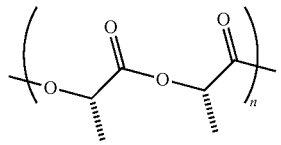

A "block copolymer" as referred to herein, is a copolymer that comprises at least two different polymer blocks. "Different" in this context requires that each polymer block is polymerized from a different cyclic ester monomers, wherein the cyclic ester monomers differ at least in their stereochemical composition, for example, a first polymer block can be prepared by ROP of L-lactide and a second polymer block can be prepared by ROP of a rac-lactide (i.e., racemic mixture of L-LA and D-LA).

Block copolymers that can be prepared from cyclic ester monomers using the catalysts and methods of the present invention include but are not limited to di-block copolymers and tri-block copolymers (e.g., A-B-C or A-B-A type), particularly, A-B-A tri-block type copolymers.

The polymers and polymer blocks of block copolymers prepared from a racemic cyclic ester monomer, can be iso-enriched, more particularly, they can be characterized by a $P_m$ value of more than about 0.5, more than about 0.53, or more than about 0.6; alternatively, polymers and polymer blocks of block copolymers of the present invention can be characterized by a $P_m$ value between 0.53 and 0.62.

Polymers and polymer blocks of block copolymers prepared from an enantiopure cyclic ester monomer can be isotactic. For example, isotactic PLA was prepared by ROP of L-LA using the methods of the present invention.

Also, typically, the polymers and block copolymers of the present invention are characterized by a polydispersity index of between 1.0 and 1.5, more typically, between 1.0 and 1.35, and even more typically, between 1.0 and 1.2.

Also, typically, the number average molecular weight of the polymers and block copolymers of the present invention is between about 10 kDa and 300 kDa.

"Polydispersity index (PDI)" as referred to herein, is calculated as the weight average molecular weight divided by the number average molecular weight of the polymer.

A description of embodiments of further embodiments of the present invention follows.

A $27^{th}$ embodiment of the present invention is a polymer prepared by the method as described in the $11^{th}$ embodiment.

A $28^{th}$ embodiment of the present invention is a polymer prepared by the method as described in the $12^{th}$ embodiment.

A $29^{th}$ embodiment of the present invention is a polymer prepared by the method as described in the $13^{th}$ embodiment.

A $30^{th}$ embodiment of the present invention is a polymer prepared by the method as described in the $14^{th}$ embodiment.

A $31^{st}$ embodiment of the present invention is a polymer prepared by the method as described in the $15^{th}$ embodiment.

A $32^{nd}$ embodiment of the present invention is a polymer prepared by the method as described in the $16^{th}$ embodiment.

A $33^{rd}$ embodiment of the present invention is a polymer prepared by the method as described in the $17^{th}$ embodiment.

A $34^{th}$ embodiment of the present invention is a polymer prepared by the method as described in the $18^{th}$ embodiment.

A $35^{th}$ embodiment of the present invention is a block copolymer prepared by the copolymerization method as described in the $19^{th}$ embodiment, wherein in step (a) a first polymer block of the block copolymer is prepared, and in step (b) a second polymer block of the block copolymer is prepared.

A $36^{th}$ embodiment of the present invention is a block copolymer prepared by the copolymerization method as described in the $20^{th}$ embodiment, wherein in step (a) a first polymer block of the block copolymer is prepared, and in step (b) a second polymer block of the block copolymer is prepared.

A $36^{th}$ embodiment of the present invention is a block copolymer prepared by the copolymerization method as described in the $21^{st}$ embodiment, wherein in step (a) a first polymer block of the block copolymer is prepared, and in step (b) a second polymer block of the block copolymer is prepared.

A $37^{th}$ embodiment of the present invention is a block copolymer prepared by the copolymerization method as described in the $22^{nd}$ embodiment, wherein in step (a) a first polymer block of the block copolymer is prepared, and in step (b) a second polymer block of the block copolymer is prepared.

A 38th embodiment of the present invention is a block copolymer prepared by the copolymerization method as described in the 23rd embodiment, wherein in step (a) a first polymer block of the block copolymer is prepared, in step (b) a second polymer block of the block copolymer is prepared, and in step (c) a third polymer block of the block copolymer is prepared.

A 39th embodiment of the present invention is a block copolymer prepared by the copolymerization method as described in the 24th embodiment, wherein in step (a) a first polymer block of the block copolymer is prepared, in step (b) a second polymer block of the block copolymer is prepared, and in step (c) a third polymer block of the block copolymer is prepared.

A 40th embodiment of the present invention is a block copolymer prepared by the copolymerization method as described in the 25th embodiment, wherein in step (a) a first polymer block of the block copolymer is prepared, in step (b) a second polymer block of the block copolymer is prepared, and in step (c) a third polymer block of the block copolymer is prepared.

A 41st embodiment of the present invention is a block copolymer prepared by the copolymerization method as described in the 26th embodiment, wherein in step (a) a first polymer block of the block copolymer is prepared, in step (b) a second polymer block of the block copolymer is prepared, and in step (c) a third polymer block of the block copolymer is prepared.

A 42nd embodiment of the present invention is a polymer or block copolymer composition of any one of the polymers or copolymers described in the preceding embodiments, in which the polymer or copolymer, respectively, is at least 80%, more typically, is at least 85%, and even more typically, is at least 90% pure by weight.

Further Definitions

"Alkyl" means an optionally substituted saturated aliphatic branched or straight-chain monovalent hydrocarbon radical having the specified number of carbon atoms. Thus, "$(C_1-C_6)$ alkyl" means a radical having from 1-6 carbon atoms in a linear or branched arrangement. "$(C_1-C_6)$alkyl" includes methyl, ethyl, propyl, butyl, pentyl and hexyl. Further, each of the listed alkyls includes the branched-chain monovalent hydrocarbon, e.g., butyl includes n-butyl, sec-butyl, iso-butyl and tert-butyl.

"Cycloalkyl" means a saturated aliphatic cyclic hydrocarbon ring. Thus, "$C_3-C_7$ cycloalkyl" means a hydrocarbon radical of a (3-7 membered) saturated aliphatic cyclic hydrocarbon ring. A $C_3-C_7$ cycloalkyl includes, but is not limited to cyclopropyl, cyclobutyl, cyclopentyl, cyclohexyl and cycloheptyl.

"Alkenyl" as used herein refers to a hydrocarbon backbone radical, having the number of carbon atoms falling within the specified range. For example, $(C_2-C_3)$alkenyl means that a hydrocarbon radical is attached that may contain anywhere from 2 to 3 carbon atoms with the remaining valence filled in by hydrogen atoms unless specified otherwise. The term also includes each permutation as though it were separately listed. Thus, $(C_2-C_3)$alkenyl includes ethenyl, 1-propenyl and 2-propenyl.

Examples and Experimental Section

A description of example embodiments of the invention follows.

The teachings of all patents, published applications and references cited herein are incorporated by reference in their entirety.

Catalyst Synthesis

The dinuclear indium catalysts of the present invention can be synthesized using the methods and methods analogous to the ones described below.

The formula "$[(NN_{R3}O_{R4})InX]_2(\mu-Y^2)(\mu-Y^1)$" as used herein, denotes catalysts represented by structural formula (A) in which both tridentate ligands are represented by the following structural formula:

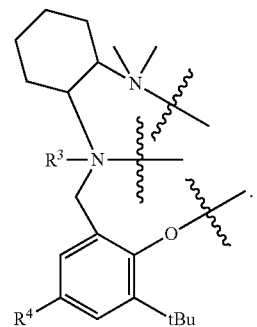

If $Y^1$ and $Y^2$ are the same, the formula can shortened to "$[(NN_{R3}O_{R4})InX]_2(\mu-Y^2)_2$". The formula "$[(^{TH}—NN_{R3}O_{R4})InX]_2(\mu-Y^2)(\mu-Y^1)$" as used herein, denotes catalysts represented by structural formula (A) in which both tridentate ligands are represented by the following structural formula:

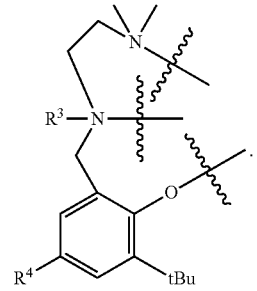

If "$NNO_{R4}$" is recited, $R^3$ is H unless it is clear from the context that $R^3$ is not H.

The following Table provides an overview of exemplary dinuclear indium catalysts suitable for the ring opening polymerization of cyclic ester monomers:

| Example | |
|---|---|
| Example 1 | $[(NN_HO_{tBu})InBr]_2(\mu-Br)(\mu-OEt)$ |
| Example 2 | $[(NN_HO_{tBu})InI]_2(\mu-I)(\mu-OEt)$ |
| Example 3 | $[(NN_HO_{tBu})InI(\mu-OH)]_2$ |
| Example A4 | $[(NN_HO_{Me})InCl]_2(\mu-Cl)(\mu-OEt)$ |
| Example A5 | $[(NN_HO_{Me})InI]_2(\mu-I)(\mu-OEt)$, and $[(NN_HO_{Me})InI]_2(\mu-OEt)_2$ |
| Example B2 | $[(NN_HO_{Me})InI]_2(\mu-OEt)_2$ |
| Example B3 | $[(NN_HO_{tBu})InI]_2(\mu-OEt)_2$ |
| Example B4 | $[(NN_HO_{tBu})InI]_2(\mu-OEt)_2$ |
| Example C1 | $[(NN_HO_{tBu})InI]_2(\mu-OH)(\mu-OEt)$ |
| Example C2 | $[(NN_HO_{Me})InI]_2(\mu-OH)(\mu-OEt)$ |
| Example D | $[(^{TH}-NN_{Me}O_{tBu})InCl]_2(\mu-Cl)(\mu-OEt)$, and $[(^{TH}-NN_{Me}O_{Me})InCl]_2(\mu-Cl)(\mu-OEt)$ |
| Example E | $[(NN_{Me}O_{tBu})In(Cl)]_2(\mu-Cl)(\mu-OEt)$ |

EXAMPLES

Unless otherwise indicated, all air and/or water-sensitive reactions were carried out under dry nitrogen using either an MBraun glovebox or standard Schlenk line techniques. NMR spectra were recorded on a Bruker Avance 400.

MHz spectrometer. 1H NMR chemical shifts are reported in ppm versus residual protons in deuterated solvents as follows: δ 7.27 CDCl$_3$, δ 7.16 C$_6$D$_6$, δ 5.32 CD$_2$Cl$_2$.

$^{13}$C {$^1$H} NMR chemical shifts are reported in ppm versus residual $^{13}$C in solvents as follows: δ 77.2 CDCl$_3$, δ 128.4 C$_6$D$_6$, δ 54.0 CD$_2$Cl$_2$. Diffraction measurements for X-ray crystallography were made on a Bruker X8 APEX II diffractometer with graphite-monochromated Mo Kα radiation.

Solvents (pentane, THF, toluene, dichloromethane, and diethyl ether) were degassed and dried using 3 Å molecular sieves in an MBraun Solvent Purification System. THF was further dried over sodium benzophenone ketyl and distilled under N$_2$. CD$_2$Cl$_2$ and CDCl$_3$ were dried over CaH$_2$ and degassed through a series of freeze-pump-thaw cycles. C$_6$D$_6$ was dried over sodium and degassed using a series of freeze-pump-thaw cycles. InCl$_3$, InBr$_3$, InI$_3$, and In(Me)$_3$ were purchased from Strem Chemicals and used without further purification. For the enantiopure catalyst, (±)-trans-1,2-diaminocyclohexane was resolved using Jacobsen's method (Larrow, J. F.; Jacobsen, E. N.; Gao, Y.; Hong, Y. P.; Nie, X. Y.; Zepp, C. M., *J. Org. Chem.* 1994, 59, 1939-1942) and then carried forward through the same procedures as used for the rac-catalyst. Benzyl potassium was synthesized using a modified literature procedure using n-butyllithium (Aldrich), potassium tert-butoxide (Alfa Aesar), and toluene (Schlosse, M.; Hartmann, *J. Angew. Chem., Int. Ed. Engl.* 1973, 12, 508-509). All other compounds were obtained from Aldrich and used without further purification. The literature preparation of H$_2$NN$_H$O (Mitchell, J. M.; Finney, N. S. *Tetrahedron Lett.* 2000, 41, 8431-8434) was modified as follows: the imine was recrystallized from warm acetonitrile, and the proligand was recrystallized from acetonitrile when it was formed. K(NN$_H$O) was prepared according to procedures described in Labourdette, G.; Lee, D. J.; Patrick, B. O.; Ezhova, M. B.; Mehrkhodavandi, P. *Organometallics* 2009, 28, 1309-1319.

Example 1

Synthesis of catalyst complex [(NN$_H$O$_{tBu}$)InBr]$_2$(μ-Br)(μ-OEt)

Synthesis of (NN$_H$O$_{tBu}$)InBr$_2$: A solution of K(NN$_H$O) (0.112 g, 0.29 mmol) in 5 mL of THF was added dropwise to a solution of InBr3 (0.105 g, 0.29 mmol) in 5 mL of THF. The reaction was stirred at room temperature for 2 h, and the formation of KBr was observed. The salt was removed by filtration through glassfilter paper, the remaining yellow-orange solution was evaporated to dryness, and the residue was dried 2 h in vacuo. Complex (NN$_H$O$_{tBu}$)InBr$_2$ was obtained as a yellow crystalline solid (0.155 g; 83% yield). Suitable crystals for X-ray diffraction were grown by slow diffusion of pentane in a CH2Cl2 solution of the complex, (NN$_H$O$_{tBu}$)InBr$_2$. $^1$H NMR (400 MHz, CD$_2$Cl$_2$): δ 7.27 (1H, d, J=3 Hz, ArH), 6.88 (1H, d, J=3 Hz, ArH), 4.15 (1H, triplet, R$_2$N—CH—CH$_2$), 4.06 (1H, d, J=12 Hz, NH—CH$_2$—Ar), 2.71 (3H, s, N(Me)(Me)), 2.60 (2H, m, CHNH and CHNMe$_2$), 2.48 (3H, s, N(Me)(Me)), 1.95 (6H, —CH$_2$— of DACH), 1.43 (9H, s, t-Bu), 1.28 (11H, s, t-Bu and m, CH$_2$ of DACH). $^{13}$C {$^1$H} NMR (100.64 MHz, CD$_2$Cl$_2$): δ 163.5, 138.2, 136.8, 126.2, 125.9, 118.8, 53.4, 51.2, 38.3, 36.0, 34.5, 32.5, 31.7, 31.2, 30.4, 24.8, 24.7, 22.2, 27.7. EI-LRMS (m/z) [M+] 634. Anal. Calcd (found) for C$_{25}$H$_{39}$Br$_2$—InN$_2$O: C, 47.30 (47.29); H, 6.15 (6.13); N, 4.42 (4.41) (note: DACH is diaminocyclohexane).

Synthesis of {[(NN$_H$O$_{tBu}$)InBr]$_2$(μ-Br)(μ-OEt)}: A 25 mL round-bottom flask was charged with complex (NN$_H$O$_{tBu}$)InBr$_2$ (0.100 g, 0.16 mmol) dissolved in 5mL of toluene. A solution of NaOEt (0.011 g, 0.16 mmol) in 5 mL of toluene was added dropwise to this mixture. After stirring the reaction mixture for 2 h at room temperature, NaBr formation was observed. The salt was removed by filtration through glass filter paper, and the remaining yellow solution was evaporated to dryness. The residue was washed with pentane and dried for 2 h in vacuo to yield the {[(NN$_H$O$_{tBu}$)InBr]2(μ-Br)(μ-OEt)} complex as a white powder (0.071 g, 70% yield). $^1$H NMR (400 MHz, CD$_2$Cl$_2$): δ 7.20 (1H, d, J=4 Hz, ArH), 6.80 (1H, d, J=3 Hz, ArH), 4.81 (1H, d, J=12 Hz, HN—CHH—Ar), 4.40 (m, 1H, OCHHMe), 4.19 (1H, m, OCHHMe), 3.72 (1H, d, J=12 Hz, NH—CHHAr), 2.55 (3H, s, NMeMe), 2.48 (2H, m, CHN(Me)$_2$ and CHNH), 1.89 (3H, s, NMeMe), 1.85 (4H, in, —CH$_2$— of DACH), 1.43 (9H, s, t-Bu), 1.41 (2H, t J=8 Hz, OCH$_2$CH$_3$), 1.27 (11H, s, t-Bu and m, —CH$_2$— of DACH), 1.07 (2H, m, —CH$_2$— of DACH). $^{13}$C{$^1$H} NMR (100.64 MHz, CD$_2$Cl$_2$): δ 163.3, 138.7, 136.7, 129.5, 125.8, 120.0, 67.4, 61.2, 50.6, 45.7, 38.1, 35.8, 34.3, 32.1, 30.3, 26.4, 25.4, 25.3, 22.4, 19.9. EI-LRMS (m/z): 554 (M$^+$ —In(NNO)(Br)$_2$(OEt)), 634 (M$^+$) —In—(NNO)Br(OEt)). Anal. Calcd (found) for C$_{48}$H$_{83}$Br$_3$In$_2$N$_4$O$_3$: C, 46.70 (46.72); N, 4.50 (4.34); H, 6.70 (6.69).

Example 2

Synthesis of Catalyst Complex [(NN$_H$O$_{tBu}$)InI]$_2$(μ-OEt)

Synthesis of (NN$_H$O$_{tBu}$)InI$_2$: A similar procedure to that for complex (NN$_H$O$_{tBu}$)InBr$_2$ (see Example 1) was used using InI$_3$ (0.171 g, 0.34 mmol) and KNN$_H$O$_{tBu}$ (0.130 g, 0.34 mmol). The reaction was stirred at room temperature for 2 h, and then KI formation was observed. The salt was removed by filtration through glass filter paper, and the remaining yellow solution was evaporated to dryness. (NN$_H$O$_{tBu}$)InI$_2$ was obtained as a yellow powder (0.235 g; 95% yield). $^1$NMR (400 MHz, CD$_2$Cl$_2$): δ 7.26 (1H, d, J=3 Hz, ArH), 6.88 (1H, d, J=3 Hz, ArH), 4.13 (1H, t, J=12 Hz, R$_2$N—CH—CH$_2$), 3.97 (1H, d, J=15 Hz, NH—CH$_2$—Ar), 2.78 (2H, m,NCH of DACH), 2.62 (3H, s, NMeMe), 2.46, (3H, s, NMeMe), 1.91 (4H, m, —CH$_2$— of DACH), 1.44 (9H, s, t-Bu), 1,33 (2H, in, —CH$_2$— of DACH), 1.28 (9H, s, t-Bu), 1.27 (2H, m, —CH$_2$— of DACH. $^{13}$C {$^1$H} NMR (100.64 MHz, CD$_2$Cl$_2$): δ 163.5, 139.9, 136.9, 126.0, 125.9, 118.8, 53.5, 51.2, 38.5, 36.2, 34.5, 32.5, 31.8, 31.3, 30.6, 24.9, 24.8, 22.1, 21.8. EI-LRMS (m/z) [M$^+$]: 728. Anal. Calcd (found) for C$_{25}$H$_{39}$I$_2$InN$_2$O: C, 41.20 41.15); H, 5.36 (5.35); N, 3.84 (3.81).

Synthesis of {[(NN$_H$O$_{tBu}$)InI]$_2$(μ-OEt)}: The same procedure to prepare {[(NN$_H$O$_{tBu}$)InBr]$_2$(μ-Br)(μ-OEt)} in Example 1 was followed using (NN$_H$O$_{tBu}$)InI$_2$ (0.080 g, 0.11 mmol) dissolved in 5 mL of toluene and NaOEt (0.008 g, 0.11 mmol) in 5 mL of toluene. The reaction was stirred at room temperature for 12 h, and then NaI formation was observed. The salt was eliminated by filtration through glass filter paper, and the yellow solution was evaporated to dryness. The residue was washed with pentane, and {[(NN$_H$O$_{tBu}$)InI]$_2$(μ-I)(μ-OEt)} was obtained as a white powder, which was dried for 2 h in vacuo (0.051 mg; 68% yield). 1H NMR (400 MHz, CD$_2$Cl$_2$): δ 7.22 (1H, J=4 Hz, ArH), 6.80 (1H, d, J=3 Hz, ArH), 4.84 (1H, d, J=12 Hz, HN—CHH—Ar), 4.40 m, 1H, OCHHMe). 4.21 (1H, m, OCHHMe), 3.75 (1H, d, J=12 Hz, NH—CHH—Ar), 3.43 (1H, d, J=12 Hz, CHNH), 2.66 (2H, m, —CH$_2$— of DACH), 2.56 (3H, s, NMeMe), 2.48, (1H, m, CHN(Me)$_2$), 1.92 (3H, s, NMeMe), 1.83 (2H, m, —CH$_2$— of DACH), 1.44 (9H, s, t-Bu), 1.41 (2H, t J=8 Hz, OCH$_2$CH$_3$), 1.28 (11H, s, t-Bu and m, —CH$_2$— of DACH), 1.14 (2H, m, —CH$_2$— of DACH). $^{13}$C{$^1$H} NMR (100.64 MHz, CD$_2$Cl$_2$): δ 163.2, 138.9, 136.7, 126.8, 124.5, 119.9, 67.3, 62.0, 50.3, 46.0, 38.1, 35.7, 34.3, 32.2, 30.3, 26.2, 25.5, 26.3, 22.7, 19.6. EI-LRMS (m/z) 602 (M$^+$ —In(NNO)(I)$_2$(OEt)), 728 (M$^+$ —In(NNO)I—(OEt)). Anal. Calcd (found) for C$_{48}$H$_{83}$I$_3$In$_2$N$_4$O$_3$: C, 41.91 (41.92); H, 6.03 (6.05); N, 4.10 (4.12).

Example 3

Synthesis of Catalyst Complex [(NN$_H$O$_{tBu}$)InI(µ-OH)]$_2$

[(NN$_H$O$_{tBu}$)InI(µ-OH)]$_2$: {[(NN$_H$O$_{tBu}$)InI]$_2$(µ-I)(µ-OEt)} as prepared in Example 2 was removed from the inert atmosphere and exposed to moist air for 24 h, to yield the air- and moisture-stable µ-OH dinuclear complex [(NN$_H$O$_{tBu}$)InI(µ-OH)]$_2$ in quantitative yield. Suitable crystals for X-ray diffraction were grown by slow diffusion of Et$_2$O in a CH$_2$Cl$_2$ solution of [(NN$_H$O$_{tBu}$)InI(µ-OH)]$_2$. $^1$H NMR(300 MHz, CDCl$_3$): δ 7.23 (1H, d, J=3 Hz, Ar), 6.78 (1H, d, J=3 Hz, Ar), 4.77 (1H, d, J=15 Hz, NCHHAr), 3.87 (1H, b, OH), 3.73 (1H, d, J=6 Hz,NCHHAr), 3.37 (1H, d, J=9 Hz, CHNH), 2.68 (1H, m CHNMe2), 2.54 (3H, s, NMeMe) 2.20 (3H, m, CH$_2$ of DACH), 1.93 (3H, s, NMeMe), 1.81 (2H, m, CH$_2$ of DACH), 1.58 (2H, m, CH$_2$ of DACH), 1.47 (9H, s, t-Bu), 1.27 (9H, s, t-Bu), 1.08 (2H, m, CH$_2$ of DACH). $^{13}$C{$^1$H} NMR (100 MHz, CDCl$_3$): δ 164.2, 139.8, 137.8, 127.3, 125.1, 121.2, 65.9, 53.1, 51.9, 51.2, 44.3, 38.7, 36.2, 34.9, 32.7, 31.6, 31.4, 31.2, 25.5, 25.4, 22.1. Anal. Calcd (found) for C$_{54}$H$_{100}$N$_4$—O$_6$In$_2$I$_2$: C, 46.70 (46.32); H, 7.19 (7.18), N, 4.10 (4.11).

Example A

Synthesis of Dinuclear Indium Complexes of the Type [(NN$_H$O$_R$)InX]$_2$(µ-X)(µ-OEt)

Scheme 1.

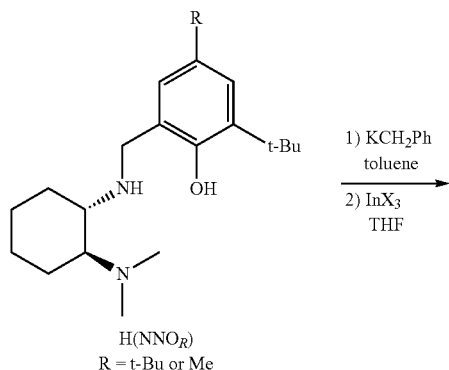

H(NNO$_R$)
R = t-Bu or Me

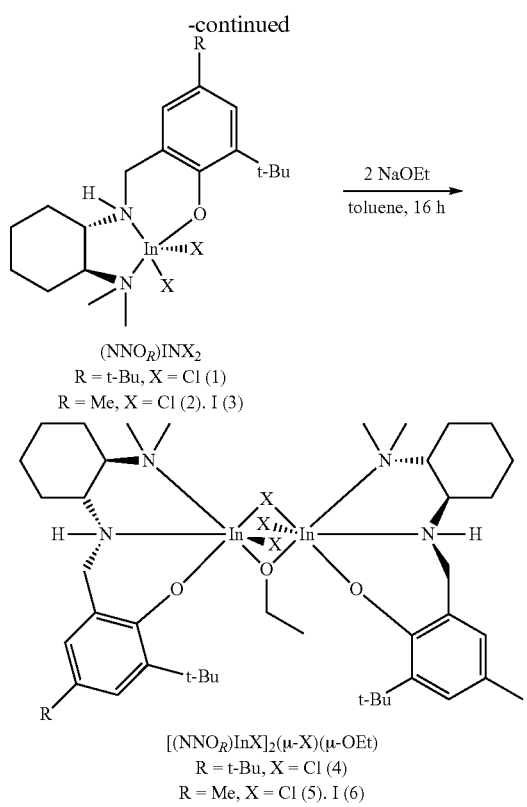

(NNO$_R$)InX$_2$
R = t-Bu, X = Cl (1)
R = Me, X = Cl (2). I (3)

[(NNO$_R$)InX]$_2$(µ-X)(µ-OEt)
R = t-Bu, X = Cl (4)
R = Me, X = Cl (5). I (6)

The chiral diaminophenol proligands H(NN$_H$O$_R$) where R is a para-methyl or t-butyl substituent on the phenol group were synthesized according to the method described in Douglas et al., Angew. Chem. Int. Ed. 2008, 47, 2290-2293. Dihalide complexes bearing these ligands, (NN$_H$O$_R$)InX$_2$ (X=Cl (1)) and (NN$_H$O$_{Me}$)InX$_2$ (X=Cl (2), I (3)), were prepared by addition of the potassium salts of the ligands to the appropriate indium trihalide. Both, racemic and enantiopure H(NNO$_R$) can be used in the syntheses described below. Addition of 2 equiv NaOEt to complexes 1-3, forms the mixed bridge alkoxy-halide complexes [(NN$_H$O$_{tBu}$)InX]$_2$(µ-X)(µ-OEt) (X=Cl (4)) and [(NN$_H$O$_{Me}$)InX]$_2$(µ-X)(µ-OEt) (X=Cl (5), I (6)).

Example A1

Synthesis of 6-tert-butyl-2-{N-[2-(N,N-dimethyl)aminocyclohexyl]salicaldimino}-4-methylphenol (H$_2$NN$_H$O$_{Me}$)

The H$_2$NN$_H$O$_{Me}$ proligand was synthesized according to the method described in Douglas et al., Angew. Chem. Int. Ed. 2008, 47, 2290-2293. (78% yield after recrystallization in acetonitrile). $^1$H NMR (300 MHz, CD$_2$Cl$_2$): δ 6.98 (1H, d, J=3 Hz, ArH), 6.70 (1H, d, J=3 Hz, Ara), 3.98 (1H, d, J=12Hz, NH—CH$_2$—Ar), 3.78 (1H, d, J=12 Hz, NH—CH$_2$—Ar), 3.51 (1H, br. s., —NH—), 2.40-2.30 (1H, m, N—CH—CH$_2$ of DACH), 2.25 (3H, s, Ar—CH$_3$), 2.20 (6H, s, —N—(CH$_3$)$_2$) 1.83-1.80 (2H, m, N—CH—CH$_2$ and —CH$_2$— of DACH), 1.71-1.60 (1H, m, —CH$_2$— of DACH), 1.42 (9H, Ar—(CH$_3$)$_3$), 1.24-1.11 (4H, m, —CH$_2$— of DACH).

Example A2

Synthesis of [(NN$_H$O$_{Me}$)InCl$_2$]

A suspension of InCl$_3$ (239 mg, 1.08 mmol) in THF (3 ml) was added dropwise to a slurry solution of KHNN$_H$O in THF (10 ml), which was produced by reacting the equimolar amount of H$_2$NN$_H$O$_{Me}$ (309 mg, 0.97 mmol) and benzylpotassium (126 mg, 0.97 mmol) in Toluene (30 ml). The mixture was stirred for 12 h at room temperature. A white solid was filtered through Celite. The pale yellow filtrate was concentrated under vacuum. An off-white solid was precipitated out of solution by adding ether (5 ml) to the concentrated filtrate. The desired product was obtained on a glass frit and dried in vacuo for few hours. Recrystallization with a mixture solution of THF and ether at room temperature afforded yellow crystals. (380 mg, 76%) $^1$H NMR (400 MHz, CD$_2$Cl$_2$): δ 7.04 (1H, d, J=2.0 Hz, ArH), 6.68 (1H, d, J=1.7 Hz, ArH), 4.46 (1H, d, J=12.6 Hz, NH—CH$_2$—Ar), 3.97 (1H, dd, J=12.5, 6.7 Hz, NH—CH$_2$—Ar), 2.73-2.82 (1H, m, N—CH—CH$_2$ of DACH), 2.71 (3H, s, Ar—CH$_3$), 2.63-2.61 (1H, m, N—CH—CH$_2$ of DACH), 2.54 (1H, br. s., —CH$_2$— of DACH), 2.38-2.48 (1H, m, —CH$_2$— of DACH), 2.27 (3H, s, —N—(CH$_3$)$_2$), 2.21 (3H, s, Ar—CH$_3$), 1.94-2.04 (m, 1H, —CH$_2$— of DACH), 1.78-1.94 (2H, in, —CH$_2$— of DACH), 1.40 (9H, Ar—(CH$_3$)$_3$), 1.18-1.29 (3H, m, —CH$_2$— of DACH); $^{13}$C {$^1$H} NMR (101 MHz, CD$_2$Cl$_2$) 6 Anal. Calcd. For C$_{20}$H$_{33}$Cl$_2$InN$_2$O: C 47.74; H 6.61; N 5.57. Found: C 47.48; H 6.60; N 5.51.

Example A3

Synthesis of [(NN$_H$O$_{Me}$)InI$_2$]

A suspension of InI$_3$ (973 mg, 1.96 mmol) in THF (3 ml) was added dropwise to a slurry solution of KHNN$_H$O$_{Me}$ (700 mg, 1.96 mmol) in THF (20 ml), which was produced by reacting the equimolar amount of H$_2$NN$_H$O$_{Me}$ and benzylpotassium in toluene. The mixture was stirred for 12 h at room temperature. A white solid was filtered through Celite. The pale yellow filtrate was concentrated under vacuum. An off-white solid was precipitated out of solution by adding ether (10 ml) to the concentrated filtrate. The desired product was obtained on a glass frit and dried in vacuo for few hours. (965 mg, 72%)

Example A4

Synthesis of [(NN$_H$O$_{Me}$)InCl]$_2$(μ-Cl)(μ-OEt)

A solution of NaOEt (20 mg, 0.30 mmol) in toluene (1.5 ml) was added dropwise to a stirring suspension of [(NN$_H$O$_{Me}$)InCl$_2$] (150 mg, 0.30 mmol) in toluene (3 ml) at room temperature. The reaction mixture was stirred for 12 h. The white precipitate was filtered through Celite, to collect the pale yellow filtrate. All volatiles were removed in vacuo, and ether (5 ml) was added to the residue. The desired off-white solid was precipitated out of solution. The product was collected on a glass frit and dried in vacuo for few hours (140.8 mg, 93%). $^1$H NMR (400 MHz, CD$_2$Cl$_2$): δ 6.99 (1H, br. s., 6.60 (1H, br. s., ArH), 4.91 (1H, d, J=13.5 Hz, NH—CH$_2$—Ar), 4.25-4.45 (1 H, m, O—CH$_2$—CH$_3$), 3.72 (1H, dd, J=1.7, 13.6 Hz, NH—CH$_2$—Ar), 2.86 (1H, td, J=3.1, 11.3 Hz, N—CH—CH$_2$), 2.73-2.74 (1H, br. m, —CH$_2$— of DACH), 2.66 (3H, s, —N(CH$_3$)$_2$), 2.52-2.63 (1H, m, N—CH—CH$_2$), 2.48-2.50 (1H, m, —CH$_2$— of DACH), 2.18 (3H, s, Ar—CH$_3$), 2.03 (3H, s, —N(CH$_3$)$_2$), 1.86-1.99 (1H, m, —CH$_2$— of DACH), 1.82 (1H, br. m, —CH$_2$— of DACH), 1.39 9H, Ar—(CH$_3$)$_3$), 1.01-1.31 (6H, m, —CH$_2$— of DACH and O—CH$_2$—CH$_3$); $^{13}$C{$^1$H} NMR (101 MHz, CD$_2$Cl$_2$) δ 163.2 (Ar C), 139.9 (Ar C), 130.6 (Ar C—H), 128.6 (Ar C—H), 123.3 (Ar C), 120.0 (Ar C), 65.3 (N—CH$_2$—Ar), 63.0 (O—CH$_2$—CH$_3$), 53.2 (N—CH—CH$_2$), 50.8 (N—CH—CH$_2$), 44.6 (N(CH$_3$)$_2$), 38.5 (N(CH$_3$)$_2$), 35.5 (Ar—C(CH$_3$)$_3$), 31.5 (Ar—CH$_3$), 30.2 (Ar—C(CH$_3$)$_3$), 25.4 (—CH$_2$— of DACH), 25.2 (—CH$_2$— of DACH), 22.4 (—CH$_2$— of DACH), 20.9 (—CH$_2$— of DACH), 19.8 (O—CH$_2$—CH$_3$).

Example A5

Synthesis of [(NN$_H$O$_{Me}$)InI]$_2$(μ-I)(μ-OEt) and [(NN$_H$O$_{Me}$)InI]$_2$(μ-OEt)$_2$

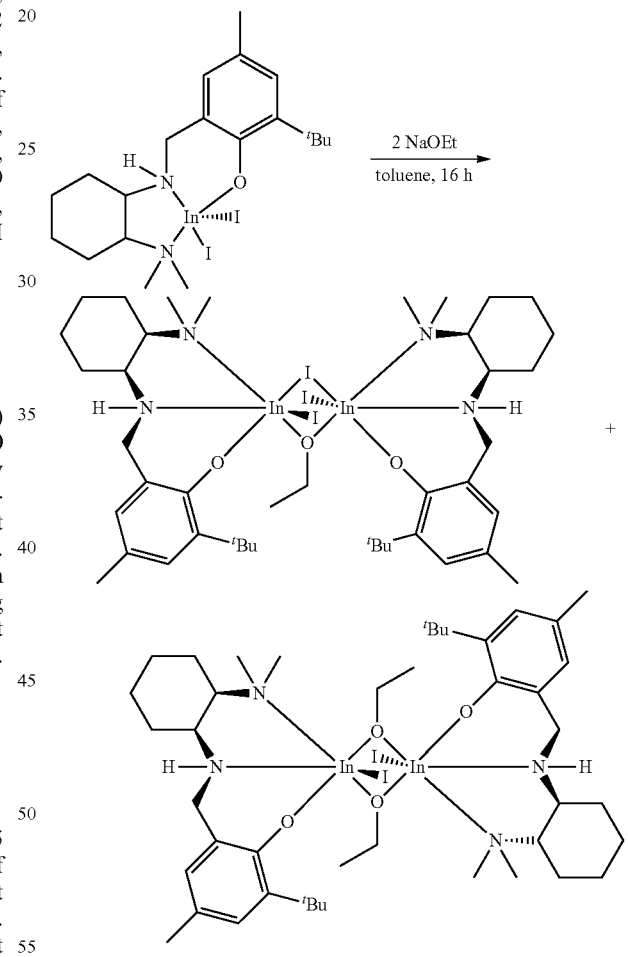

Two equivalents of NaOEt (61.3 mg, 0.90 mmol) in toluene (6 ml) were added dropwise to a stirring suspension of [(NN$_H$O$_{Me}$)InI$_2$] (309.4 mg, 0.45 mmol) in toluene (8 ml) at room temperature after both of the solutions were stirred for 5 minutes separately. The reaction mixture was stirred for 16 h. The white precipitate was filtered through a glass filter paper, to collect the pale yellow filtrate. All volatiles were removed in vacu. A THF solvent (ca. 2m1) was added to the residue, and acetonitrile (ca. 5 ml) was added to separate [(NN$_H$O$_{Me}$)InI]$_2$(μ-I)(μ-OEt) and [(NN$_H$ O$_{Me}$)InI]$_2$(μ-OEt)$_2$. The solution was filtered through a fine frit to collect the filtrate for [(NN$_H$O$_{Me}$)InI]$_2$(µ-I)(µ-OEt), and the white solid for [(NN$_H$O$_{Me}$)InI]$_2$(µ-OEt)$_2$. The solvent from the collected filtrate was removed under vacuum and washed with acetonitrile (2×1 ml). The off-white solid was dried under vacuum to obtain [(NN$_H$O$_{Me}$)InI]$_2$(µ-I)(µ-OEt). ([(NN$_H$O$_{Me}$)InI]$_2$(µ-I)(µ-OEt): 100.5 mg, 35% yield; complex 7: 39.5 mg, 14% yield) $^1$H NMR (400 MHz, CD$_2$Cl$_2$): δ 7.00 (1H, d, J=1.9 Hz, ArH), 6.63 (1H, d, J=1.9 Hz, ArH), 4.79-4.86 (1H, m, NH—CH$_2$—Ar), 4.15-4.41 (1 H, m, O—CH$_2$—CH$_3$), 3.65-3.77 (1H, m, NH—CH$_2$—Ar), 3.41 (1H, d, J=10.8 Hz, N—CH—CH$_2$), 2.60-2.72 (1H, m, N—CH—CH$_2$), 2.57 (3H, s, —N(CH$_3$)$_2$), 2.51-2.55 (1H, m, —CH$_2$— of DACH), 2.46 (1H, td, J=3.2, 11.4 Hz, —CH$_2$— of DACH), 2.20 (3H, s, Ar—CH$_3$), 1.96 (3H, s, —N(CH$_3$)$_2$), 1.84 (1H, t, J=12.1 Hz, —CH$_2$— of DACH), 1.43 (9H, Ar—(CH$_3$)$_3$), 1.37 (2H, t, J=12.1 Hz, O—CH$_2$—CH$_3$), 1.05-1.33 (4H, m, —CH$_2$— of DACH); $^{13}$C{$^1$H} NMR (101 MHz, CD$_2$Cl$_2$) δ 63.4 (Ar C), 139.7 (Ar C), 130.5 (Ar C—H), 128.4 Ar C—H), 122.9 (Ar C), 120.3 (Ar C), 67.4 (N—CH$_2$—Ar), 61.9 (O—CH$_2$—CH$_3$), 53.2 (N—CH—CH$_2$), 50.0 (N—CH—CH$_2$), 46.0 (N(CH$_3$)$_2$), 38.1 (N(CH$_3$)$_2$), 35.3 (Ar—C(CH$_3$)$_3$), 31.2 (Ar—CH$_3$), 30.4 (Ar—C(CH$_3$)$_3$), 25.4 (—CH$_2$— of DACH), 25.2 (—CH$_2$— of DACH), 22.6 (—CH$_2$— of DACH), 20.9 (—CH$_2$— of DACH), 19.5 (O—CH$_2$—CH$_3$).

Example A6

Synthesis of [(NN$_H$O$_{Me}$)InBr]$_2$(µ-Br)(µ-OEt)

[(NN$_H$O$_{Me}$)InBr]$_2$(µ-Br)(µ-OEt) can be prepared similar to the methods described in Example 1 except that the [(NN$_H$O$_{Me}$)InBr$_2$] is used which can be prepared similar to the method of Example A2.

Examples B

Synthesis of Dinuclear Indium Complexes of the Type [(NN$_H$O$_R$)InX]$_2$(µ-OEt)$_2$ with R=Me or t-Bu and X=Cl, Br, or I Example B1

Synthesis of [(NN$_H$O$_{Me}$)InI]$_2$(µ-OEt)$_2$

The [(NN$_H$O$_{Me}$)InI]$_2$(µ-OEt)$_2$ complex was prepared as described in Example A5.

Example B2

Synthesis of [(NN$_H$O$_{Me}$)InI]$_2$(µ-OEt)$_2$

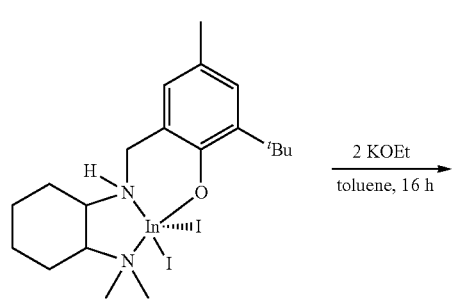

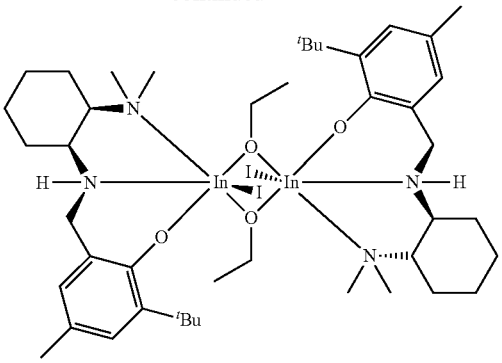

A suspension of KOEt (24.5 mg, 0.29 mmol) in toluene (4 ml) were added dropwise to a stirring suspension of racemic [(NN$_H$O$_{Me}$)InI$_2$] (100 mg, 0.14 mmol) in toluene (6 ml) at room temperature after both of the solutions were stirred for 5 minutes separately. As soon as the addition was finished, the pale yellow color of the reaction mixture was turned to white, and the white solid was filtered through a glass filter paper to collect the colorless filtrate. All volatiles were removed in vacuo to dryness. A THF solvent (ca. 1ml) was added to the residue, and acetonitrile (ca. 2 ml) was added to precipitate a white solid out of solution. The solution was decanted off, and the solid was washed with acetonitrile (2×1 ml) and dried under vacuum to obtain [(NN$_H$ O$_{Me}$)InI]$_2$(µ-OEt)$_2$ as a white solid. $^1$H NMR (400 MHz, CD$_2$Cl$_2$): δ 6.98 (1H, br. s., ArH), 6.59 (1H, br. s., ArH), 5.08 (1H, d, J=13.3 Hz, NH—CH$_2$—Ar), 3.62-3.83 (2H, m, O—CH$_2$—CH$_3$, NH—CH$_2$—Ar), 2.69 (1H, br. s., N—CH—CH$_2$), 2.64 (4H, br. s., —CH$_2$— of DACH, -N(CH$_3$)$_2$), 2.55-2.47 (1H, m, N—CH—CH$_2$), 2.48-2.50 (1H, m, —CH$_2$—0 of DACH), 2.18 (3H, s, Ar—CH$_3$), 2.06 (3H, s, —N(CH$_3$)$_2$), 1.97 (1H, br. s., —CH$_2$— of DACH), 1.76-1.90 (2H, in, —CH$_2$— of DACH), 1.41 (1H, br. s., —CH$_2$— of DACH), 1.39 (9H, Ar—(CH$_3$)$_3$), 1.05-1.23 (6H, m, —CH$_2$— of DACH and O—CH$_2$—CH$_3$); $^{13}$C{$^1$H} NMR (151 MHz, CD$_2$Cl$_2$) δ 163.5 (Ar C), 139.7 (Ar C), 130.4 (Ar C—H), 128.4 (Ar C—H), 122.4 (Ar C), 120.0 (Ar C), 68.3 (N—CH$_2$—Ar), 60.8 (O—CH$_2$—CH$_3$), 52.6 (N—CH—CH$_2$), 51.4 (N—CH—CH$_2$), 49.9 (N(CH$_3$)$_2$), 40.0 (N(CH$_3$)$_2$), 35.3 (Ar—C(CH$_3$)$_3$), 31.1 (Ar—CH$_3$), 30.4 (Ar—C(CH$_3$)$_3$), 25.4 (—CH$_2$— of DACH), 25.1 (—CH$_2$— of DACH), 23.3 (—CH$_2$— of DACH), 20.9 (—CH$_2$— of DACH), 19.7 (O—CH$_2$—CH$_3$).

Example B3

Synthesis of [(NN$_H$O$_{tBu}$)InI]$_2$(µ-OEt)$_2$

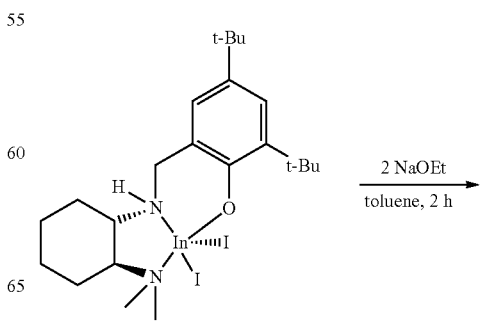

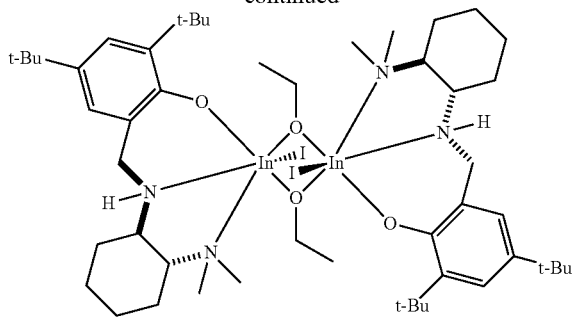

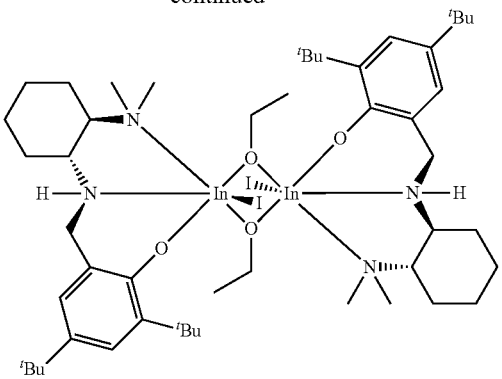

A 25 mL round bottom flask was charged with a solution of NaOEt (56 mg, 0.84 mmol) in 5 mL of toluene. A solution of [(NN$_H$O$_{Me}$)InI$_2$] (300 mg, 0.42 mmol) dissolved in 10 mL of toluene was added dropwise to this mixture. After stirring the reaction mixture for 2 h at room temperature, NaI formation was observed. The salt was removed by filtration through glass filter paper and the remaining yellow solution was evaporated to dryness. The residue was washed with pentane and dried for 2 h in vacuo to yield complex 5 as a white powder (208 mg, 76% yield). $^1$H NMR (400 MHz, CD$_2$Cl$_2$): δ 7.20 (1H, d, J=3 Hz, ArH), 6.75 (1H, d, J=3 Hz, ArH), 5.10 (1H, d, $^2J_{H-H}$=12 Hz, HN—CHH—Ar), 4.33 (m, 1H, OCHMe), 3.78 (1H, m, OCHHMe), 3.73 (1H, d, J=12 Hz, NH—CHH—Ar), 2.64 (3H, s, NMeMe), 2.62 (2H, in, CHN(Me)$_2$ and CHNH), 2.04 (3H, s, NMeMe), 1.90 (4H, m, —CH$_2$— of DACH), 1.41 (9H, s, t-Bu), 1.26 (11H, s, t-Bu and m, —CH$_2$— of DACH), 1.21 (2H, t J=8 Hz, OCH$_2$CH$_3$),1.18 (2H, in, —CH$_2$— of DACH). $^{13}$C {$^1$H} NMR (100.64 MHz, CD$_2$Cl$_2$): δ 13C {$^1$H} NMR (100.64 MHz, CD$_2$Cl$_2$): δ 163.2 (C$_{Ar}$), 138.8 (C$_{Ar}$), 136.0 (C$_{Ar}$), 126.8(CH$_{Ar}$), 124.4 (CH$_{Ar}$), 119.5 (C$_{Ar}$), 67.3(CHNMe$_2$), 60.8 (OCH$_2$CH$_3$), 52.7 (NCH$_2$Ar), 50.3 (CHNCH$_2$Ar), 45.7 (NMeMe), 39.9 (NMeMe), 35.5 (CH$_2$-DACH), 34.7 (CMe$_3$), 32.1 (CMe$_3$), 31.1 (CMe$_3$), 30.5 (CMe$_3$), 25.6 (CH$_2$-DACH), 25.2 (CH$_2$-DACH), 23.2 (CH$_2$-DACH), 19.9 (OCH$_2$CH$_3$). Elemental analysis calc. (found) for C$_{50}$H$_{86}$I$_2$In$_2$N$_4$O$_4$: C. 46.44 (46.41), N. 4.33 (4.34), H. 6.65 (6.60).

Example B4

Synthesis of [(NN$_H$O$_{tBu}$)InI]$_2$(µ-OEt)$_7$

The [(NN$_H$O$_{tBu}$)InI]$_2$(µ-OEt)$_2$ complex was also prepared following the method of Example B3 but using THF and stirring for 16 h as schematically shown below:

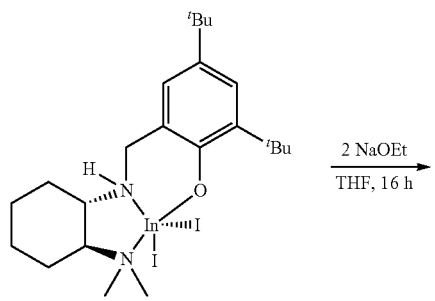

Figure 5:
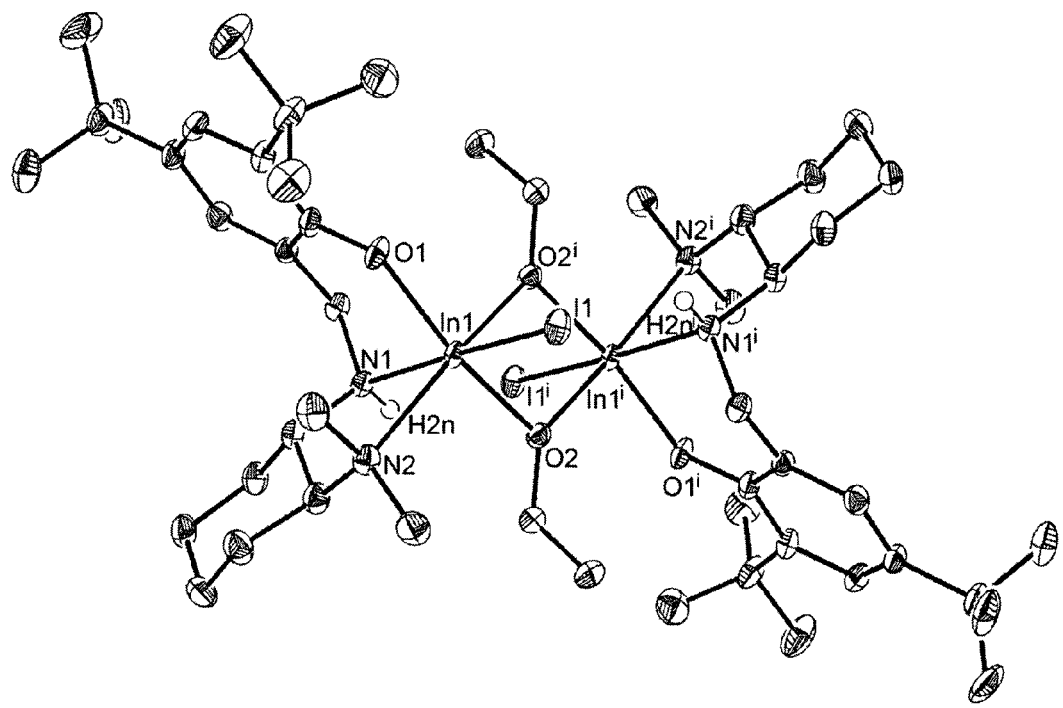
FIG. 5 shows the molecular structure of $[(NN_HO_{tBu})InI]_2(\mu\text{-OEt})_2$ obtained by single-crystal X-ray diffraction.

FIG. 5 shows the molecular structure of [(NN$_H$ O$_{tBu}$)InI]$_2$(µ-OEt)$_2$ obtained by single-crystal X-ray diffraction. It shows two octahedral indium centres bridged by two ethoxide ligands and both cyclohexyl diamine groups in the dimer have the same (R,R) stereochemistry. The molecular structure is depicted with ellipsoids at 50% probability and most H atoms as well as solvent molecules omitted for clarity. Selected bond lengths (Å): In1-I1 (2.8068(3)), In1-O1 (2.082(2)), In1-O2 (2.163(2)), In1-N1 (2.275(2)), In1-N2 (2.381(3)). Selected bond angles (°):O1-In1-O2$^i$ (91.22(8)), O1-In1-O2 (163.88(8)), O1-In1-I1 (92.77(6)), O1-In1-N1 (85.06(8)), O1-In1-N2 (94.93(9)), N1-In1-N2 (75.97(9)), N2-In1-O2 (98.69(9)), Ni—In1-I1 (171.11(6)), In1-O2-In1$^i$ (105.84(8)).

It has been surprisingly found, that [(NN$_H$ O$_{tBu}$)InI]$_2$ (µ-OEt)$_2$ is resistant to dissociation in solution under a variety of conditions, including in the presence of a strong base such as pyridine.

The bisalkoxy bridged dinuclear Indium catalysts of the present invention with X=Cl or Br can be synthesized according to methods analogous to the ones described above.

Examples C

Synthesis of Dinucicar Indium Complexes of the Type [(NN$_H$O$_R$)InX]$_2$(µ-OH)(µ-OEt) with R=Me or t-Bu and X=Cl, Br, or I Example C1

Synthesis of [(NN$_H$O$_{tBu}$)InI]$_2$(µ-OH)(µ-OEt)

A 25 mL round bottom flask was charged with a solution of [(NNO$_{tBu}$)InI]$_2$(µ-OEt)$_2$ (250 mg, 0.19 mmol) in 10 mL CH$_2$Cl$_2$, and then water (3.5 µL, 0.19 mmol) was added to the solution. The reaction was stirred for 1 h and after that the mixture was evaporated to dryness in vacuo. The residue was washed with diethyl ether and dried for 2 h in vacuo, to yield [(NNO$_{tBu}$)InI]$_2$(µ-OH)(µ-OEt) as a white powder. Suitable crystals for X-ray diffraction were grown by slow diffusion on diethyl ether in a CH$_2$Cl$_2$ solution of the complex (204.1 mg, 85% yield). $^1$H NMR (400 MHz, CD$_2$Cl$_2$): δ 7.20 (1H, d, J=3 Hz, ArH), 6.78 (1H, d, J=3 Hz, ArH), 4.82 (1H, d, $^2J_{H-H}$=12 Hz, HN—CHH—Ar), 4.39 (m, 0.5H, OCHHMe), 4.20 (0.5H, m, OCHHMe), 3.74 (1H, d, J=12 Hz, NH—CHH—Ar), 3.69 (1H, OH), 3.43 (1H, m CHN(Me)$_2$), 2.62 (1H, m, CHNH), 2.55 (3H, s, NMeMe), 2.47 (2H, m, —CH$_2$— of DACH), 1.91 (3H, s, NMeMe), 1.84 (4H, m, —CH$_2$— of DACH), 1.43 (9H, s, t-Bu), 1.27

(11H, s, t-Bu and m, —CH$_2$— of DACH), 1.15 (2H, t $^3J_{H-H}$=6 Hz, OCH$_2$CH$_3$), 1.07 (2H, m, —CH$_2$— of DACH). $^{13}$C {$^1$H} NMR (100.64 MHz, CD$_2$Cl$_2$): δ 163.2 ($_{CA}$), 138.9 (C$_m$), 136.7 (C$_{Ar}$), 126.8(CH$_A$), 124.5 (CH$_{AT}$), 119.9 (C$_{Ar}$), 67.3 (OCH$_2$Cl$_3$), 62.0 (CHNMe$_2$), 53.3 (CHNCH$_2$Ar), 50.3 (NCH$_2$Ar) 46.0 (NMeMe), 38.1(NMeMe), 34.3(CMe$_3$), 32.1 (CMe$_3$), 31.1 (CMe$_3$), 30.5 (CMe$_3$), 26.4 (CH$_2$-DACH), 25.4 (CH$_2$-DACH), 25.3 (CH$_2$-DACH), 22.4 (CH$_2$-DACH), 19.9(OCH$_2$CH$_3$). Elemental analysis calc. (found) for C$_{48}$H$_{84}$I$_3$In$_2$N$_4$O$_4$: C. 45.46 (45.13), N. 4.43 (4.40), H. 6.64 (6.69).

Figure 6:
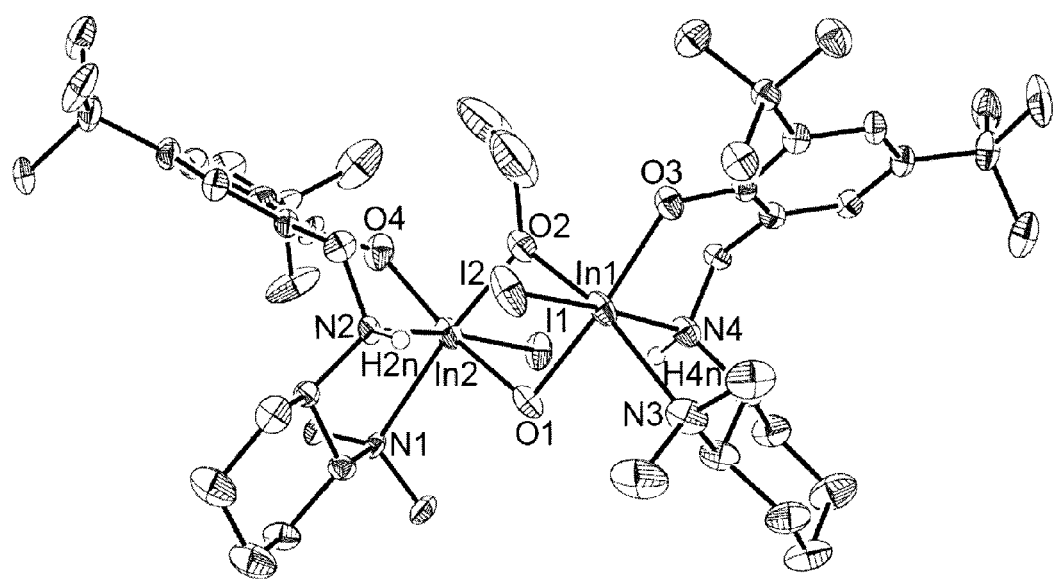
FIG. 6 shows the molecular structure of $[(NN_HO_{tBu})InI]_2(\mu\text{-OH})(\mu\text{-OEt})$, obtained by single-crystal X-ray diffraction.

FIG. 6 shows the molecular structure of [(NNO$_{tBu}$)InI]$_2$ (μ-OH)(μ-OEt), obtained by single-crystal X-ray diffraction. FIG. 6 shows a dinuclear complex where both indium centres are in a distorted octahedral geometry. The NNO ligands are bound to the metal center infac-fashion and only the homo-chiral (R,R/R,R)-[(NNO$_{tBu}$)InI]$_2$(μ-OH)(μ-OEt) is observed. The molecular structure is depicted with ellipsoids at 50% probability and most H atoms as well as solvent molecules omitted for clarity. Selected bond lengths (Å): In1-O1 (2.180(3)), In2-O1(2.211(3)), In1-O2 (2.142(3)), In2-O2 (2.146(3)), In1-O3 (2.090(3)), In1-N3 (2.336(4)), In1-N4 (2.273(4)), In1-I2 (2.8030(4)), In2-I1(2.7923(4)), In2-O4 (2.099(5)), In2-N1 (2.338(9)), In—N2 (2.265(5)). Selected bond angles (°): O1-In1-O2 (92.49(12)), N3-In1-I2 (96.20(10)), N3-In1-O3 (103.29(14)), N1-In2-I1 (98.20 (15)), N1-In2-O4 (100.14(5)), O1-In2-O2: 74.58(12)), In1-O1-In2(103.26(13)), In1-O2-In2(106.90(14)), O2-In1-O3 (165.62(12)).

Example C2

Synthesis of [(NN$_H$O$_{Me}$)InI]$_2$(μ-OH)(μ-OEt)

The complex [(NN$_H$O$_{Me}$)InI]$_2$(μ-OH)(μ-OEt) was prepared as shown below:

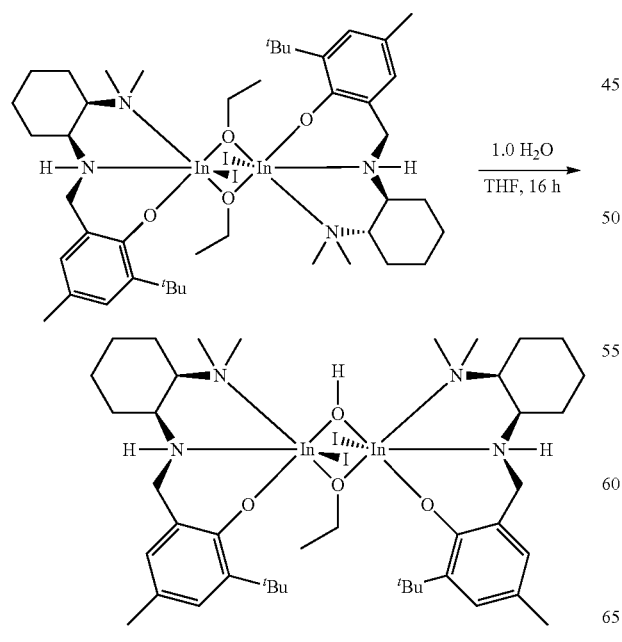

Example D

Synthesis of [($^{TH}$-NN$_{Me}$O$_{tBu}$)InCl]$_2$(μ-Cl)(μ-OEt) and [($^{TH}$-NN$_{Me}$O$_{Me}$)InCl]$_2$(μ-Cl)(μ-OEt)

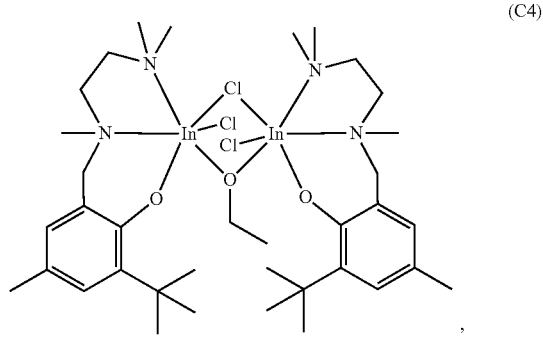

(C4)

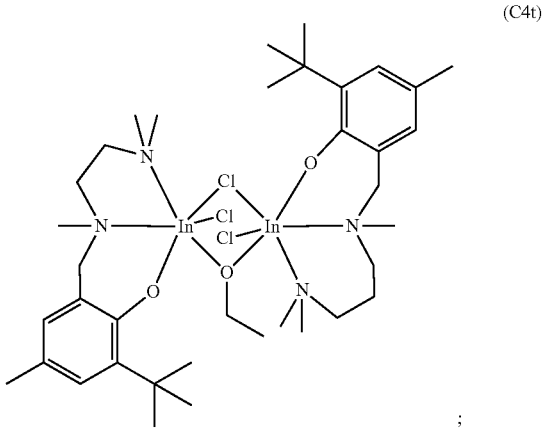

(C4t)

;

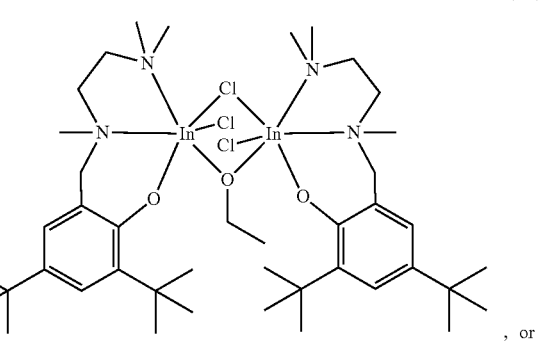

(C5)

, or (C5t)

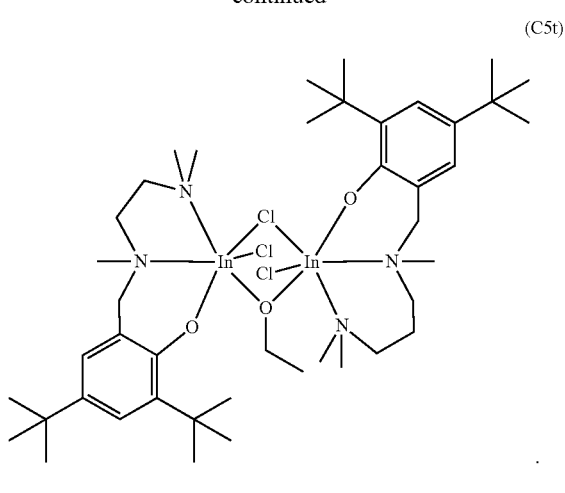

The proligand for the synthesis of catalyst (C5) was prepared as described in Williams et al., J. AM. CHEM. SOC. 2003, 125, 11350-11359, and the catalyst (C5) prepared according to methods analogous to the preparation of [(NNO$_{tBu}$)InCl]$_2$(μ-Cl)(μ-OEt) as described above. The catalyst (C4) can be prepared in an analogous manner.

Example E

Synthesis of the Dinuclear Indium Catalysts of the Type [(NN$_{Me}$O$_{tBu}$)In(Cl)]$_2$(μ-Cl)(μ-OEt)

The catalyst represented by structural formula (D7)

(D7)

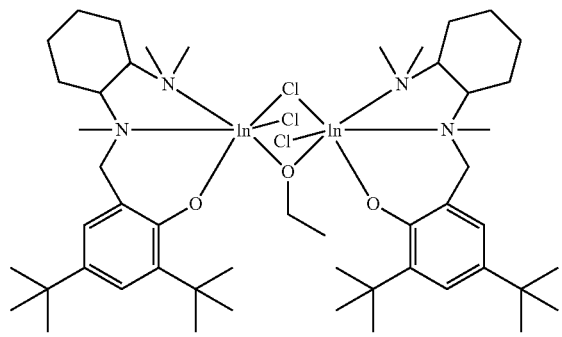

(as racemic mixture of (RR,RR) and (SS,SS)) was prepared according to methods analogous to the one described in Example A4 with proligand prepared according to the following scheme, and analogously to methods described in Organometallics, 2009, 28 (5), 1309-1319:

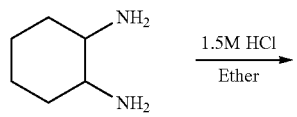

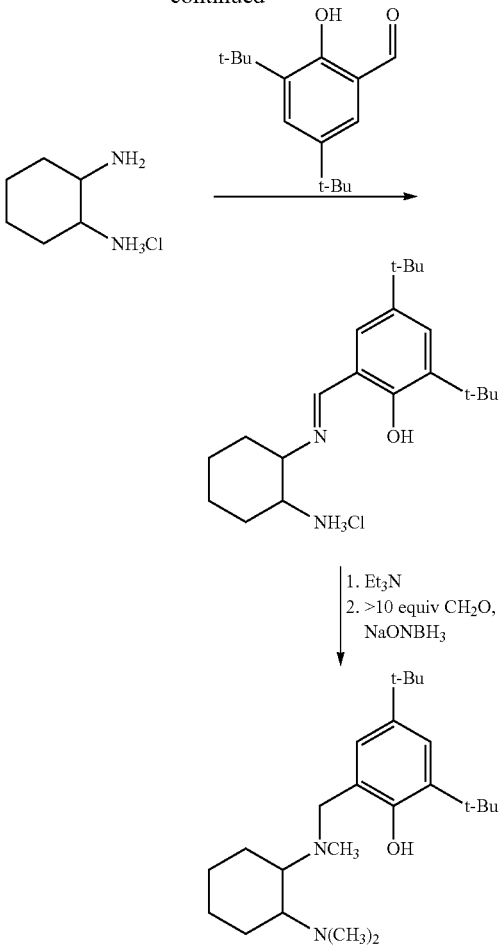

POLYMERIZATION EXAMPLES

Example: Polymerization of rac-lactide

The asymmetrically bridged complexes [(NN$_H$O$_{Me}$)InCl]$_2$(μ-Cl)(μ-OEt), [(NN$_H$O$_{Me}$)InI]$_2$(μ-OEt), and [(NN$_H$O$_{Me}$)InI]$_2$(μ-OH)(μ-OEt) as well as symmetrically-bridged complex [(NN$_H$O$_{Me}$)InI]$_2$(μ-OEt)$_2$ were used as initiators and catalysts for the ring opening polymerization of racemic lactide (rac-LA, i.e., racemic mixture of D-lactide (D-LA) and L-lactide (L-LA)). The reactions, monitored by $^1$H NMR spectroscopy at 25° C. showed approximately 90% conversion of 200 equiv of rac-LA to PLA in 30 minutes, with slight variations in rate depending on the initiator. In all cases, an induction period was observed which varied subtly (3 to 8 min) with the electronic differences in the various complexes. After this period, the polymerization reactions were first-order in catalyst and LA concentrations with similar rate constants within experimental error, giving an overall second-order rate law for consumption of LA (rate=k[catalyst][LA]) (Table 1). It is believed that that the catalyst in all cases is the dinuclear species behaving as one initiator.

NMR Scale Polymerization of rac-lactide with Indium Complexes for Kinetic Experiments In a teflon sealed NMR tube, 0.50 mL of the indium complex in CD$_2$Cl$_2$ (0.0048 M, 0.0024 mmol) was added to a solution of rac-lactide (66 mg; 0.47 mmol) and an internal standard 1,3,5-trimethoxybenzene (5 mg; 0.03 mmol) in 0.48 mL of $CD_2Cl_2$. This mixture was immediately cooled in liquid nitrogen. The NMR tube was waimed to room temperature before it was inserted into the instrument (400MHz Avance Bruker Spectrometer). The polymerization was then monitored to ca. 95% conversion.

The following rate constants were observed:

| Entry | Catalyst | $k_{obs}$ (s$^{-1}$) | k (M$^{-1}$s$^{-1}$) |
|---|---|---|---|
| 1[a] | [(NNO$_{tBu}$)InCl]$_2$(μ-OEt)(μ-Cl) | 0.0023 | 1.15 (±0.27) |
| 2[a] | [(NNO$_{Me}$)InI]$_2$(μ-OEt)(μ-I) | 0.0034 | 1.70 (±0.22) |
| 3[b] | [(NNO$_{Me}$)InI(μ-OEt)]$_2$ | 0.0014 | 2.80 (±0.56) |
| 4[a] | [(NNO$_{Me}$)InI]$_2$(μ-OEt)(μ-OH) | 0.0036 | 1.67 (±0.14) |

All the reaction were carried out in an NMR scale with 200 equiv of LA at 25° C. and followed to 90% conversion. [a][LA]=0.46 M. [catalyst]=0.0023 M ; [b][LA]= 0.114 M. [catalyst]=0.00057 M in CDCl$_3$. 1,3,5-trimethoxybenzene (TMB) was used as internal standard. The value of $k_{obs}$ was determined from the slope of the plots of ln([LA]/[TMB]) vs. time.

Large-scale Polymerization of rac-lactide

In a typical experiment, 129.3 mg of rac-lactide (0.92 mmol) was dissolved in 3 mL of $CH_2Cl_2$ in a vial and stirred using a magnetic stir bar. To this solution 1mL of a stock solution of one of the above indicated indium complexes in $CH_2Cl_2$ was added (0.0046 M; 0.0046 mmol). The reaction was allowed to proceed for 16 h and then concentrated to dryness. A sample of the residue was dissolved in $CDCl_3$ to be analyzed by 1H NMR spectroscopy to determine conversion. The resulting polymeric material was dissolved in a minimum amount of $CH_2Cl_2$ and added to cold wet methanol (0° C., 7 mL). The polymer crashed out of solution, and was isolated by centrifugation. The supernatant was decanted off and the polymer was dried under high vacuum for 2 h. The resulting polymer was then analyzed by NMR (Nuclear Magnetic Resonance) and GPC (Gel Permeation Chromatography).

Figure 7:
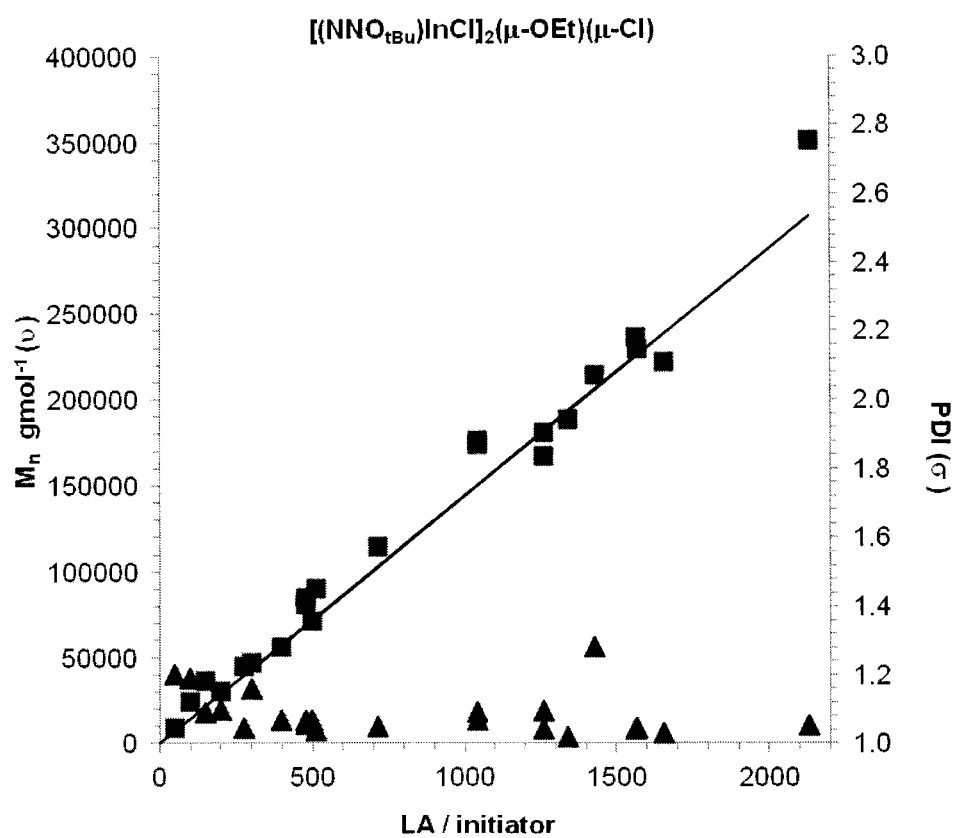
FIG. 7 shows the observed poly(lactide) (PLA) $M_n$ (v) and molecular weight distribution ($\sigma$) as function of added rac-lactide for $[(NN_HO_{tBu})InCl]_2(\mu\text{-Cl})(\mu\text{-OEt})$ ($M_n$=number averaged molecular weight, PDI=polydispersity index).

FIG. 7 shows the observed poly(lactide) (PLA) (v) and molecular weight distribution (σ) as functions of added rac-lactide for [(NN$_H$O$_{tBu}$)InCl]$_2$(μ-Cl)(μ-OEt) ($M_n$=number averaged molecular weight, PDI=polydispersity index). The line indicates calculated $M_n$ values based on the LA: catalyst ratio. The ability to obtain PLA across a wide molecular weight range with low PDI values is a direct result of the unusually stable nature of this catalyst and the lack of termination mechanisms. It is believed that this living behavior may be a direct result of the dinuclear nature of the catalyst.

Figure 8:
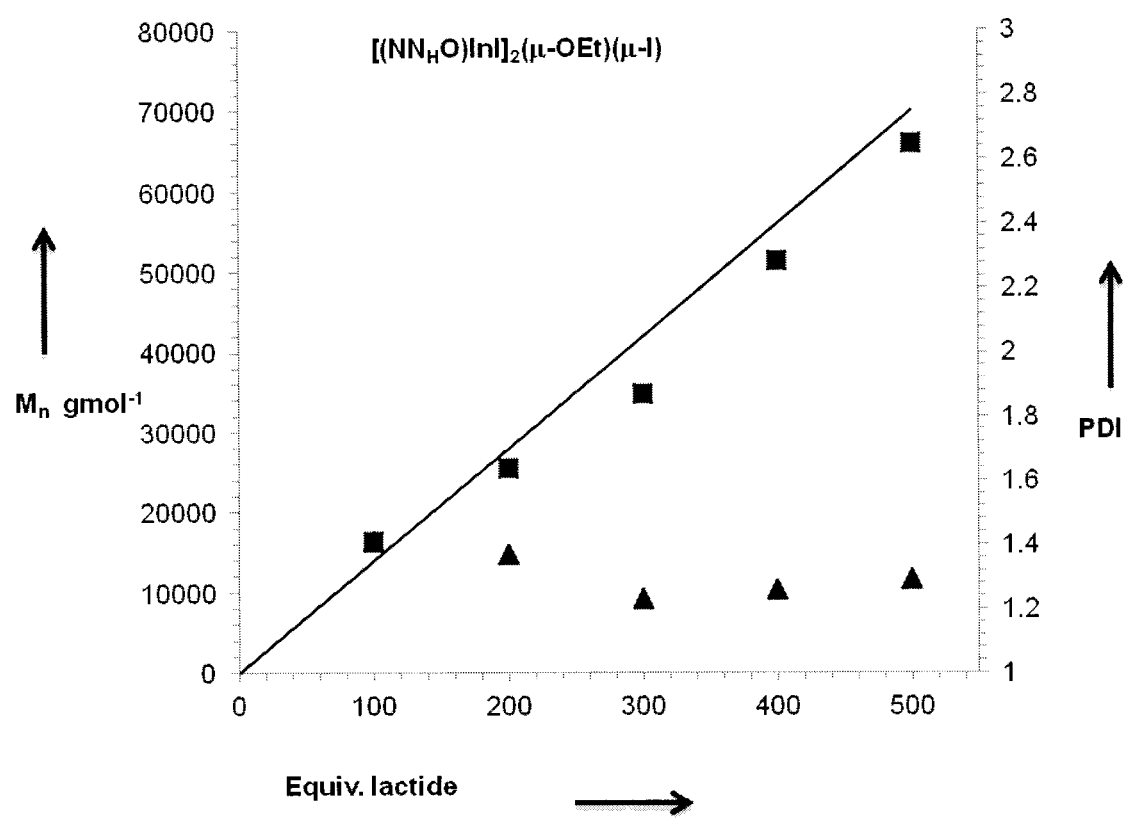
FIG. 8 shows the observed poly(lactide) (PLA) $M_n$ (v) and molecular weight distribution ($\sigma$) as function of added rac-lactide for $[(NN_HO_{tBu})InI]_2(\mu\text{-OH})(\mu\text{-OEt})$ ($M_n$=number averaged molecular weight, PDI=polydispersity index).
Figure 9:
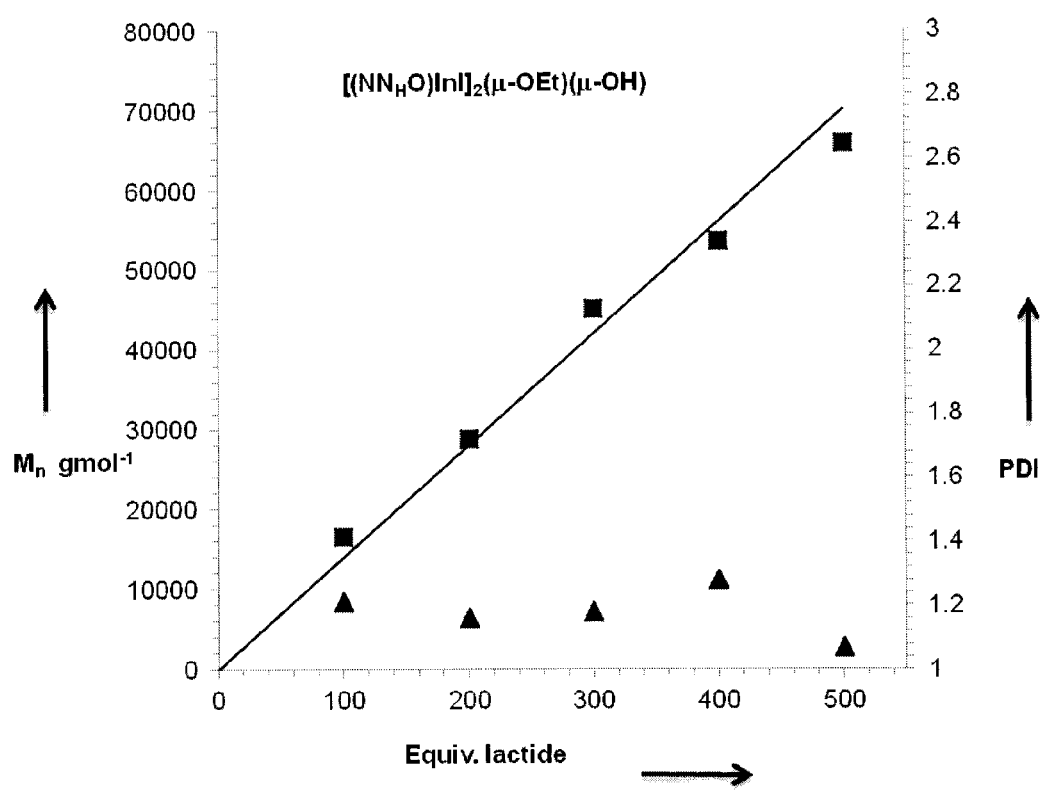
FIG. 9 shows the observed poly(lactide) (PLA) $M_n$ (v) and molecular weight distribution ($\sigma$) as function of added rac-lactide for $[(NN_HO_{tBu})InI]_2(\mu\text{-OH})(\mu\text{-OEt})$ ($M_n$=number averaged molecular weight, PDI=polydispersity index).
Figure 10:
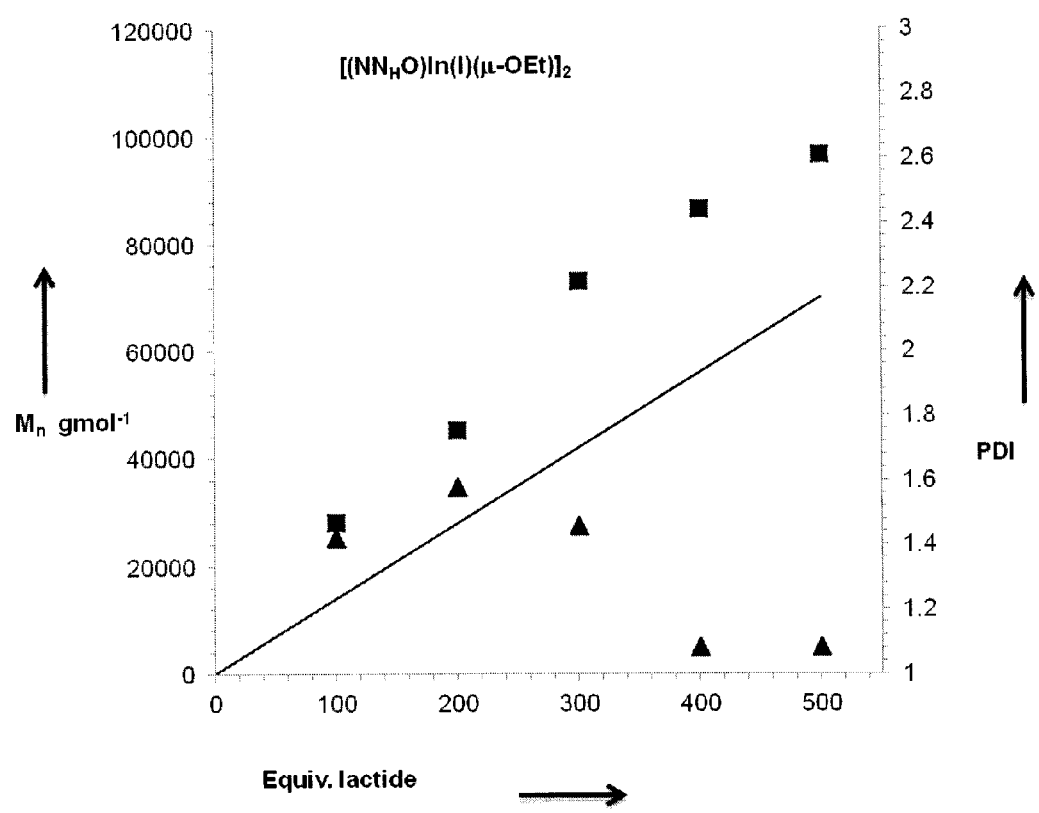
FIG. 10 shows the observed poly(lactide) (PLA) $M_n$ (v) and molecular weight distribution ($\sigma$) as function of added rac-lactide for $[(NN_HO_{Me})InI]_2(\mu\text{-OEt})_2$ ($M_n$=number averaged molecular weight, PDI=polydispersity index).

FIGS. 8, 9 and 10 show the observed poly(lactide) (PLA) $M_n$ (v) and molecular weight distribution (σ) as functions of added rac-lactide for [(NN$_H$O$_{tBu}$)In]$_2$(μ-I(μ-OEt), [(NN$_H$O$_{tBu}$)InI]$_2$(μ-OH)(μ-OEt) and [(NN$_H$O$_{Me}$)InI]$_2$(μ-OEt)$_2$, respectively ($M_n$=number averaged molecular weight, PDI=polydispersity index). The line indicates calculated $M_n$ values based on the LA: catalyst ratio.

The bisethoxy bridged catalyst, [(NN$_H$O$_{Me}$)InI]$_2$(μ-OEt)$_2$ has been found to exhibit a faster rate of polymerization (see entry 3 in above table).

Example: Polymerization of ε-caprolactone with [In(NN$_H$O)]$_2$(μ-OEt)(μ-Cl)

In a glove box, a Teflon-sealed NMR tube was charged with a solution of [(NNO)InCl]$_2$(μ-OEt )(μ-Cl) obtained as described above (4.5 μmol) and TMB (trimethoxybenzene, 30 μmol) in ACN-d$_3$ (deuterated acetonitrile; 1.0 mL). Then ε-caprolactone (ε-CL, 100.7 uL, 200 eqv.) was added to the solution. The tube was taken out of the glove box and immediately placed in a Bruker AV 300 NMR spectrometer for in-situ monitoring with temperature being maintained at 50.8° C. The change of the relative concentration of ε-CL over time is shown in FIG. 1. The observed rate was found to be first order to monomer concentration, and has the value as indicated in row "1" of Table 1. In a further experiment, the procedure as described in this Example was followed, however, the temperature during in-situ monitoring was maintained at 40.3° C. The observed rate was found to be first order to monomer concentration, and has the value as indicated in row "2" of Table 1.

Polymerization of 4-(but-3-en-1-yl)oxetan-2-on (f-BBL-1) with [In(NNO)]$_2$(μ-OEt)(μ-Cl)

f-BLL-1 was prepared according to Organic Letters 2006, Vol. 8, No. 17, 3709-3712.

In a glove box, a Teflon-sealed NMR tube was charged with a solution of [In(NNO)]$_2$(μ-OEt)(μ-Cl) obtained as described above (4.5 μmol) and TMB (trimethoxybenzene, 30 μmol) in ACN-d$_3$ (deuterated acetonitrile; 1.0 mL). Then 4-(but-3-en-1-yl)oxetan-2-on (f-BLL-1, 100 uL, 200 eqv.) was added to the solution. The tube was taken out of the glove box and immediately placed in a Bruker AV 300 NMR spectrometer for in-situ monitoring with temperature being maintained at 61.5° C. The observed rate was found to be first order to monomer concentration, and has the value as indicated in row "3" of Table 1.

TABLE 1

Polymerization of ε-CL and f-BBL-1[a]

| entry | monomer | Solvent | temp (° C.)[a] | [cat] (mmol/L) | [M]$_0$/[cat] | $K_{obs}$[b] (*10$^{-5}$ s$^{-1}$) |
|---|---|---|---|---|---|---|
| 1 | ε-CL | ACN-d$_3$ | 50.8 | 4.6 | 200 | 105.8 |
| 2 | ε-CL | ACN-d$_3$ | 40.3 | 4.6 | 200 | 45.5 |
| 3 | f-BBL-1 | ACN-d$_3$ | 61.5 | 1.6 | 200 | 5.0 |

[a]The reactions were monitored in-situ on Bruker AV 300. The temperature is calibrated to be 62.4° C. by 80% ethylene glycol in DMSO-d$_6$.
[b]Rates were first order to monomer concentration.

Polymerization with (C5)

Rae-LA was polymerized with catalyst (C5). The observed polymerization rate was $k_{obs}$=0.000024 s$^{-1}$ with [LA]/[Cat]=200. The tacticity of the obtained polylactide polymer is atatic ($P_r=P_m$=0.49).

Block Copolymerization Examples

The block copolymers in Table 2 have been prepared using the catalyst [(NN$_H$O$_{tBu}$)InCl]$_2$(μ-OEt)(μ-Cl) obtained as described in Example above.

TABLE 2

Block copolymers[a]

| Entry | M$_1$[b] | M$_2$ | Equivalent[c] | $M_{n,theo}$(kDa) | $M_{n,GPC}$ (kDa) | PDI |
|---|---|---|---|---|---|---|
| 1 | Rac-lac | L-lac | 650 + 800 | 208.4 | 162.7 | 1.069 |
| 2 | Rac-lac | L-lac | 156 + 800 | 149.2 | 156.9 | 1.050 |
| 3 | L-lac | Rac-lac | 755 + 288 | 150.2 | 163.3 | 1.087 |
| 4 | L-lac | Rac-lac | 516 + 516 | 148.6 | 163.2 | 1.083 |
| 5 | L-lac | Rac-lac | 288 + 743 | 147.8 | 165.6 | 1.058 |
| 6 | Rac-lac | BBL | 200 + 200 | 46.0 | 41.5 | 1.065 |
| 7 | L-lac | BBL | 200 + 200 | 41.4 | | |

TABLE 2-continued

Block copolymers[a]

| Entry | $M_1$[b] | $M_2$ | Equivalent[c] | $M_{n,theo}$ (kDa) | $M_{n,GPC}$ (kDa) | PDI |
|---|---|---|---|---|---|---|
| 8 | L-lac | f-BBL-1 | 100 + 20 | 17.6 | 25.5 | 1.203 |
| 9 | BBL | f-BBL-1 | 100 + 20 | 10.8 | 15.8 | 1.005 |

[a]These reactions were run in DCM except entry 9, which was done in THF. Second monomer was added directly into polymerization solution after the first monomer was fully converted. Heating might be needed when polymerizing BBL and f-BBL-1.
[b]$M_1$ means the first monomer.
[c]The left and right numbers mean the equivalent of $M_1$ and $M_2$ respectively.

With regard to entry 1 in Table 2, that is, the block copolymerization of L-lac (i.e., L-lactide) and rac-lac (i.e., racemic lactide), a Strauss flask was charged with a solution of [(NN$_H$O$_{tBu}$)InCl]$_2$(μ-OEt)(μ-Cl) (16.6 μmol) in dichloromethane in a glove box. Then L-lac (1.81 g) was dissolved and transferred into the flask while stirring. After overnight stirring, a small amount of solution was pipetted out and quenched with 2 drops of HCl/Et$_2$O, which is used as a parallel sample to check the properties of the first block. Then rac-lac (0.69 g) was added to the rest solution in the flask. Then it was stirred overnight again to allow the second monomer to be fully converted. After that, it was quenched with 0.5 ml HCl/Et$_2$O. Conversion was measured by comparing the relative integration of methine hydrogen peaks in polymer and monomer. The block copolymer was precipitated by adding cold methanol and washed with cold methanol three times. Then the block copolymer was dried under vacuum to constant weight.

The block copolymers of entries 2 to 9 in Table 2, were prepared analogously as described above for entry 1.

Figure 2:
FIG. 2 shows the $^1$H NMR of the block copolymer L-lac-b-f-BBL.

FIG. 2 shows the $^1$H NMR of L-lac-b-f-BBL-1 (Entry 8, Table 2), purified polymer. 600 MHz.

Figure 3:
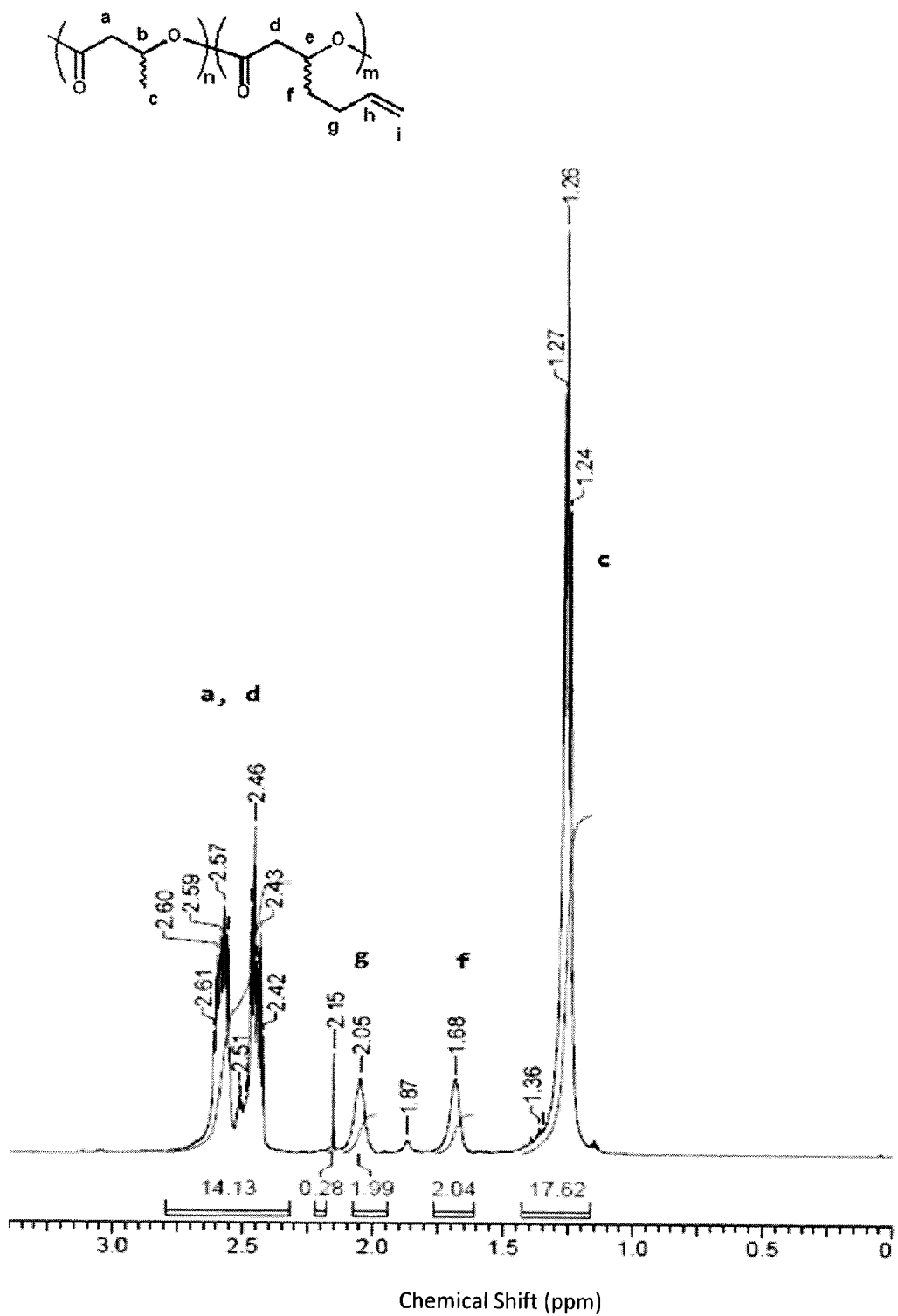
FIG. 3 shows the $^1$H NMR of the block copolymer BBL-b-f-BBL.

FIG. 3 shows the $^1$H NMR of BBL-b-f-BBL-1 (Entry 9, Table 2), purified polymer. 600 MHz.

Figure 4:
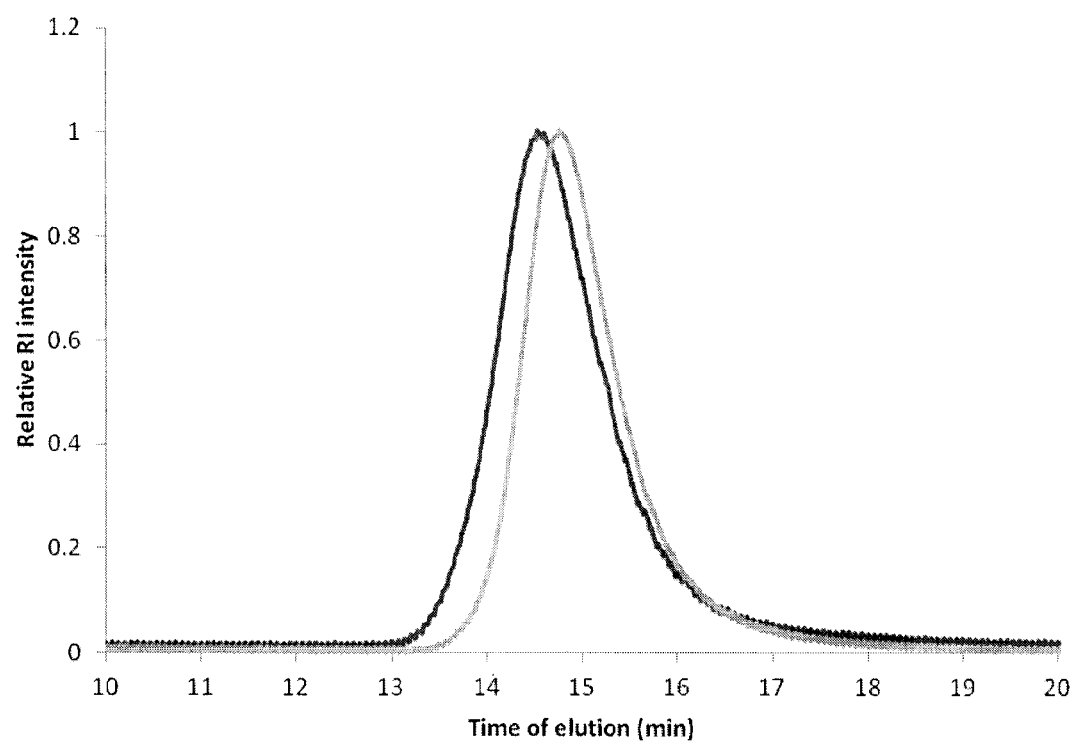
FIG. 4 shows the GPC elution diagram of poly(L-lac-b-rac-lac) (left peak) and its first block, poly(rac-lac).

FIG. 4 shows the GPC elution diagram of poly(L-lac-b-rac-lac) (left peak, Mn=163.3 kDa, Entry 3 in Table 2) and its first block poly(rac-lac) (right peak, Mn=124.4 kDa).

Example: Immortal Ring-opening Polymerization of β-butyrolactone

The dinuclear Indium catalyst [[(NN$_H$O$_{tBu}$)InCl]$_2$(μ-OEt)(μ-Cl) (see also Examples A; hereinafter in this example further denoted as "1") was used for the ring opening polymerization of the cyclic ester β-butyrolactone to form the biodegradable polyester poly(hydroxybutyrate) (PHB):

Catalyst 1 has been found to show remarkable activity and control during polymerization, allowing for formation of diblock polymers. Addition of high ratios of alcohols to the dinuclear Indium catalyst has been found to lead to fast chain transfer and immortal polymerization.

At room temperature, polymerizations of 200 equivalents of BBL in THF reach full conversion in one hour. There is a significant solvent effect at room temperature: $k_{obs}$ THF-d$_8$ (2.9×10$^{-4}$ s$^{-1}$) >CD$_2$Cl$_2$ (6.1×10$^{-5}$ s$^{-1}$)~CD$_3$CN (5.5×10$^{-5}$ s$^{-1}$)>>toluene (rate not measurable at room temperature). However, heating the reactions to 60° C. increases the rates significantly and allows all reactions to reach full conversion in under 4 hours.

All PHB samples produced with complex 1 were atactic.

There is good agreement between calculated and experimental $M_n$ for [BBL]:[1] ratios of up to 5000. PHB samples of greater than 300 kDa with low PDIs have been isolated:

| Entry | [BBL]:[1] | % Conv.[a] | $M_n$ (calc)[b] g mol$^{-1}$ | $M_n$ (GPC)[c] g mol$^{-1}$ | PDI[c] |
|---|---|---|---|---|---|
| 1 | 200 | >99 | 17260 | 20400 | 1.02 |
| 2 | 400 | >99 | 34480 | 36700 | 1.06 |
| 3 | 600 | >99 | 51700 | 58820 | 1.07 |
| 4 | 800 | >99 | 68920 | 91480 | 1.07 |
| 5 | 1000 | >99 | 86140 | 82090 | 1.07 |
| 6 | 2000 | >99 | 172230 | 135000 | 1.05 |
| 7 | 3000 | >99 | 258320 | 202000 | 1.05 |
| 8 | 4000 | >99 | 344410 | 256200 | 1.05 |
| 9 | 5000 | 96 | 413280 | 314700 | 1.04 |

[a]Monomer conversion, determined by $^1$H NMR spectroscopy.
[b]$M_{n\ calc}$ = [BBL]$_o$/[1] × BBL conversion × $M_{BBL}$ + $M_{EtOH}$. All reactions were carried out in THF at 25° C. for 21 h.
[c]Determined by GPC-LALLS dn/dc = 0.067 mL/g).

Monitoring the iROP of BBL in CD$_3$CN at 60° C. by $^1$H NMR spectroscopy shows first order polymerization of monomer to 90% conversion.

Figure 11:
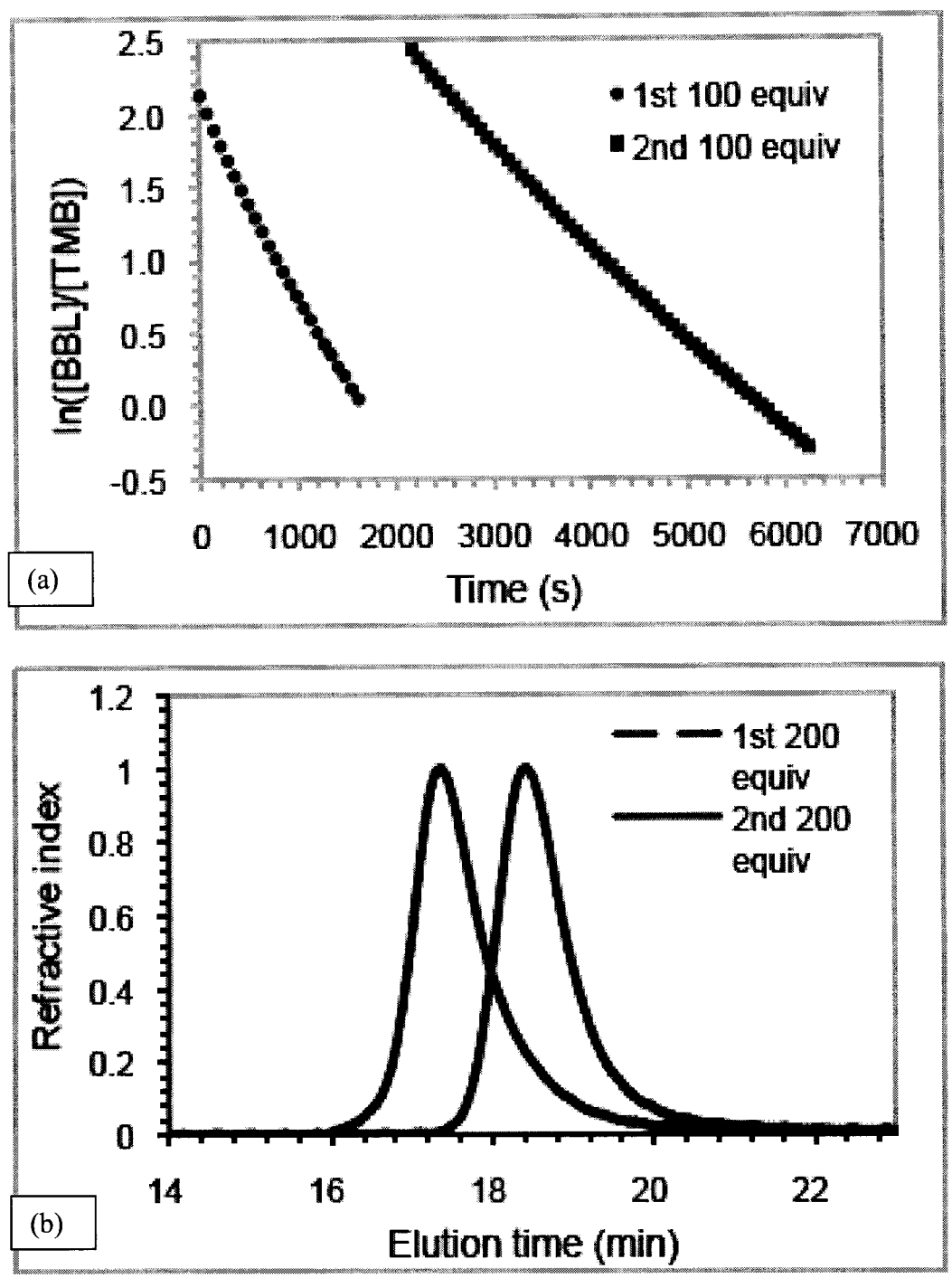
FIG. 11 shows in part (a), top, a plot of Ln([BBL]) versus time for two sequential additions of 100 equiv of [BBL]/[1] in CD$_3$CN at 60.6° C., and in part (b), bottom, the GPC traces of the polymers produced by 20 consecutive additions of 200 equiv. of [BBL]/[1] in THF at 25° C.

Two consecutive polymerizations of 100 equivalents of BBL with complex 1 on the NMR scale resulted in two first order plots, with the second addition showing a slightly lower rate than the initial addition as can be seen in FIG. 11. FIG. 11 (a) shows a plot of Ln([BBL]) versus time for two sequential additions of 100 equiv of [BBL]/[1] in CD$_3$CN at 60.6° C. [1]=0.0045 M, [BBL]=0.45 M. FIG. 11 (b) shows GPC traces of the polymers produced by 20 consecutive additions of 200 equiv. of [BBL]/[1] in THF at 25° C. [1]=0.0045 M, [BBL]=0.90 M. 1st addition, dashed line ($M_n$=20.4 kDa, PDI=1.02). 2nd addition, solid line ($M_n$=42.8 kDa, PDI=1.05).

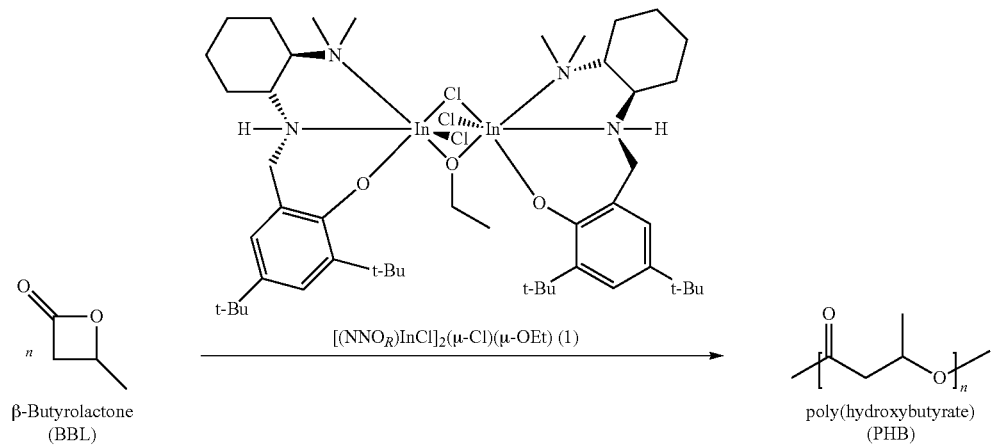

Repeating this experiment on a larger scale (consecutive additions of 200 equiv BBL) resulted in PHB with $M_n$ corresponding to 400 enchained units.

Polymerization reactions were also carried out from 22 to 72° C., and activation parameters were obtained from the resulting Eyring plot ($\Delta H^\ddagger=58(4)$ kJmol$^{-1}$, $\Delta S^\ddagger=86(13)$ JK$^{-1}$ mol$^{-1}$.

Catalyst 1 is believed to undergo exchange with added alcohol. Complex 1 was dissolved in neat dry methanol at room temperature for 16 h, followed by removal of the solvent. The analogous methoxy complex was formed. The reaction of 1 with two or ten equivalents of dry ethanol was monitored for 24 h by $^1$H NMR spectroscopy (25° C., CDCl$_3$). The spectra remain essentially unchanged during this period, suggesting that the rate of exchange is faster than the NMR timescale.

A two-component catalytic system composed of complex 1 and a chain transfer agent, such as ethanol or mPEG, leads to the immortal ring opening polymerization of BBL:

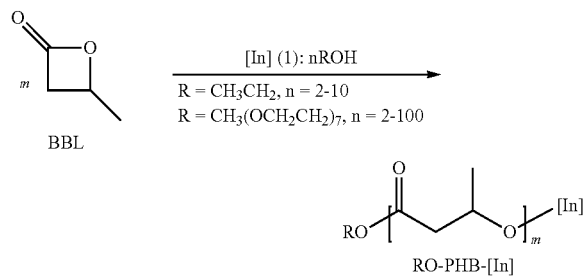

The molecular weights of the resulting polymers were found to be consistent with theoretical values and molecular weight distributions are uniformly low (see the following Table which shows the results for iROP of BBL with EtOH and mPEG, i.e., monomethylated poly(ethylene glycol).[a]).

| Entry | ROH | [BBL]/[ROH]/[1] | $M_{n,theo}$[b] g mol$^{-1}$ | $M_{n\ expt}$[c] g mol$^{-1}$ | PDI[c] |
|---|---|---|---|---|---|
| 1 | — | 1000/0/1 | 86140 | 82890 | 1.07 |
| 2 | EtOH | 1000/2/1 | 28740 | 28340 | 1.01 |
| 3 | EtOH | 1000/4/1 | 17260 | 16770 | 1.01 |
| 4 | EtOH | 4000/10/1 | 31350 | 44020 | 1.01 |
| 5 | mPEG | 1000/2/1 | 28950 | 27970 | 1.01 |
| 6 | mPEG | 1000/4/1 | 17510 | 17070 | 1.02 |
| 7 | mPEG | 10000/20/1 | 40920 | 36090 | 1.01 |
| 8 | mPEG | 10000/100/1 | 8360 | 7570 | 1.03 |

[a]Experiments in THF, 21° C., 16 h, [1] = 0.0018M. entries 1-6 21 h, entries 7-8 46 h. Conversions: entries 1-7 100%, entry 8 94%; mPEG = CH$_3$(OCH$_2$CH$_2$)$_7$—OH
[b]$M_{n\ calc}$ = [BBL]$_o$/([ROH] + [1]) × BBL conversion × $M_{BBL}$ + $M_{ROH}$. All reactions were carried out in THF at 25° C. for 21 h.
[b]$M_{n\ calc}$ = [BBL]$_o$/([ROH] + [1]) × BBL conversion × $M_{BBL}$ + $M_{ROH}$.
[c]Determined by GPC-LALLS for PHB and mPEG-co-PHB, dn/dc = 0.067 and 0.063 mL/g respectively.)

In particular, polymerization of 10000 equivalents of BBL in the presence of 100 equivalents of mPEG proceeds in a highly controlled manner ($M_{n\ theo}$ 8.36 kDa, $M_{n\ expt}$ 55 7.57 kDa) (see, entry 8 in the above). These results indicate that both ethanol and a longer chain alcohol function well as chain transfer agents and confirm the robustness of catalyst 1 in the presence of large quantities of protic additives.

Example: Immortal Ring-opening Polymerization of Lactide

General consideration. All the air and moisture sensitive manipulations were carried out in an MBraun glove box or using standard Schlenk line techniques. A Bruker Avance 300 MHz or 400 MHz spectrometer was used to record $^1$H and $^{13}$C spectra. A Bruker Avance 600 MHz spectrometer was used to acquire homonuclear decoupled $^1$H {$^1$H} spectra of polylactide. $^1$H NMR chemical shifts are given in ppm versus residual protons in deuterated solvents as follows: δ 7.27 CDCl$_3$. $^{13}$C NMR chemical shifts are given in ppm versus residual $^{13}$C in solvents as follows: δ 77.23 CDCl$_3$. Molecular weights and polydispersity indices were determined by triple detection gel permeation chromatography using a Waters liquid chromatograph equipped with a Waters 515 HPLC pump, a Waters 717 plus autosampler, Waters Styragel columns (4.6×300 mm) HR5E, HR4 and HR2, a Waters 2410 differential refractometer, a Wyatt tristar miniDAWN laser light scattering detector and a Wyatt ViscoStar viscometer. A flow rate of 0.5 mL/min was used and samples were dissolved in tetrahydrofuran (THF) (ca. 2 mg/mL). The measurements were carried out at laser wavelength of 690 nm, at 25° C. The data were processed using the Astra software provided by Wyatt Technology Corp. A differential scanning calorimeter (DSC) Q1000 (TA Instruments) was employed to measure the glass transition ($T_g$) and melting ($T_m$,) temperatures.

Materials. THF were taken from an IT Inc. solvent purification system with activated alumina columns and degassed before use. CH$_2$Cl$_2$ was refluxed with CaH$_2$, distilled and degassed before use. EtOH, CDCl$_3$ were dried over CaH$_2$, transferred under vacuum and degassed through freeze-pump-thaw cycles before use. DL-, L- and D-lactide were donated by Purac Biomaterials and recrystallized twice in toluene. Beta-butyrolactone, purchased from Aldrich, was stirred with CaH$_2$ for 48 hours, distilled under vacuum, degassed through freeze-pump-thaw cycles and kept in the freezer at −30° C. The catalyst [(NN$_H$O$_{tBu}$)InCl]$_2$OEt)(μ-Cl) (also referred to in this Example as catalyst or complex 1) was prepared as described in Example A4.

Synthesis of triblock copolymers. Complex 1 (22.7 mg, 0.0206 mmol) was dissolved in CH$_2$Cl$_2$ and transferred to a round bottom flask. While stirring, a solution of L-LA in CH$_2$Cl$_2$ (1.267 g, 8.80 mmol) was added slowly. The polymerization was allowed to stir for a few hours and then a solution of the second monomer rac-LA (0.966 g, 6.71 mmol) in CH$_2$Cl$_2$ was added to the reaction. The polymerization was allowed to stir overnight and a solution of the third monomer D-LA (1.267 g, 8.80 mmol) in CH$_2$Cl$_2$ was added to the reaction mixture. The reaction was allowed to stir overnight and then quenched with acidic Et$_2$O (0.5 mL of 1.5 M HCl in Et$_2$O). A few drops of the mixture were removed to check conversion and the remaining mixture was concentrated under vacuum and the polymer was precipitated with cold MeOH. The resulting polymer was washed with cold MeOH (3×3 mL) and dried under vacuum. The polymer was then redissolved in dry CH$_2$Cl$_2$, a thermal stabilizer (TNPP, 35.0 mg) was added and the solvent was removed under vacuum overnight. Parallel experiments of the synthesis of only the first block and the first two block polymers were carried out under the same condition to get information of the molecular weight of each block.

Immortal polymerization of rac-LA with 1 in the presence of ethanol. A 20 mL scintillation vial vas charged with a stirring bar and a 0.25 mL solution of 1 in CH$_2$Cl$_2$ (0.0182 M, 0.0045 mmol). 13.4 µL of ethanol in CH$_2$Cl$_2$ (0.685 M, 0.0092 mmol) was added to the stirring catalyst solution. Subsequently, rac-LA (654 mg, 4.5 mmol) was dissolved in CH$_2$Cl$_2$ and slowly added in to the stirring solution. The total volume of the solution was around 4 mL. The reaction was stirred overnight and then quenched with acidic Et$_2$O (0.5 mL of 1.5 M HCl). A few drops of the reaction mixture were removed to test conversion with $^1$H NMR spectroscopy. The remaining reaction mixture was dried under vacuum and dissolved in a minimum amount of $CH_2Cl_2$ and the polymer was precipitated with cold methanol. The supernatant was decanted off and the polymer was then washed with cold methanol (1×3 mL) and dried under vacuum overnight.

Immortal polymerization of L-LA with 1 in the presence of MePEG-$_7$. A 20 mL scintillation vial vas charged with a stirring bar and a 0.90 mL solution of 1 in $CH_2Cl_2$ (0.00309 M, 0.00278 mmol). 44.7 μL of MePEG$_7$ in $CH_2Cl_2$ (0.0622 M, 0.00278 mmol) was added to the stirring catalyst solution. Subsequently, rac-LA (401 mg, 2.78 mmol) was dissolved in $CH_2Cl_2$ and slowly added in to the stirring solution. The total volume of the solution was around 5 mL. The reaction was stirred overnight and then quenched with acidic $Et_2O$ (0.5 mL of 1.5 M HCl). A few drops of the reaction mixture were removed to test conversion with $^1$ H NMR spectroscopy. The remaining reaction mixture was dried under vacuum and dissolved in a minimum amount of CH2Cl$_2$ and the polymer was precipitated with cold methanol. The supernatant was decanted off and the polymer was then washed with cold methanol (1×3 mL) and dried under vacuum overnight.

Immortal polymerization of rac-LA with 1 in the presence of MePEG$_{114}$. A round bottom flask was charged with 1 in $CH_2Cl_2$ (73.5 mg, 0.0668 mmol) and MePEG$_{114}$ in THF (1.67 g, 0.334 mmol). The mixture was allowed to stir for half an hour and dried under vacuum. $CH_2Cl_2$ was added to dissolve the dry residue again. While stirring, rac-LA in $CH_2Cl_2$ (5.00 g, 34.7 mmol) was added slowly to the solution. The reaction was allowed to stir overnight and then was quenched with acidic $Et_2O$ (0.5 mL of a 1.5 M HCl in $Et_2O$). A few drops of the reaction mixture were removed to check conversion with $^1$H NMR spectroscopy. The remaining mixture was dried under vacuum and dissolved in a minimum amount of $CH_2Cl_2$ and the polymer was precipitated in 1:1 $Et_2O$/hexane. The supernatant was decanted off and the polymer was washed with 1:1 $Et_2O$/hexane (3×3 mL) and dried under vacuum overnight.

Figure 12:
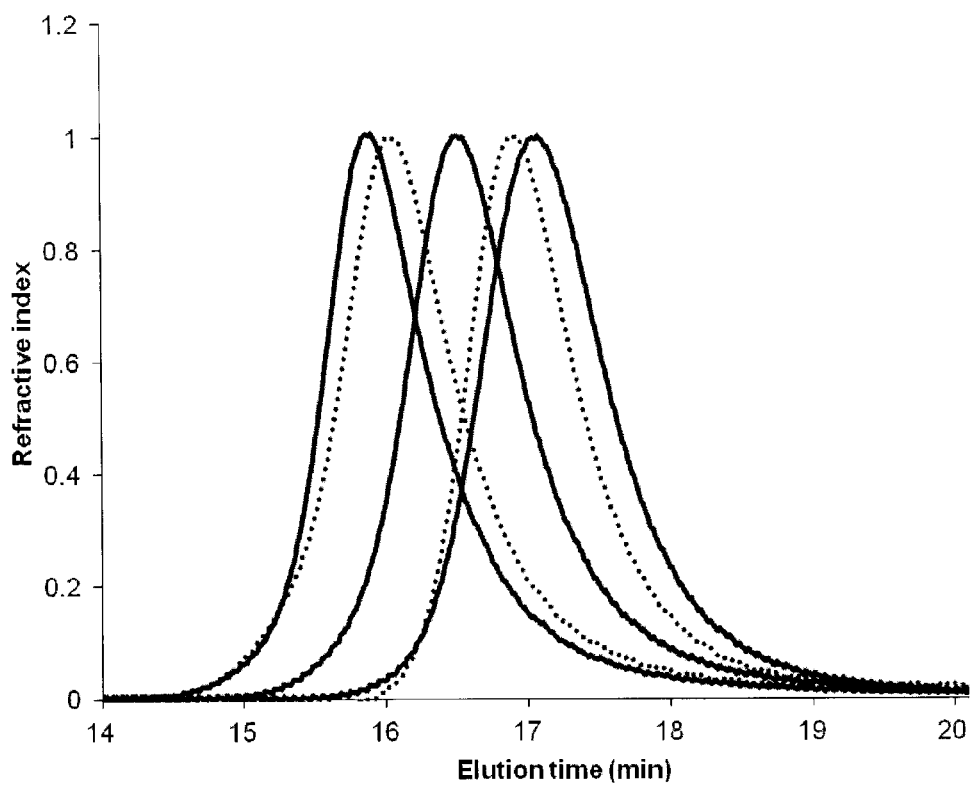
FIG. 12 shows a GPC elution diagram for polymers produced by iROP with a dinuclear Indium catalyst of rac-LA with ethanol.

Different equivalents of EtOH (based on the amount of catalyst 1) were used in the iROP of lactide. The molecular weight decreased as more EtOH was added. GPC traces of the resulting polymers (see FIG. 12; from left to right, the peaks correspond to entry 1, entry 2, entry 3, entry 4 and entry 5 in Table 2 below) showed narrow molecular weight distribution for all of the product polymers. The PDI value and P$_m$ remain similar to those in the absence of the alcohol, making iROP an attractive way to decrease catalyst usage and scale up polymerization.

TABLE 2

Polymerization of rac-LA with different equivalents of EtOH

| Entry[a] | [EtOH]/[1] | Conv. | M$_{n,theo}$[b] (kDa) | M$_{n,expt}$ (kDa) | PDI | P$_m$ |
|---|---|---|---|---|---|---|
| 1 | 0 | 99 | 144.0 | 109.4 | 1.02 | 0.57 |
| 2 | 1 | 98 | 72.0 | 75.53 | 1.03 | 0.60 |
| 3 | 2 | 99 | 48.0 | 48.29 | 1.02 | 0.60 |
| 4 | 3 | 98 | 36.0 | 33.46 | 1.01 | 0.58 |
| 5 | 4 | 98 | 28.8 | 30.79 | 1.01 | 0.59 |

[a]All the experiments were done in CH$_2$Cl$_2$, with 5.0 mg catalyst, [rac-LA]/[1] = 1000.
[b]Calculated from: M$_n$ = MW$_{LA}$ × [LA]/([1] + [EtOH]) × Conv..

Immortal ROP of LA with low molecular weight MePEG (M$_n$=350 g/mol, denoted as MePEG$_7$ with the subscript 7 representing the number of units of ethylene oxide in the molecule) resulted in well-defined polymers with low PDIs (see below Table 3, entries 1-5). The molecular weights of the resulting polymers were much lower than those in the situation without MePEG$_7$. As the amount of MePEG$_7$ used increases, the molecular weights of the polymers produced decreases. The experimental molecular weights fit the theoretical values very well, proving that in the short chain MePEG, the hydroxy group is active enough to perform chain transfer with the growing polymer chain during the polymerization.

TABLE 3

Polymerization of L-LA with different equivalent of MePEG

| Entry[a] | ROH | [LA]/[ROH]/[1] | Conv. | M$_{n, theo}$ (kDa) | M$_{n, expt}$ (kDa) | PDI |
|---|---|---|---|---|---|---|
| 1 | MePEG$_7$ | 1000/0/1 | 98 | 141.1[b] | 144.2 | 1.06 |
| 2 | MePEG$_7$ | 1000/1/1 | 99 | 71.30[b] | 72.41 | 1.04 |
| 3 | MePEG$_7$ | 1000/2/1 | 99 | 47.53[b] | 49.54 | 1.03 |
| 4 | MePEG$_7$ | 1000/3/1 | 98 | 35.29[b] | 39.14 | 1.02 |
| 5 | MePEG$_7$ | 1000/4/1 | 99 | 28.52[b] | 29.79 | 1.02 |
| 6 | MePEG$_{114}$ | 1000/5/1 | >99 | 33.8[c] | 31.90 | 1.14 |
| 7 | MePEG$_{114}$ | 520/5/1 | >99 | 20.0[c] | 23.36 | 1.46 |
| 8 | MePEG$_{114}$ | 500/10/1 | >99 | 12.2[c] | 15.95 | 2.30 |
| 9 | MePEG$_{114}$ | 250/10/1 | >99 | 8.6[c] | 10.01 | 2.21 |

[a]All the experiments were done in CH$_2$Cl$_2$ at 25° C.
[b]Calculated from: M$_n$ = MW$_{LA}$ ×[LA]/([1] + [MePEG$_7$]) × Conv. + 350 g/mol.
[c]Calculated from: M$_n$ = MW$_{LA}$ ×[LA]/[MePEG$_{114}$] × Conv. + 5000 g/mol.

Figure 13:
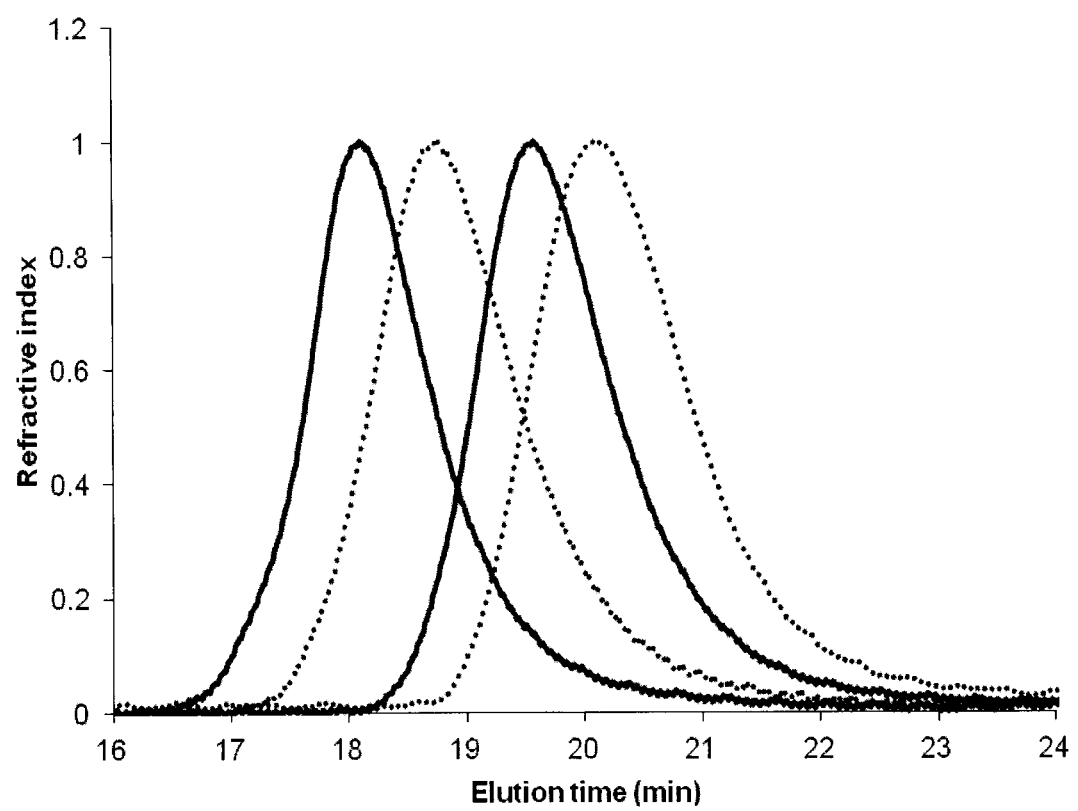
FIG. 13 shows a GPC elution diagram for polymers produced by iROP of L-LA with MePEG$_{114}$ by a dinuclear Indium catalyst.

In the experiments of iROP of LA with higher molecular weight MePEG (M$_n$=5000 g/mol, denoted as MePEG$_{114}$ with the subscript 114 representing the number of units of ethylene oxide in the molecule) (Table 3, entries 6-10), 1 was stirred with MePEG$_{114}$ for 30 min and pumped down to dryness to remove the generated ethanol. Therefore the amount of initiating group equals the amount of MePEG$_{114}$. The molecular weights of the resulting polymers were close to the theoretical values. PDI values are higher with shorter chain PLA segments in the copolymers, likely due to the larger PDI of the commercially available MePEG$_{1114}$ itself. Since MePEG$_{114}$ is not as monodispersed as the homopolymers made with our living catalyst, the incorporation of MePEG$_{114}$ increases the PDI of the copolymers. As the PLA block gets longer, the differences of the copolymer chain lengths caused by MePEG$_{1114}$ become less significant, thus resulting in a lower PDI. Another possible reason accounting for the high PDI is that THF is not a good solvent for this copolymer. Long chain PEG is not soluble in THF, which is the same situation for copolymers containing MePEG$_{114}$. Also, copolymers might form aggregates in THF, which can be detected by the light scattering detector of GPC, although no peaks were observed from the refractive index detector, due to low concentrations (see FIG. 13; from left to right, the peaks correspond to entry 6, entry 7, entry 8 and entry 9 in Table 3 respectively.

Example: fBBL-1 and fBBL-2

Functionalized four membered lactones fBBL-1 and fBBL-2 were synthesized by carbonylation of epoxide compounds.(John W. Kramer, Emil B. Lobkovsky, and Geoffrey W. Coates ORGANIC LETTERS 2006 Vol. 8, No. 17 3709-3712)

fBBL-1 and fBBL-2 were used in the ring-opening polymerization using dinuclear Indium catalysts of the present invention as shown in below scheme.

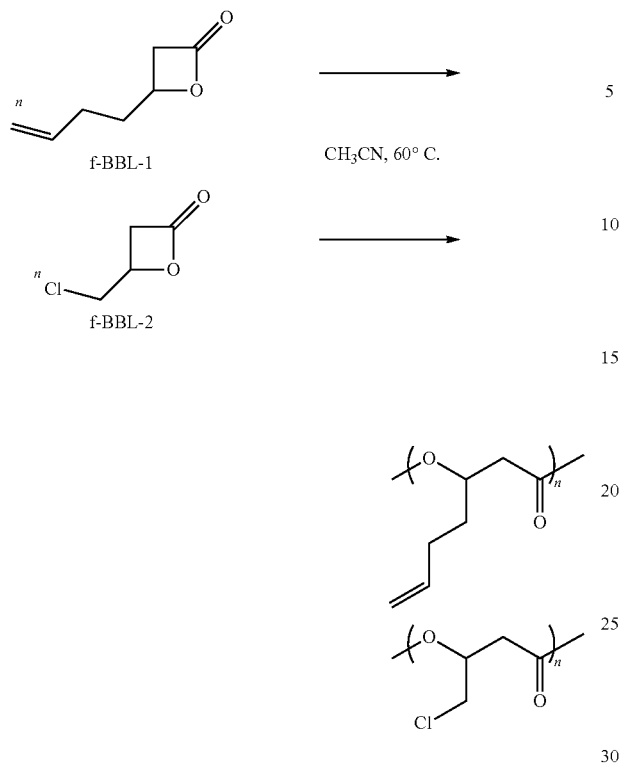

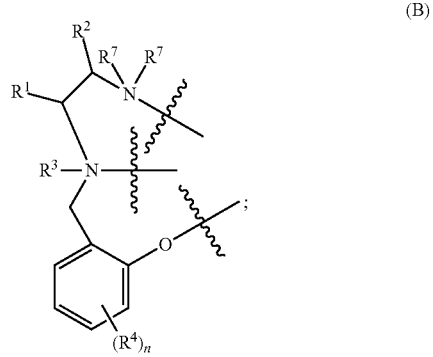

each $R^7$ independently is —$(C_1$-$C_4)$alkyl;
$Y^1$ is O—$R^6$ or OH;
$Y^2$ is O—$R^6$, OH, Cl, Br, or I;
each $R^6$ independently is —$(C_1$-$C_6)$alkyl;
n is 0 to 4;
each $R^1$ and $R^2$ is independently a —H or —$(C_1$-$C_4)$alkyl; or $R^1$ and $R^2$ together with the carbon atoms to which they are bonded form a $(C_5$-$C_7)$cycloalkyl ring, optionally substituted with up to two groups selected independently from —$(C_1$-$C_4)$alkyl, —$(C_1$-$C_4)$alkoxy, phenyl, —$CF_3$, —F, —Cl, —Br, and —I;
$R^3$ is —H or —$(C_1$-$C_3)$alkyl;
each X is independently an anionic ligand; and
each $R^4$ independently is —$(C_1$-$C_5)$alkyl;
or a stereoisomer thereof; and
provided that when the tridentate ligands $L^1$ and $L^2$ are represented by structural formula

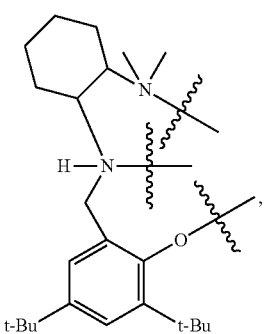

and (a) each X is Cl, and $Y^1$ is —O—$(C_2)$alkyl, then $Y^2$ is O—$R^6$, OH, Br, or I; (b) each X is I, and $Y^1$ is —O—$(C_2)$alkyl, then $Y^2$ is O—$R^6$, OH, Cl, Br, wherein $R^6$ is —$C_1$-alkyl, —$C_3$-alkyl, —$C_4$-alkyl, —$C_5$-alkyl, or —$C_6$-alkyl; or (c) each X is Cl, and $Y^1$ is —OH, then $Y^2$ is O—$R^6$, Cl, Br, or I;

and wherein the cyclic ester monomer is optionally represented by structural formula (I)

All publications, patents and patent applications mentioned in this Specification are indicative of the level of skill of those skilled in the art to which this invention pertains and are herein incorporated by reference to the same extent as if each individual publication, patent, or patent application was specifically and individually indicated to be incorporated by reference.

While this invention has been particularly shown and described with references to example embodiments thereof, it will be understood by those skilled in the art that various changes in form and details may be made therein without departing from the scope of the invention encompassed by the appended claims.

What is claimed is:

1. A method comprising polymerizing a cyclic ester monomer with a catalyst represented by structural formula (A) or a stereoisomer thereof under conditions suitable for ring-opening polymerization of the cyclic ester monomer:

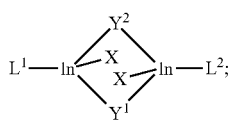

wherein $L^1$ and $L^2$ are each independently a tridentate ligand represented by structural formula (B):

wherein m is 1 to 4;

Q is —CH$_2$—, —C(HR$^m$)—, or —C(R$^m$R$^m$)—;

each Z is independently —CH$_2$—, —O—, —C(=O)—, —C(HR$^m$)—, or —C(R$^m$R$^m$)—; and each R$^m$ is i) —(C$_1$-C$_5$)alkyl optionally substituted with hydroxyl, —(C$_1$-C$_3$)alkoxy or —O—(C$_1$-C$_3$)alkenyl, or ii) —(C$_1$-C$_5$)alkenyl;

or a stereoisomer thereof;

provided that (i) no more than one Z is —O—, (ii) no more than one Z is —C(=O)—, (iii) at least one carbon ring atom is between any two oxygen ring atoms, (iv) at least one carbon ring atom is between any two —C(=O)— groups, and (v) at least one of any three consecutive ring members is —CH$_2$—, —C(HR$^m$)—, or —C(R$^m$R$^m$)—.

2. The method of claim 1, wherein the cyclic ester monomer is represented by structural formula (I):

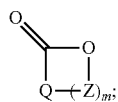

(I)

wherein m is 1 to 4;

Q is —CH$_2$—, —C(HR$^m$)—, or —C(R$^m$R$^m$)—;

each Z is independently —CH$_2$—, —O—, —C(=O)—, —C(HR$^m$)—, or —C(R$^m$R$^m$)—; and each R$^m$ is i) —(C$_1$-C$_5$)alkyl optionally substituted with hydroxyl, —(C$_1$-C$_3$)alkoxy or —O—(C$_1$-C$_3$)alkenyl, or ii) —(C$_1$-C$_5$)alkenyl;

or a stereoisomer thereof;

provided that (i) no more than one Z is —O—, (ii) no more than one Z is —C(=O)—, (iii) at least one carbon ring atom is between any two oxygen ring atoms, (iv) at least one carbon ring atom is between any two —C(=O)— groups, and (v) at least one of any three consecutive ring members is —CH$_2$—, —C(HR$^m$)—, or —C(R$^m$R$^m$)—; or wherein the cyclic ester monomer is represented by structural formula (II) or (III)

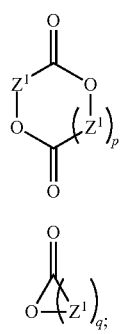

(II)

(III)

wherein p is 1 or 2;

q is 2 to 5;

each Z$^1$ is independently —CH$_2$, —C(HR$^m$)—, or —C(R$^m$R$^m$)—; and each R$^m$ is i) —(C$_1$-C$_5$)alkyl optionally substituted with hydroxyl, —(C$_1$-C$_3$)alkoxy or —O—C$_1$-C$_3$)alkenyl, or ii) C$_1$-C$_5$)alkenyl;

or a stereoisomer thereof.

3. The method of claim 2, wherein each X is independently Cl, Br, or I.

4. The method of claim 2, wherein L$^1$ and L$^2$ are each independently a tridentate ligand represented by structural formula

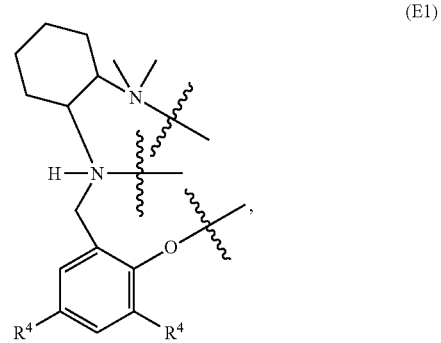

(E1)

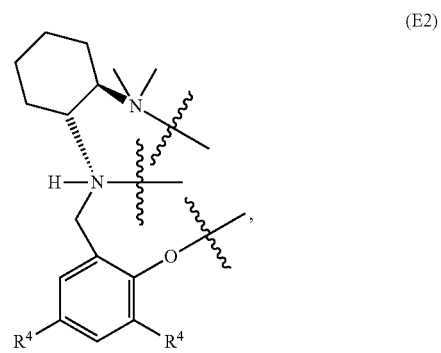

(E2)

or a stereoisomer of the tridentate ligand represented by structural formula E1 or E2.

5. The method of claim 2, wherein the catalyst is represented by structural formula (A):

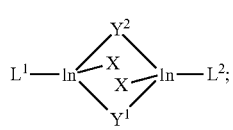

(A)

wherein L$^1$ and L$^2$ are each independently a tridentate ligand represented by structural formula (B):

(B)
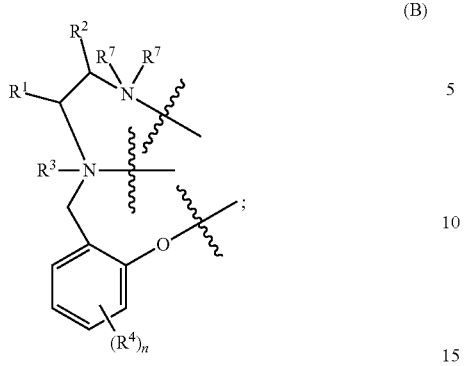

(D1)
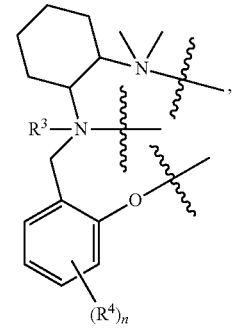

each $R^7$ independently is —$(C_1$-$C_4)$alkyl;
$Y^1$ is O—$(C_1$-$C_6)$alkyl or OH;
$Y^2$ is O—$(C_1$-$C_6)$alkyl, OH, Cl, Br, or I;
n is 0 to 4;
each $R^1$ and $R^2$ is independently —H or —$(C_1$-$C_4)$alkyl; or $R^1$ and $R^2$ together with the carbon atoms to which they are bonded form a $(C_5$-$C_7)$cycloalkyl ring, optionally substituted with up to two groups selected independently from —$(C_1$-$C_4)$alkyl, —$(C_1$-$C_4)$alkoxy, phenyl, —$CF_3$, —F, —Cl, —Br, and —I;
$R^3$ is —H or —$(C_1$-$C_3)$alkyl;
each X is independently an anionic ligand; and
each $R^4$ independently is —$(C_1$-$C_5)$alkyl;
or a stereoisomer of the catalyst represented by structural formula (A);
provided that when $L^1$ and $L^2$ are both represented by structural formula (D2)
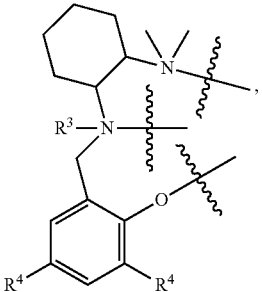

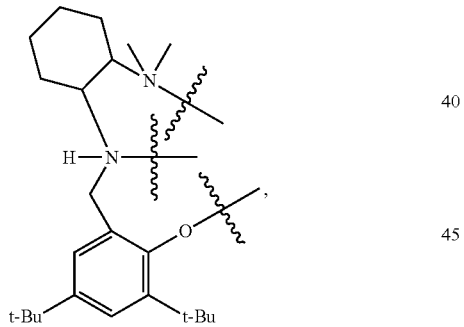

(D3)
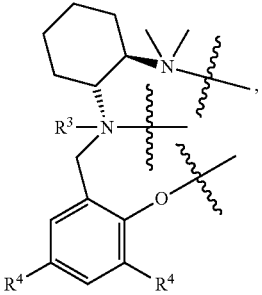

and (a) each X is Cl, and $Y^1$ is O—$(C_2)$alkyl, then $Y^2$ is O—$(C_1)$alkyl, O—$(C_3)$alkyl, O—$(C_4)$alkyl, O—$(C_5)$alkyl, O—$(C_6)$alkyl, Br, or I; (b) each X is I, and $Y^1$ is —O—$(C_2)$alkyl, then $Y^2$ is O—$(C_1)$alkyl, O—$(C_3)$alkyl, O—$(C_4)$alkyl, O—$(C_5)$alkyl, O—$(C_6)$alkyl, Cl, or Br; (c) each X is Br, and $Y^1$ is —O—$(C_2)$alkyl, then $Y^2$ is O—$(C_1)$alkyl, O—$(C_3)$alkyl, O—$(C_4)$alkyl, O—$(C_5)$alkyl, O—$(C_6)$alkyl, Cl, or I; (d) each X is Cl, and $Y^1$ is OH, then $Y^2$ is O—$(C_1$-$C_6)$alkyl, Cl, Br, or I; (e) each X is Br, and $Y^1$ is OH then $Y^2$ is O—$C_1$-$C_6)$alkyl, Cl, Br, or I; or (f) each X is I, and $Y^1$ is OH, then $Y^2$ is O—$(C_1$-$C_6)$alkyl, Cl, Br, or I.

6. The method of claim 5, wherein each X is independently Cl, Br, or I.

7. The method of claim 6, wherein $L^1$ and $L^2$ are each independently a tridentate ligand represented by structural formula or a stereoisomer of the tridentate ligand represented by structural formula D1, D2 or D3; or wherein $L^1$ and $L^2$ are each independently a tridentate ligand represented by structural formula (E1)
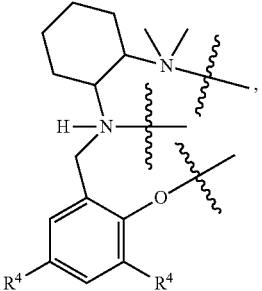

77
-continued (E2)
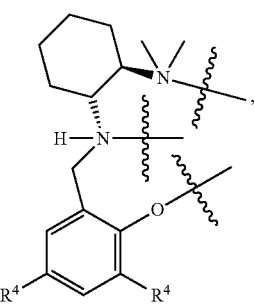

or a stereoisomer of the tridentate ligand represented by structural formula E1 or E2.

8. The method of claim 1, wherein the cyclic ester monomer is a dilactone or a lactone represented by structural formula (IV)
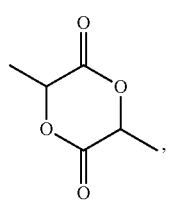

(V)
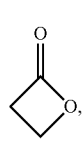

(VI)
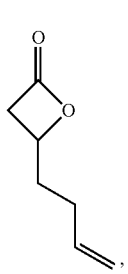

(VII)
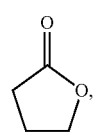

(VIII)
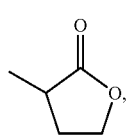

(IX)
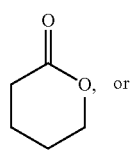
or

78
-continued (X)
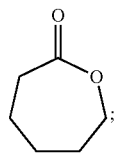

or a stereoisomer thereof.

9. The method of claim 1, wherein:
i) the tridentate ligand is chiral, and (a) conditions are provided for the polymerizing to exert enantiomorphic site control; (b) the polymerizing results in an iso-enriched polymer; or (c) both (a) and (b);
ii) the polymerizing is substantially first order in catalyst and monomer concentrations; or
iii) the polymerizing is living polymerizing.

10. The method of claim 1, wherein it is further provided that when $L^1$ and $L^2$ are both represented by structural formula

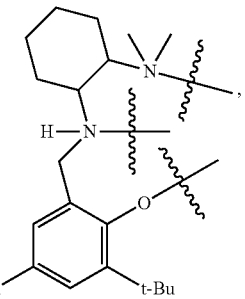

and the catalyst is represented by structural formula (P5)
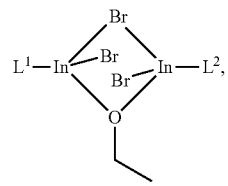

(P6)

(P7)
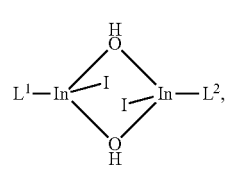

(P4) 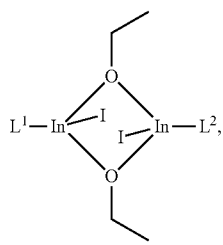

(P5) 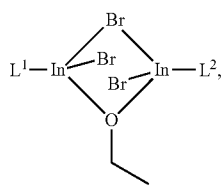

(P6) 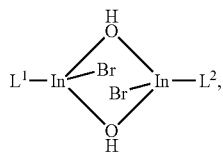

(P7) 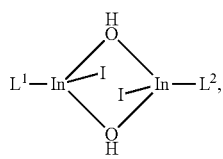

(P8) 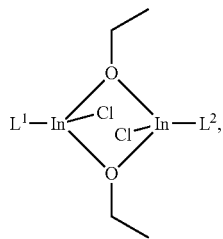

(P9) 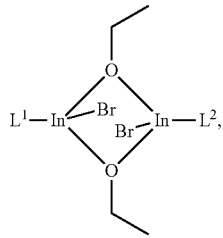

(P10) 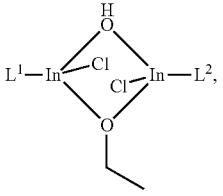

(P11) 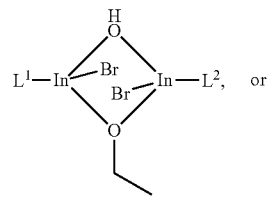

(P12) 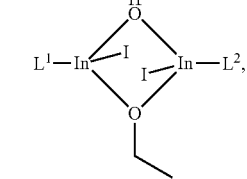

then the cyclic ester monomer is not L-lactide, D-lactide, meso-lactide or rac-lactide.

11. A polymer prepared by process comprising polymerizing a cyclic ester monomer with a catalyst represented by structural formula (A) or a stereoisomer thereof under conditions suitable for ring-opening polymerization of the cyclic ester monomer:

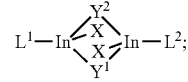
(A)

wherein $L^1$ and $L^2$ are each independently a tridentate ligand represented by structural formula (B):

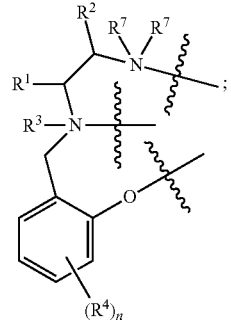
(B)

each $R^7$ independently is —$(C_1$-$C_4)$alkyl;
$Y^1$ is O—$R^6$ or OH;
$Y^2$ is O—$R^6$, OH, Cl, Br, or I;
each $R^6$ independently is —$(C_1$-$C_6)$alkyl;
n is 0 to 4;
each $R^1$ and $R^2$ is independently a —H or —$(C_1$-$C_4)$alkyl; or $R^1$ and $R^2$ together with the carbon atoms to which they are bonded form a $(C_5$-$C_7)$cycloalkyl ring, optionally substituted with up to two groups selected independently from —$(C_1$-$C_4)$alkyl, —$(C_1$-$C_4)$alkoxy, phenyl, —$CF_3$, —F, —Cl, —Br, and —I;
$R^3$ is —H or —$(C_1$-$C_3)$alkyl;
each X is independently an anionic ligand; and
each $R^4$ independently is —$(C_1$-$C_5)$alkyl;
or a stereoisomer thereof; and provided that when the tridentate ligands $L^1$ and $L^2$ are represented by structural formula

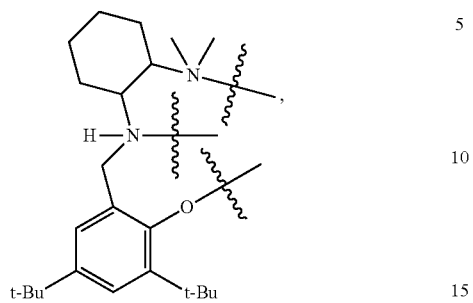

and (a) each X is Cl, and $Y^1$ is —O—$(C_2)$alkyl, then $Y^2$ is O—$R^6$, OH, Br, or I; (b) each X is I, and $Y^1$ is —O—$(C_2)$alkyl, then $Y^2$ is O—$R^6$, OH, Cl, or Br, wherein $R^6$ is —$C_1$-alkyl, —$C_3$-alkyl, —$C_4$-alkyl, —$C_5$-alkyl, or —$C_6$-alkyl; or (c) each X is Cl, and $Y^1$ is —OH, then $Y^2$ is O—$R^6$, Cl, Br, or I.

12. The polymer of claim 11, wherein he polymer is iso-enriched, and, optionally, has a $P_m$ value between 0.53 and 0.62, or is characterized by a polydispersity index of less than 1.5.

* * * * *